(12) United States Patent
Malcuit et al.

(10) Patent No.: US 10,077,424 B2
(45) Date of Patent: Sep. 18, 2018

(54) METHODS OF PRODUCING RPE CELLS AND COMPOSITIONS OF RPE CELLS

(71) Applicant: Astellas Institute for Regenerative Medicine, Marlborough, MA (US)

(72) Inventors: Christopher Malcuit, Ware, MA (US); Linda Lemieux, Hubbardston, MA (US); William Holmes, Worcester, MA (US); Pedro Huertas, Concord, MA (US); Lucy Vilner, Johnston, RI (US)

(73) Assignee: Astellas Institute for Regenerative Medicine, Marlborough, MA (US)

(*) Notice: Subject to any disclaimer, the term of this patent is extended or adjusted under 35 U.S.C. 154(b) by 0 days.

(21) Appl. No.: 14/254,833

(22) Filed: Apr. 16, 2014

(65) Prior Publication Data
US 2015/0086512 A1    Mar. 26, 2015

Related U.S. Application Data

(63) Continuation of application No. 12/682,712, filed as application No. PCT/US2008/011669 on Oct. 10, 2008, now abandoned.

(60) Provisional application No. 61/009,908, filed on Jan. 2, 2008, provisional application No. 61/009,911, filed on Jan. 2, 2008, provisional application No. 60/998,668, filed on Oct. 12, 2007, provisional application No. 60/998,766, filed on Oct. 12, 2007.

(51) Int. Cl.
*C12N 5/079* (2010.01)
*A61K 35/12* (2015.01)
*A61K 35/30* (2015.01)

(52) U.S. Cl.
CPC ............ *C12N 5/0621* (2013.01); *A61K 35/30* (2013.01); *A61K 35/12* (2013.01); *C12N 2501/10* (2013.01); *C12N 2501/734* (2013.01); *C12N 2506/02* (2013.01); *C12N 2509/00* (2013.01); *C12N 2533/54* (2013.01)

(58) Field of Classification Search
CPC combination set(s) only.
See application file for complete search history.

(56) References Cited

U.S. PATENT DOCUMENTS

| | | | |
|---|---|---|---|
| 6,245,566 B1 | 6/2001 | Gearhart et al. | |
| 6,331,313 B1 | 12/2001 | Wong et al. | |
| 6,335,205 B1 | 1/2002 | Bausback | |
| 6,642,048 B2 | 11/2003 | Xu et al. | |
| 7,247,479 B2 | 7/2007 | Kochanek et al. | |
| 7,462,471 B2 | 12/2008 | Mikos et al. | |
| 7,625,582 B2 | 12/2009 | Wong | |
| 7,736,896 B2 | 6/2010 | Klimanskaya et al. | |
| 7,794,704 B2 | 9/2010 | Klimanskaya et al. | |
| 7,795,025 B2 | 9/2010 | Klimanskaya et al. | |
| 8,198,085 B2 | 6/2012 | Kanias et al. | |
| 8,268,303 B2 | 9/2012 | Klimanskaya et al. | |
| 9,040,038 B2 | 5/2015 | Klimanskaya et al. | |
| 9,040,039 B2 | 5/2015 | Klimanskaya et al. | |
| 9,040,770 B2 | 5/2015 | Klimanskaya et al. | |
| 9,045,732 B2 | 6/2015 | Klimanskaya et al. | |
| 9,080,150 B2 | 7/2015 | Klimanskaya et al. | |
| 9,181,524 B2 | 11/2015 | Klimanskaya et al. | |
| 9,193,950 B2 | 11/2015 | Klimanskaya et al. | |
| 9,562,217 B2 | 2/2017 | Klimanskaya et al. | |
| 9,649,340 B2 | 5/2017 | Klimanskaya et al. | |
| 9,650,607 B2 | 5/2017 | Klimanskaya et al. | |
| 9,730,962 B2 | 8/2017 | Klimanskaya et al. | |
| 2002/0022268 A1 | 2/2002 | Xu et al. | |
| 2002/0035735 A1 | 3/2002 | Schatten et al. | |
| 2002/0076747 A1* | 6/2002 | Price | A01K 67/0275 435/69.1 |
| 2003/0084471 A1 | 5/2003 | Beach et al. | |
| 2003/0087859 A1 | 5/2003 | Kochanek et al. | |
| 2004/0018617 A1 | 1/2004 | Hwang | |
| 2004/0086494 A1 | 5/2004 | John | |
| 2004/0133095 A1 | 7/2004 | Dunki-Jacobs et al. | |
| 2005/0032126 A1 | 2/2005 | Coombs et al. | |
| 2006/0002900 A1 | 1/2006 | Binder et al. | |
| 2006/0018886 A1 | 1/2006 | Klimanskaya et al. | |
| 2006/0031951 A1 | 2/2006 | Klimanskaya | |
| 2006/0147437 A1 | 7/2006 | Allen et al. | |
| 2006/0286544 A1 | 12/2006 | Mandal et al. | |
| 2007/0031386 A1 | 2/2007 | Klimanskaya | |
| 2007/0061910 A1 | 3/2007 | Han et al. | |
| 2008/0057041 A1 | 3/2008 | Chung et al. | |
| 2009/0226955 A1 | 9/2009 | Elliot et al. | |
| 2009/0233324 A1 | 9/2009 | Kopf-Sill | |
| 2010/0057056 A1 | 3/2010 | Gurtner et al. | |
| 2010/0105100 A1 | 4/2010 | Sakurada et al. | |
| 2010/0299765 A1 | 11/2010 | Klimanskaya et al. | |
| 2011/0027333 A1 | 2/2011 | Idelson et al. | |
| 2011/0117062 A1 | 5/2011 | Klimanskaya et al. | |
| 2011/0117063 A1 | 5/2011 | Klimanskaya et al. | |

(Continued)

FOREIGN PATENT DOCUMENTS

CN    1449448 A    10/2003
CN    101155913 A    4/2008

(Continued)

OTHER PUBLICATIONS

Peng et al. Apical and Basal Regulation of the Permeability of the Retinal Pigment Epithelium. Investigative Ophthalmology & Visual Science, Feb. 2003, vol. 44, No. 2. p. 808-817.*

(Continued)

*Primary Examiner* — Taeyoon Kim
(74) *Attorney, Agent, or Firm* — Wolf, Greenfield & Sacks, P.C.

(57) ABSTRACT

The present invention provides improved methods for producing RPE cells from human embryonic stem cells or from other human pluripotent stem cells. The invention also relates to human retinal pigmented epithelial cells derived from human embryonic stem cells or other human multipotent or pluripotent stem cells. hRPE cells derived from embryonic stem cells are molecularly distinct from adult and fetal-derived RPE cells, and are also distinct from embryonic stem cells. The hRPE cells described herein are useful for treating retinal degenerative diseases.

13 Claims, 7 Drawing Sheets

(56) References Cited

U.S. PATENT DOCUMENTS

| | | |
|---|---|---|
| 2011/0274662 A1 | 11/2011 | Malcuit et al. |
| 2013/0022680 A1 | 1/2013 | Klimanskaya et al. |
| 2013/0149284 A1 | 6/2013 | Malcuit et al. |
| 2013/0195806 A1 | 8/2013 | Gay et al. |
| 2013/0196369 A1 | 8/2013 | Hikita |
| 2013/0302286 A1 | 11/2013 | Klimanskaya et al. |
| 2013/0302288 A1 | 11/2013 | Klimanskaya et al. |
| 2013/0302426 A1 | 11/2013 | Klimanskaya et al. |
| 2013/0302824 A1 | 11/2013 | Klimanskaya et al. |
| 2013/0316451 A1 | 11/2013 | Klimanskaya et al. |
| 2013/0316452 A1 | 11/2013 | Klimanskaya et al. |
| 2014/0294779 A1 | 10/2014 | Klimanskaya et al. |
| 2014/0356432 A1 | 12/2014 | Klimanskaya et al. |
| 2015/0086512 A1 | 3/2015 | Malcuit et al. |
| 2015/0328261 A1 | 11/2015 | Klimanskaya et al. |
| 2015/0366915 A1 | 12/2015 | Gay et al. |
| 2018/0023052 A1 | 1/2018 | Klimanskaya et al. |
| 2018/0064761 A1 | 3/2018 | Klimanskaya et al. |

FOREIGN PATENT DOCUMENTS

| | | |
|---|---|---|
| CN | 101563449 A | 10/2009 |
| EP | 1 454 641 A2 | 9/2004 |
| JP | 9-501303 | 2/1997 |
| JP | 2002-500202 | 1/2002 |
| JP | 2003-111588 A | 4/2003 |
| JP | 2003-523766 | 8/2003 |
| JP | 2003-530879 A | 10/2003 |
| JP | 2003-530880 | 10/2003 |
| JP | 2006-500003 A1 | 1/2006 |
| JP | 2007-522131 | 8/2007 |
| JP | 2007-535941 | 12/2007 |
| JP | 2008-54508 | 12/2008 |
| JP | 2009-517001 | 4/2009 |
| WO | WO 94/25569 A1 | 11/1994 |
| WO | WO 98/30679 A1 | 7/1998 |
| WO | WO 99/34834 A1 | 7/1999 |
| WO | WO 99/045094 A1 | 9/1999 |
| WO | WO 01/30978 A1 | 5/2001 |
| WO | WO 01/51616 A2 | 7/2001 |
| WO | WO 01/62899 A2 | 8/2001 |
| WO | WO 01/81551 A2 | 11/2001 |
| WO | WO 2001/81549 A2 | 11/2001 |
| WO | WO 02/016620 A2 | 2/2002 |
| WO | WO 02/42445 A2 | 5/2002 |
| WO | WO 2002/092756 A2 | 11/2002 |
| WO | WO 2003/006950 A2 | 1/2003 |
| WO | WO 03/046141 A2 | 6/2003 |
| WO | WO 03/049773 A1 | 6/2003 |
| WO | WO 03/050249 A2 | 6/2003 |
| WO | WO 03/087368 A2 | 10/2003 |
| WO | WO 2004/098285 A2 | 11/2004 |
| WO | WO 2005/070011 A2 | 8/2005 |
| WO | WO 2005/111197 A1 | 11/2005 |
| WO | WO 2006/040763 A2 | 4/2006 |
| WO | WO 2006/052646 A2 | 5/2006 |
| WO | WO 2006/080952 A2 | 8/2006 |
| WO | WO 2006/085209 A1 | 8/2006 |
| WO | WO 2006/126972 A1 | 11/2006 |
| WO | WO 2007/020655 A1 | 2/2007 |
| WO | WO 2008/020675 A1 | 2/2008 |
| WO | WO 2008/129554 A1 | 10/2008 |
| WO | WO 2009/050657 A2 | 4/2009 |
| WO | WO 2009/051671 A1 | 4/2009 |
| WO | WO 2011/063005 A2 | 5/2011 |
| WO | WO 2012/012803 A2 | 1/2012 |
| WO | WO 2012/149484 A2 | 11/2012 |
| WO | WO 2013/184809 A1 | 12/2013 |

OTHER PUBLICATIONS

Moon et al. Generation, Culture, and Differentiation of Human Embryonic Stem Cells for Therapeutic Applications. Molecular Therapy vol. 13, No. 1, Jan. 2006. p. 5-14.*

Mitalipov et al. Isolation and Characterization of Novel Rhesus Monkey Embryonic Stem Cell Lines. Stem Cells 2006;24:2177-2186.*

Invitation to Pay Additional Fees for Application No. PCT/US2008/011669 dated Dec. 17, 2008.

International Preliminary Report on Patentability for Application No. PCT/US2008/011669 dated Feb. 23, 2009.

International Preliminary Report on Patentability for Application No. PCT/US2008/011669 dated Apr. 13, 2010.

Supplementary European Search Report, in application No. EP08839134.7 dated Jan. 10, 2011.

[No Author Listed], A study of implantation of human embryonic stem cell derived retinal pigment epithelium in subjects with acute wet age related macular degeneration and recent rapid vision decline. First received Sep. 19, 2012. Last verified Dec. 2013. NCT01691261 http://clinicaltrials.gov/ct2/show/NCT01691261?term=nct01691261&rank=1 [Accessed Dec. 16, 2013] 3 Pages.

[No Author Listed], ACT confirms Clinical Trial Participant Showed Improvement in Vision Form 20/400 to 20/40 Following Treatment. Press release dated May 16, 2013. http://www.advancedcell.com/news-and-media/press-releases/act-confirms-clinical-trial-participant-showed-improvement-in-vision-from-20-400-to-20-40-following-treatment/index.asp [Last accessed Dec. 16, 2013] 2 Pages.

[No Author Listed], Advanced Cell Technology Announces Interim Data from Its Three Ongoing Macular Degeneration Trials. Press release dated Nov. 8, 2012. http://www.advancedcell.com/documents/0000/0427/advanced-cell-technology-announces-interim-data-from-its-three-ongoing-macular-degeneration-trials.pdf [Last Accessed Dec. 16, 2013] 3 Pages.

[No Author Listed], Advanced Cell Technology Receives Approval from Data Safety Monitoring Board (DSMB) to Initiate Treatment of Third Patient Cohort in All Three Clinical Trials. Press release dated Mar. 2013. http://www.advancedcell.com/documents/0000/0449/advanced-cell-technology-receives-approval-from-data-safety-monitoring-board-dsmb-to-initiate-treatment-of-third-patient-cohort-in-all-three-clinical-trials.pdf [Last Accessed Dec. 16, 2013] 3 Pages.

[No Author Listed], New Science Therapeutics: Regenerative Medicine: Cell Replacement Therapy for Age Related Macular Degeneration. Pfizer-Neusentis, 2002-2012. http://www.neusentis.com/KeyPartnershipCaseStudy.php [Last Accessed Dec. 16, 2013] 3 Pages.

Afshari et al., Integrin activation or alpha 9 expression allows retinal pigmented epithelial cell adhesion on Bruch's membrane in wet age-related macular degeneration. Brain. Feb. 2010;133(Pt 2):448-64. doi:10.1093/brain/awp319.

Aisenbrey et al., Iris pigment epithelial translocation in the treatment of exudative macular degeneration: a 3-year follow-up. Arch Ophthalmol Feb. 2006;124(2):183-8.

Algvere et al., Long-term outcome of RPE allografts in non-immunosuppressed patients with AMD. Eur J Ophthalmol. Jul.-Sep. 1999;9(3):217-30.

Algvere et al., Transplantation of fetal retinal pigment epithelium in age-related macular degeneration with subfoveal neovascularization. Graefes Arch Clin Exp Ophthalmol. Dec. 1994;232(12):707-16.

Algvere et al., Transplantation of RPE in age-related macular degeneration: observations in disciform lesions and dry RPE atrophy. Graefes Arch Clin Exp Ophthalmol Mar. 1997;235(3):149-58.

Amit et al., Clonally derived human embryonic stem cell lines maintain pluripotency and proliferative potential for prolonged periods of culture, Dev Biol., Nov. 15, 2000;227(2):271-8.

answers.com. Embryonic Stem Cell. Answers Corp. 2013. http://www.answers.com/topic/embryonic-stem-cell-1. (visited May 12, 2008).

Aramant et al., Transplanted sheets of human retina and retinal pigment epithelium develop normally in nude rats. Exp Eye Res. Aug. 2002;75(2):115-25.

ATCC entry for ARPE-19, retrieved Mar. 17, 2014 from http://www.atcc.org/products/all/CRL-2302.aspx#characteristics. 1 Page.

Berger et al., Photoreceptor transplantation in retinitis pigmentosa: short-term follow-up. Ophthalmology. Feb. 2003;110(2):383-91. Abstract Only.

(56) References Cited

OTHER PUBLICATIONS

Binder et al. Transplantation of autologous retinal pigment epithelium in eyes with foveal neovascularization resulting from age-relatedmacular degeneration: a pilot study. Am J Ophthalmol. Feb. 2002;133(2):215-25.
Binder et al., Outcome of transplantation of autologous retinal pigment epithelium in age-related macular degeneration: a prospective trial. Invest Ophthalmol Vis Sci. Nov. 2004;45(11):4151-60.
Binder et al., Transplantation of the RPE in AMD. Prog Retin Eye Res. Sep. 2007;26(5):516-54. Epub Mar. 6, 2007. Abstract Only.
Brederlau, Transplantation of human embryonic stem cell-derived cells to a rat model of Parkinson's disease: effect of in vitro differentiation on graft survival and teratoma formation. Stem Cells. Jun. 2006;24(6):1433-40. Epub Mar. 23, 2006.
Brewer et al., Optimized survival of hippocampal neurons in B27-supplemented Neurobasal, a new serum-free medium combination. J Neurosci Res. Aug. 1, 1993;35(5):567-76.
Brunt et al., Stem cells and regenerative medicine—future perspectives. Can J Physiol Pharmacol. Mar. 2012;90(3):327-35. doi:10.1139/y2012-007. Epub Mar. 8, 2012.
Buchholz et al., Derivation of functional retinal pigmented epithelium from induced pluripotent stem cells. Stem Cells. Oct. 2009;27(10):2427-34. doi:10.1002/stem.189.
Cai et al., Gene expression profile of cultured adult compared to immortalized human RPE. Mol Vis. Jan. 5, 2006;12:1-14.
Canola et al., Retinal stem cells transplanted into models of late stages of retinitis pigmentosa preferentially adopt a glial or a retinal ganglion cell fate. Invest Ophthalmol Vis Sci. Jan. 2007;48(1):446-54.
Carpenter et al., Enrichment of neurons and neural precursors from human embryonic stem cells, Exp Neural., Dec. 2001;172(2):383-97.
Carr et al., Protective effects of human iPS-derived retinal pigment epithelium cell transplantation in the retinal dystrophic rat. PLoS One. Dec. 3, 2009;4(12):e8152. doi: 10.1371/journal.pone.0008152.
Chaudhry et al., Basal medium composition and serum or serum replacement concentration influences on the maintenance of murine embryonic stem cells. Ctyotechnology (2008) 5:173-9.
Chaum, Tissue Culture Wash Conditions Significantly Alter Gene Expression in Cultured Human Retinal Pigment Epithelial Cells—A Real Time RT-PCR Study (2005), Invest Ophthalmol Vis Sci. 2005;46: E-Abstract 3096.
Cheung et al., Prevalence of and risk factors for age-related macular degeneration in a multiethnic Asian cohort. Arch Ophthalmol Apr. 2012;130(4):480-6. Epub Dec. 12, 2011.
Cock et al., Plasmanate: a new plasma substitute for pediatric therapy. Calif Med. Oct. 1958;89(4):257-9.
Cosgrove, Pigment epithelium-derived factor in idiopathic pulmonary fibrosis: a role in aberrant angiogenesis. Am J Respir Crit Care Med. Aug. 1, 2004;170(3):242-51. Epub Apr. 29, 2004.
Cotsiki et al., Simian virus 40 large T antigen targets the spindle assembly checkpoint protein Bubl. Proc Natl Acad Sci U S A. Jan. 27, 2004;101(4):947-52. Epub Jan. 19, 2004.
Crafoord et al., Experimental transplantation of autologous iris pigment epithelial cells to the subretinal space. Acta Ophthalmol Scand. Oct. 2001;79(5):509-14.
Davis et al., A human retinal pigment epithelial cell line that retains epithelial characteristics after prolonged culture, Invest Ophthalmol Vis Sci., Apr. 1995;36(5):955-64.
Del Cerro et al., Histologic correlation of human neural retinal transplantation. Invest Ophthalmol Vis Sci. Sep. 2000;41(10):3142-8.
Del Priore et al., Survival of allogeneic porcine retinal pigment epithelial sheets after subretinal transplantation. Invest Ophthalmol Vis Sci. Mar. 2004;45(3):985-92.
Del Priore et al., Triple immune suppression increases short-term survival of porcine fetal retinal pigment epithelium xenografts. Invest Ophthalmol Vis Sci. Sep. 2003;44(9):4044-53.
Dunn et al., ARPE-19, a human retinal pigment epithelial cell line with differentiated properties, Exp Eye Res., Feb. 1996;62(2):155-69.
Durlu et al., Transplantation of Retinal Pigment Epithelium Using Viable Cryopreserved Cells, Cell Transplantation, vol. 6, No. 2, p. 149-162. 1997.
Emre et al., A Comparative Analysis of Human Embryonic Stem Cells Cultured in a Variety of Media Conditions. Jan. 1, 2008. 8 Pages. http://www.millipore.com/publications.nsf/a73664f9f981af8c852569b9005b4eee/73159860d3320b8a85257501006111a0/$FILE/an1237en00.pdf [last accessed Dec. 10, 2013].
Engelmann et al., RPE cell cultivation. Graefes Arch Clin Exp Ophthalmol Jan. 2004;242(1):65-7. Epub Dec. 5, 2003. First Page Only.
Faktorovich, Photoreceptor degeneration in inherited retinal dystrophy delayed by basic fibroblast growth factor. Nature. Sep. 6, 1990;347(6288):83-6.
Fuhrmann et al., Extraocular mesenchyme patterns the optic vesicle during early eye development in the embryonic chick Development, Nov. 2000;127(21):4599-609.
Gamm et al., Regulation of prenatal human retinal neurosphere growth and cell fate potential by retinal pigment epithelium and Mash1. Stem Cells. Dec. 2008;26(12):3182-93. doi: 10.1634/stemcells.2008-0300. Epub Sep. 18, 2008.
Gepstein et al. Derivation and potential applications of human embryonic stem cells. Circ Res. Nov. 15, 2002;91(10):866-76.
Gong, Effects of extracellular matrix and neighboring cells on induction of human embryonic stem cells into retinal or retinal pigment epithelial progenitors. Exp Eye Res. Jun. 2008;86(6):957-65. doi: 10.1016/j.exer.2008.03.014. Epub Mar. 28, 2008.
Gouras et al., Invest Ophthalmol Vis Sci. Oct. 2002;43(10):3307-11. Retinal degeneration and RPE transplantation in Rpe65(−/−) mice.
Guan, Loss of pigment epithelium derived factor expression in glioma progression. J Clin Pathol. Apr. 2003;56(4):277-82.
Gullapalli et al., Impaired RPE survival on aged submacular human Bruch's membrane. Exp Eye Res. Feb. 2005;80(2):235-48. Abstract Only.
Haruta et al., [Regeneration of Retinal Function by Cell Transplantation]. Jikken Igaku, 2002; 20(9):1307-1300.
Haruta, (2003), Retinal Pigment Epithelium Cells Derived from Simian Embryonic Stem Cell. The 2nd Japanese Society for Regeneration Medicine, Plenary Convention Program (Abstract).
Haruta, In vitro and in vivo characterization of pigment epithelial cells differentiated from primate embryonic stem cells. Invest Ophthalmol Vis Sci. Mar. 2004;45(3):1020-5.
Haruta, Retinal Pigment Epithelial Cells Differentiated from Primate Embryonic Stem Cells (2003), Invest Ophthalmol Vis Sci., 44:E-Abstract 381.
Hirano et al., Generation of Structures Formed by Lens and Retinal Cells Differentiating From Embryonic Stem Cells, Developmental Dynamics, Wiley-Liss, Inc., New York, NY, vol. 228, No. 4, Dec. 2003, pp. 664-671.
Ho et al., Reattachment of cultured human retinal pigment epithelium to extracellular matrix and human Bruch's membrane. Invest Ophthalmol Vis Sci. May 1997;38(6):1110-8.
Hoffman et al., Characterization and culture of human embryonic stem cells, Nat Biotechnol. Jun. 2005;23(6):699-708.
Hori et al. Growth inhibitors promote differentiation of insulin-producing tissue from embryonic stem cells PNAS Dec. 10, 2002 vol. 99 No. 25 pp. 16105-16110.
Hu et al., A cell culture medium that supports the differentiation of human retinal pigment epithelium into functionally polarized monolayers. Molecular Vision. Feb. 7, 2001; 7:14-19 http://www.molvis.org/molvis/v7/a3/ [Last accessed Dec. 4, 2013].
Humayun et al., Human neural retinal transplantation. Invest Ophthalmol Vis Sci. Sep. 2000;41(10):3100-6.
Idelson, Directed differentiation of human embryonic stem cells into functional retinal pigment epithelium cells. Cell Stem Cell. Oct. 2, 2009;5(4):396-408. doi: 10.1016/j.stem.2009.07.002.
Ikeda et al., Generation of Rx+/Pax6+ neural retinal precursors from embryonic stem cells. Proc Natl Acad Sci U S A. Aug. 9, 2005;102(32):11331-6. Epub Aug. 2, 2005.

(56) References Cited

OTHER PUBLICATIONS

Inverardi et al., Ch 56: Cell Transplantation. Transplantation Biology: Cellular and Molecular Aspects. Ed. Tiney et al. Lippincott-Raven Publishers, Philadelphia. 1996: 679-87.
Itskovitz-Eldor et al., Differentiation of human embryonic stem cells into embryoid bodies comprising the three embryonic germ layers. Mol Med. Feb. 2000;6(2):88-95.
Jean, Molecular regulators involved in vertebrate eye development. (1998), Mech. Dev., 76:3-18.
Kanuga, Characterization of genetically modified human retinal pigment epithelial cells developed for in vitro and transplantation studies. (2002), Invest Ophthalmol Vis Sci., 43(2):546-555.
Kaplan et al., Human photoreceptor transplantation in retinitis pigmentosa. A safety study. Arch Ophthalmol Sep. 1997;115(9):1168-72. Abstract only.
Kawamorita, In vitro differentiation of mouse embryonic stem cells after activation by retinoic acid. (2002), Hum Cell, 15(3):178-82.
Kawasaki et al., Generation of dopaminergic neurons and pigmented epithelia from primate ES cells by stromal cell-derived inducing activity, Proceedings of the National Academy of Sciences of USA, National Academy of Science, Washington, DC.vol. 99, No. 3, Feb. 2002, pp. 1580-1585.
Kawasaki et al., Induction of midbrain dopaminergic neurons from ES cells by stromal cell-derived inducing activity. Neuron. Oct. 2000;28(1):31-40.
Kehat Human embryonic stem cells can differentiate into myocytes with structural and functional properties of cardiomyocytes, J Clin Invest., Aug. 2001;108(3):407-14.
Kim et al., (2004), Rapid differentiation of mouse embryonic stem cells into neural lineages by drop culture system Stem Cells, Keystone Symposia, 2004 Abstract Book, p. 94, Abstract 250.
Klimanskaya Declaration, submitted on Feb. 4, 2010, in the U.S. Appl. No. 11/186,720, pp. 1-5.
Klimanskaya et al., Derivation and comparative assessment of retinal pigment epithelium from human embryonic stem cells using transcriptomics. Cloning and Stem Cells 6:3, 217-245 2004.
Klimanskaya, (2004), Differentiation of hES Cell Lines into Retinal Piment Epithelium-like Cells, Stem Cells, Keystone Symposia, 2004 Abstract Book, p. 94, Abstract 252.
Klimanskaya, (2009), Retinal Pigment Epithelium Derived from Embryonic Stem Cells, in Stem Cell Anthology, Bruce M. Carlson, ed., Academic Press, Chapter 28, pp. 335-346.
Klimanskaya, Derive and conquer: sourcing and differentiating stem cells for therapeutic applications.(2008), Nature Reviews Drug Discovery, 7(2):131-42.
Klimanskaya, Retinal pigment epithelium. (2006), Methods in Enzymology, 418:169-194.
Kniazeva et al., Clinical and genetic studies of an autosomal dominant cone-rod dystrophy with features of Stargardt disease. Ophthalmic Genet. Jun. 1999;20(2):71-81.
Kohen et al., Mechanisms of graft rejection in the transplantation of retinal pigment epithelial cells. Ophthalmic Res. 1997;29(5):298-304. Abstract only.
Lappas et al., Iris pigment epithelial cell translocation in exudative age-related macular degeneration. A pilot study in patients. Graefes Arch Clin Exp Ophthalmol. Aug. 2000;238(8):631-41. Abstract Only.
Lawrence, Schwann cell grafting into the retina of the dystrophic RCS rat limits functional deterioration. Royal College of Surgeons. (2000), Invest., Ophthalmol., & Vis. Sci., 41(2):518-528.
Ledesma et al., Proteins of Bovine Serum. J Anim Sci. 1968;27(5): 1368-1372. http://www.journalofanimalscience.org/content/27/5/1368 [last accessed Jun. 19, 2014].
Lee et al., Spatial cues for the enhancement of retinal pigment epithelial cell function in potential transplants. Biomaterials. Apr. 2007;28(13):2192-201. Epub Jan. 11, 2007. Abstract only.
Liao et al., Molecular signature of primary retinal pigment epithelium and stem-cell-derived RPE cells. Hum Mol Genet. Nov. 1, 2010;19(21):4229-38. doi: 10.1093/hmg/ddq341. Epub Aug. 13, 2010.
Liu et al., Integrated analysis of DNA methylation and RNA transcriptome during in vitro differentiation of human pluripotent stem cells into retinal pigment epithelial cells. PLoS One. Mar. 17, 2014;9(3):e91416. doi:10.1371/journal.pone.0091416. eCollection 2014.
Lu et al., Expression of melanin-related genes in cultured adult human retinal pigment epithelium and uveal melanoma cells. Mol Vis. Nov. 3, 2007;13:2066-72.
Lu et al., Long-term safety and function of RPE from human embryonic stem cells in preclinical models of macular degeneration. Stem Cells. Sep. 2009;27(9):2126-35. doi: 10.1002/stem.149.
Lund et al. Cell Transplantation as a Treatment for Retinal Disease, Progress in Retinal and Eye Research, vol. 20, No. 4, Jul. 2001, pp. 415-449.
Lund et al. Human embryonic stem cell-derived cells rescue visual function in dystrophic RCS rats, Cloning and Stem Cells 8:3, 189-199, 2006.
Lund et al., Subretinal transplantation of genetically modified human cell lines attenuates loss of visual function in dystrophic rats. Proc Natl Acad Sci U S A. Aug. 14, 2001;98(17):9942-7.
MacLaren et al., Autologous transplantation of the retinal pigment epithelium and choroid in the treatment of neovascular age-related macular degeneration. Ophthalmology. Mar. 2007;114(3):561-70. Abstract only.
MacLaren et al., Long-term results of submacular surgery combined with macular translocation of the retinal pigment epithelium in neovascular age-related macular degeneration. Ophthalmology. Dec. 2005;112(12):2081-7. Abstract Only.
Maherali et al., Directly reprogrammed fibroblasts show global epigenetic remodeling and widespread tissue contribution. Cell Stem Cell. Jun. 1, 2007;(1): 55-70.
Marmostein et al., Bestrophin, the product of the Best vitelliform macular dystrophy gene (VMD2), localizes to the basolateral plasma membrane of the retinal pigment epithelium, Proc Natl Acad Sci U S A, Nov. 7, 2000;97(23):12758-63.
Maminishkis et al., Confluent monolayers of cultured human fetal retinal pigment epithelium exhibit morphology and physiology of native tissue. Invest Ophthalmol Vis Sci. Aug. 2006;47(8):3612-24.
Mayerson et al., An improved method for isolation and culture of rate retinal pigment epithelial cells, Invest. Ophthalmol and Vis. Sci. 1985;26:1599-1609.
Motohashi et al. Induction of melanocytes from embryonic stem cells and their therapeutic potential. Pigment Cell Res. Aug. 2006;19(4):284-9.
Muotri, Development of functional human embryonic stem cell-derived neurons in mouse brain. (2005), PNAS, 102(51):18644-18648.
Ohno-Matsui et al., Mol Vis. Aug. 29, 2006;12:1022-32. In vitro and in vivo characterization of iris pigment epithelial cells cultured on amniotic membranes.
Ooto et al., Induction of the Differentiation of Lentoids from Primate Embryonic Stem Cells, Investigative Opthamology & Visual Science, Association for Research in Vision and Opthamology, vol. 44, No. 6, Jun. 2003, pp. 2689-2693.
Opas et al., Formation of retinal pigment epithelium in vitro by transdifferentiation of neural retina cells. Int J Dev Biol. Jun. 2001;45(4):633-42.
Park, In vitro and in vivo analyses of human embryonic stem cell-derived dopamine neurons. (2005), J. Neurochem., 92:1265-1276.
Radtke et al., Vision change after sheet transplant of fetal retina with retinal pigment epithelium to a patient with retinitis pigmentosa. Arch Ophthalmol. Aug. 2004;122(8):1159-65.
Radtke et al., Vision improvement in retinal degeneration patients by implantation of retina together with retinal pigment epithelium. Am J Ophthalmol. Aug. 2008;146(2):172-182. doi:10.1016/j.ajo.2008.04.009. Epub Jun. 10, 2008.
Ray et al., SV40 T antigen alone drives karyotype instability that precedes neoplastic transformation of human diploid fibroblasts. J Cell Biochem. Jan. 1990;42(1):13-31.

(56) References Cited

OTHER PUBLICATIONS

Reubinoff et al., Embryonic Stem Cell Lines From Human Blastocysts: Somatic Differentiation in Vitro, Nature Biotechnology, Nature Publishing Group, New York, NY, vol. 18, No. 4, Apr. 2000, pp. 399-404.

Sauvé et al., Visual field loss in RCS rats and the effect of RPE cell transplantation. Exp Neurol. Aug. 1998;152(2):243-50. Abstract only.

Sauve et al., Preservation of visual responsiveness in the superior colliculus of RCS rats after retinal pigment epithelium cell transplantation. Neuroscience. 2002;114(2):389-401.

Schraermeyer et al., 2001, Subretinally Transplanted Embryonic Stem Cell Rescue Photoreceptor Cells From Degeneration in the RCS Rats, Cell Transplantation, 10:673-680.

Schuldiner et al., Effects of eight growth factors on the differentiation of cells derived from human embryonic stem cells, Proc Natl Acad Sci U S A, Oct. 10, 2000;97(21):11307-12.

Schwartz, Embryonic stem cell trials for macular degeneration: a preliminary report The Lancet, vol. 379, Issue 9817, pp. 713-720. (http://dx.doi.org/10.1016/50140-6736(12)60028-2, available online Jan. 24, 2012).

Skottman, Unique gene expression signature by human embryonic stem cells cultured under serum-free conditions correlates with their enhanced and prolonged growth in an undifferentiated stage. (2006), Stem Cells, 24(1):151-67.

Song et al., Propagation of fetal human RPE cells: preservation of original culture morphology after serial passage. J Cell Physiol. Apr. 1990;143(1):196-203. Abstract Only.

Sparrow et al., The retinal pigment epithelium in health and disease. Curr Mol Med. Dec. 2010;10(9):802-23. Abstract Only.

Stanga et al., Retinal pigment epithelium translocation after choroidal neovascular membrane removal in age-related macular degeneration. Ophthalmology. Aug. 2002;109(8):1492-8. Abstract.

Strauss, The retinal pigment epithelium in visual function. Physiol Rev. Jul. 2005;85(3):845-81.

Subramanian, Cell transplantation for the treatment of Parkinson's disease. (2001), Seminars Neurol 21(1):103-115.

Sugino et al., Comparison of FRPE and human embryonic stem cell-derived RPE behavior on aged human Bruch's membrane. Invest Ophthalmol Vis Sci. Jul. 1, 2011;52(8):4979-97. doi:.10.1167/iovs.10-5386.

Takahashi, (2003), Regenerative medicine in eye diseases, Geriatric Medicine, 41(12):1791-1795.

Takahashi, Nihon Saisei-Iryo Gakkai zasshi, 2004; 3(2):76-80.

Talecris Biotherapeutics, Plasmanate Product Information Sheet, retrieved from http://www.bdipharma.com/Package%20Insert/Talecris/Plasmanate.sub.---01-2005.pdf (last visited Jan. 6, 2011).

Tamai, [Retinal pigment epithelial cell transplantation: perspective]. Nihon Ganka Gakkai Zasshi. Dec. 1996;100(12):982-1006.

Tezel et al., Adult retinal pigment epithelial transplantation in exudative age-related macular degeneration. Am J Ophthalmol Apr. 2007;143(4):584-95. Epub Feb. 14, 2007. Abstract Only.

Tezel et al., Serum-free media for culturing and serial-passaging of adult human retinal pigment epithelium. Exp Eye Res. Jun. 1998;66(6):807-15.

Thumann et al., Transplantation of autologous iris pigment epithelium after removal of choroidal neovascular membranes. Arch Ophthalmol Oct. 2000;118(10):1350-5.

Tian et al., The expression of native and cultured RPE grown on different matrices. Physiol Genomics. Apr. 13, 2004;17(2):170-82. Abstract only.

Timar et al., Angiogenesis-Dependent Diseases and Angiogenesis Therapy. Pathol Oncol Res. 2001;7(2):85-94.

Treumer et al., Autologous retinal pigment epithelium-choroid sheet transplantation in age related macular degeneration: morphological and functional results. Br J Ophthalmol. Mar. 2007;91(3):349-53. Epub Oct. 11, 2006.

Valtink et al., Culturing of Retinal Pigment Epithelium Cells, Eye Banking. Dev Ophthalmol. Basel, Karger, 2009, vol. 43, pp. 109-119.

Van Meurs et al., Br J Ophthalmol. Jan. 2004;88(1):110-3. Autologous peripheral retinal pigment epithelium translocation in patients with subfoveal neovascular membranes.

Verfaillie, Stem Cells: Hype and Reality, Hematology Am Soc Hematol Ethic Program. 2002:369-81.

Villegas-Pérez et al., Ganglion cell loss in RCS rat retina: a result of compression of axons by contracting intraretinal vessels linked to the pigment epithelium. J Comp Neurol. Mar. 2, 1998;392(1):58-77. Abstract only.

Wang et al., Grafting of ARPE-19 and Schwann cells to the subretinal space in RCS rats. Invest Ophthalmol Vis Sci. Jul. 2005;46(7):2552-60.

Wang et al., Transplantation of reprogrammed embryonic stem cells improves visual function in a mouse model for retinitis pigmentosa. Transplantation. Apr. 27, 2010;89(8):911-9. doi: 10.1097/TP.0b013e3181d45a61.

Weisz et al., Allogenic fetal retinal pigment epithelial cell transplant in a patient with geographic atrophy, Retina. 1999;19(6):540-5.

Wichterle, Directed differentiation of embryonic stem cells into motor neurons. (2002), Cell, 110:385-397.

Yang, Roles of cell-extrinsic growth factors in vertebrate eye pattern formation and retinogenesis. (2004), Semin Cell Dev Biol., 15:91-103.

Ying et al. Conversion of Embryonic Stem Cells Into Neuroctodermal Precursors in Adherent Monoculture, Nature Biotechnology, Nature Publishing Group, New York, NY, vol. 21, No. 2, Feb. 2003, pp. 183-186.

Zaghloul et al., Step-wise specification of retinal stem cells during normal embryogenesis, Biol Cell, May 2005 ;97(5):321-37.

Zeng, Dopaminergic differentiation of human embryonic stem cells. (2004), Stem Cell, 22:925-940.

Zhang et al., In vitro differentiation of transplantable neural precursors from human embryonic stem cells, Nat Biotechnol., Dec. 2001;19(12):1129-33.

Zhao et al. Differentiation of Embryonic Stem Cells Into Retinal Neurons, Biochemical and Biophysical Research Communications, vol. 297, No. 2, Sep. 2002, pp. 177-184.

Zhao, Differentiation and transdifferentiation of the retinal pigment epithelium. (1997), International Rev. Cytology, 171:225-266.

Zhao, in vitro transdifferentiation of embryonic rat retinal pigment epithelium to neural retina. (1995), Brain Res., 677:300-310.

Armstrong, UK House Parliaments' Select Committee on Science and Technology, Fifth Report of Session. Jul. 2006. Apr. 5, 2007; vol. II: 76-80.

Aronson, Human retinal pigment cell culture. In Vitro. 1983 Aug;19(8):642-50.

Boulton, Studying melanin and lipofuscin in RPE cell culture models. Exp Eye Res. Sep. 2014;126:61-7.

Chawengsaksophak et al., Cdx2 is essential for axial elongation in mouse development. Proc Natl Acad Sci U S A. May 18, 2004;101(20):7641-5. Epub May 10, 2004.

Cibelli et al., Somatic cell nuclear transfer in humans: pronuclear and early embryonic development. E-Biomed. Nov. 26, 2001:2(5):25-31.

Cursiefen et al., Chapter 5: Special Anatomy and Pathology in Intraocular Microsurgery, Cornea and Limbus. In Applied Pathology for Ophthalmic Microsurgeons, Eds. Naumann et al. Springer-Verlag Berlin Heidelberg. 2008;97-349.

Dominiguez-Bendala et al., Handbook of Stem Cells, Chapter 70: Islet Cell Therapy and Pancreatic Stem Cells. 2013:835-53.

Fukui et al., ABCA4 gene mutations in Japanese patients with Stargardt disease and retinitis pigmentosa. Invest Ophthalmol Vis Sci. Sep. 2002;43(9):2819-24.

Hurlbut et al., Altered nuclear transfer as a morally acceptable means for the procurement of human embryonic stem cells. Perspect Biol Med. 2005 Spring;48(2):211-28.

Kaplan et al., Retinal transplantation. Chem Immunol. 1999;73:207-19.

Kindzelskii et al., Toll-like receptor 4 (TLR4) of retinal pigment epithelial cells participates in transmembrane signaling in response to photoreceptor outer segments. J Gen Physiol. Aug. 2004;124(2):139-49.

Kuznetsova et al., Cell and Tissue Biology. 2011;5(5):495-502.

(56) References Cited

OTHER PUBLICATIONS

Lai et al., SRY (sex determining region Y)-box2 (Sox2)/poly ADP-ribose polymerase 1 (Parp1) complexes regulate pluripotency. Proc Natl Acad Sci U S A. Mar. 6, 2012;109(10):3772-7. doi: 10.1073/pnas.1108595109. Epub Feb. 23, 2012.
Lin et al., Multilineage potential of homozygous stem cells derived from metaphase II oocytes. Stem Cells. 2003;21(2):152-61.
Little et al., Transplantation of human fetal retinal pigment epithelium rescues photoreceptor cells from degeneration in the Royal College of Surgeons rat retina. Invest Ophthalmol Vis Sci. Jan. 1996;37(1):204-11.
Lu et al., Generation of functnal hemangioblasts from human embryonic stem cells, Nature Methods, vol. 4 No. 6, Jun. 2007, 501-509.
Ma, Identification of RPE65 in transformed kidney cells. (1999), FEBS Lett., 452(3):199-204.
Mitalipova et al., Human embryonic stem cell lines derived from discarded embryos. Stem Cells. 2003;21(5):521-6.
Peyman et al., A technique for retinal pigment epithelium transplantation for age-related macular degeneration secondary to extensive subfoveal scarring. Ophthalmic Surg. Feb. 1991;22(2):102-8.
Proulx et al., Integrin alpha5 expression by the ARPE-19 cell line: comparison with primary RPE cultures and effect of growth medium on the alpha5 gene promoter strength. Exp Eye Res. Aug. 2004;79(2):157-65.
Prusa et al., Oct-4-expressing cells in human amniotic fluid: a new source for stem cell research? Hum Reprod. Jul. 2003;18(7):1489-93.
Revazova et al., Patient-specific stem cell lines derived from human parthenogenetic blastocysts. Cloning Stem Cells. 2007 Fall;9(3):432-49.
Rogers et al., Phospholipase Czeta causes Ca2+ oscillations and parthenogenetic activation of human oocytes. Reproduction. Dec. 2004;128(6):697-702.
Schwartz et al., Human embryonic stem cell-derived retinal pigment epithelium in patients with age-related macular degeneration and Stargardt's macular dystrophy: follow-up of two open-label phase 1/2 studies. Lancet. Oct. 15, 2014. pii: S0140-6736(14)61376-3. doi: 10.1016/S0140-6736(14)61376-3. [Epub ahead of print].
Shamblott et al., Derivation of pluripotent stem cells from cultured human primordial germ cells. Proc Natl Acad Sci U S A. Nov. 10, 1998;95(23):13726-31.
Shmookler et al., Variability of DNA methylation patterns during serial passage of human diploid fibroblasts. Proc Natl Acad Sci U S A. Jul. 1982;79(13):3949-53.
Thomson et al. Embryonic Stem Cell Lines Derived from Human Blastocysts, Science, American Association for the Advancement of Science, Washington DC, vol. 282, Nov. 1998, pp. 1145-1147.
Thomson, Pluripotent cell lines derived from common marmoset (*Callithrix jacchus*) blastocysts. (1996), Biol. Reprod., 55:254-259.
Tuschl, Effects of cell culture conditions on primary rat hepatocytes-cell morphology and differential gene expression. Toxicology. Feb. 1, 2006;218(2-3):205-15. Epub Dec. 6, 2005.
Vugler et al., Elucidating the phenomenon of HESC-derived RPE: anatomy of cell genesis, expansion and retinal transplantation. Exp Neurol. Dec. 2008;214(2):347-61. doi: 10.1016/j.expneurol.2008.09.007. Epub Sep. 27, 2008.
Yu et al., Induced pluripotent stem cell lines derived from human somatic cells. Science. Dec. 21, 2007;318(5858):1917-20. Epub Nov. 20, 2007.
Zhu et al., Isolation, culture and characteristics of human foetal and adult retinal pigment epithelium. Aust N Z J Ophthalmol. May 1998;26 Suppl 1:S50-2.
Zhou et al. Novel PAX6 binding sites in the human genome and the role of repetitive elements in the evolution of gene regulation. Genome Res. Nov. 2002;12(11):1716-22.
Znoiko, Identification of the RPE65 protein in mammalian cone photoreceptors. (2002), Invest Ophthalmol Vis Sci., 43(5):1604-9.
Zwaka et al., A germ cell origin of embryonic stem cells? Development. Jan. 2005;132(2):227-33.
[No Author Listed] Research Committee on Chorioretinal Degeneration and Optic Atrophy. The Ministry of Health, Labour and Welfare of Japan. 2002. 132-140.
Flood et al., Growth characteristics and ultrastructure of human retinal pigment epithelium in vitro. Invest Ophthalmol Vis Sci. Nov. 1980;19(11):1309-20.
Osakada et al., Toward the generation of rod and cone photoreceptors from mouse, monkey and human embryonic stem cells. Nat Biotechnol. Feb. 2008;26(2):215-24. doi: 10,1038/nbt1384. Epub Feb. 3, 2008.
Zheng et al., Involvement of rho-kinase pathway in contractile activity of rabbit RPE cells in vivo and in vitro, Invest Ophthalmol Vis Sci. Feb. 2004;45(2):668-74.
[No Author Listed] Center for veterinary medicine program policy and procedures manual. Sterility and pyrogen requirements for injectable drug products. Apr. 25, 2000. Guide 1240.4122. 5 pages.
[No Author Listed] Medium System for MDBK Cells. Sigma Product Nos. M 3553 and M 0682. Product Information sheet. Sigma®. Sigma-Aldrich, Inc. May 29, 2003. 2 pages.
Basak et al., Human embryonic stem cells hemangioblast express HLA-antigens. J Transl Med. Apr. 2009;7:27.
Liu et al., A novel chemical-defined medium with bFGF and N2B27 supplements supports undifferentiated growth in human embryonic stem cells. Biochem Biophys Res Commun. Jul. 21, 2006;346(1):131-9. Epub May 24, 2006.
Mitalipov et al., Isolation and characterization of novel rhesus monkey embryonic stem cell lines. Stem Cells. Oct. 2006;24(10):2177-86. Epub Jun. 1, 2006.
Murisier et al., Genetics of pigment cells: lessons from the tyrosinase gene family. Histol Histopathol. 2006;21:567-78.
Pedersen, Studies of in vitro differentiation with embryonic stem cells. Reprod Fertil Dev. 1994;6(5):543-52.
Rogojina et al., Comparing the use of Affymetrix to spotted oligonucleotide microarrays using two retinal pigment epithelium cell lines. Mol Vis. Oct. 6, 2003;9:482-96.
Schulz et al., Directed neuronal differentiation of human embryonic stem cells. BMC Neurosci. Oct. 22, 2003;4:27.
Svendsen et al., Increased survival of rat EGF-generated CNS precursor cells using B27 supplemented medium. Exp Brain Res. 1995;102(3):407-14.
Wang et al., Advances on in vitro induced differentiation of embryonic stem cells into melanocytes. J Tissue Eng Reconstr Surg. Oct. 2008;4(5):292-4. Chinese language reference.
Wistow et al., Expressed sequence tag analysis of human RPE/choroid for the NEIBank Project: over 6000 non-redundant transcripts, novel genes and splice variants. Mol Vis. Jun. 15, 2002;8:205-20. http://www.molvis.org/molvis/v8/a27/.

* cited by examiner

US 10,077,424 B2

METHODS OF PRODUCING RPE CELLS AND COMPOSITIONS OF RPE CELLS

RELATED APPLICATIONS

This application is a continuation of U.S. application Ser. No. 12/682,712, filed Dec. 14, 2010, currently pending, which is a national stage filing under 35 U.S.C. § 371 of International Application No. PCT/US2008/011669, filed Oct. 10, 2008, which was published under PCT Article 21(2) in English, and which claims the benefit of priority to U. S. provisional application Nos. 60/998,766, filed Oct. 12, 2007, 60/998,668, filed Oct. 12, 2007, 61/009,908, filed Jan. 2, 2008, and 61/009,911, filed Jan. 2, 2008. The disclosures of each of the foregoing applications are hereby incorporated by reference in their entirety.

BACKGROUND OF THE INVENTION

The retinal pigment epithelium (RPE) is the pigmented cell layer just outside the neurosensory retina. This layer of cells nourishes retinal visual cells, and is attached to the underlying choroid (the layer of blood vessels behind the retina) and overlying retinal visual cells. The RPE acts as a filter to determine what nutrients reach the retina from the choroid. Additionally, the RPE provides insulation between the retina and the choroid. Breakdown of the RPE interferes with the metabolism of the retina, causing thinning of the retina. Thinning of the retina can have serious consequences. For example, thinning of the retina may cause "dry" macular degeneration and may also lead to the inappropriate blood vessel formation that can cause "wet" macular degeneration).

Given the importance of the RPE in maintaining visual and retinal health, there have been significant efforts in studying the RPE and in developing methodologies for producing RPE cells in vitro. RPE cells produced in vitro could be used to study the developments of the RPE, to identify factors that cause the RPE to breakdown, or to identify agents that can be used to stimulate repair of endogenous RPE cells. Additionally, RPE cells produced in vitro could themselves be used as a therapy for replacing or restoring all or a portion of a patient's damaged RPE cells. When used in this manner, RPE cells may provide an approach to treat macular degeneration, as well as other diseases and conditions caused, in whole or in part, by damage to the RPE.

The use of RPE cells produced in vitro for screening or as a therapeutic relies on methods that can be used to produce large numbers of RPE cells in a systematic, directed manner. Such systematized differentiation methods would provide significant advantages over previous schemes based on, for example, spontaneous differentiation of RPE cells from transformed cell lines or other sources.

SUMMARY OF THE INVENTION

The present invention provides a method for differentiating RPE cells from human pluripotent stem cells, such as human embryonic stem cells and human induced pluripotent stem cells. The method is used to produce large numbers of differentiated RPE cells for use in screening assays, to study the basic biology of the RPE, and as therapeutics. As described herein, RPE cells differentiated from pluripotent stem cells, such as human embryonic stem cells, using this approach are molecularly distinct from human embryonic stem cells, as well as from adult and fetal-derived RPE cells.

The present invention also provides preparations and pharmaceutical preparations of RPE cells derived from human pluripotent stem cells. Such RPE cell preparations are molecularly distinct from human embryonic stem cells, as well as from adult and fetal-derived RPE cells.

The present invention provides, for the first time, a detailed molecular characterization of RPE cells differentiated from human embryonic stem cells. The detailed characterization includes comparisons to RPE cells derived from other sources (e.g., adult RPE cells and fetal RPE cells), as well as to human embryonic stem cells. This analysis not only provides a deeper understanding of RPE cells, but it also revealed that RPE cells differentiated from human embryonic stem cells have distinct molecular properties that distinguish these cells from previously described RPE cells.

The present invention provides preparations of RPE cells, including substantially purified preparations of RPE cells. Exemplary RPE cells are differentiated from human pluripotent stem cells, such as human embryonic stem cells or iPS cells. Human pluripotent stem cell-derived RPE cells can be formulated and used to treat retinal degenerative diseases. Additionally, human pluripotent stem cell-derived RPE cells can be used in screening assays to identify agents that modulate RPE cell survival (in vitro and/or in vivo), to study RPE cell maturation, or to identify agents that modulate RPE cell maturation. Agents identified using such screening assays may be used in vitro or in vivo and may provide additional therapeutics that can be used alone or in combination with RPE cells to treat retinal degenerative diseases.

The present invention provides improved methods for the production of RPE cells from embryonic stem cells or other pluripotent stem cells. The methods of the invention can be used to produce differentiated RPE cells. Optionally, the level of maturation, as assessed by pigmentation levels, of the differentiated RPE cells can be modulated so that differentiated RPE cells, mature RPE cells, or mixtures thereof are produced. Also provided are improved methods for the treatment of eye disorders. In particular, these methods involve the use of RPE cells derived from human embryonic stem cells to treat or ameliorate the symptoms of eye disorders, particularly eye disorders caused or exacerbated, in whole or in part, by damage to or breakdown of the endogenous RPE layer.

In certain aspects, the invention provides a method for producing a culture of retinal pigment epithelial (RPE) cells. In certain embodiments, the culture is a substantially purified culture containing at least 75%, 80%, 85%, 90%, 91%, 92%, 93%, 94%, 95%, 96%, 97%, 98%, 99%, or greater than 99% differentiated RPE cells (at least 75% of the culture is a differentiated RPE cell, regardless of level of maturity). In certain embodiments, the substantially purified culture contains at least 30%, 35%, 40% or 45% mature differentiated RPE cells. In certain embodiments, the substantially purified culture contains at least 50% mature differentiated RPE cells. In other embodiments, the substantially purified culture contains at least 55%, 60%, 65%, 70%, 75%, 80%, 85%, 90%, 91%, 92%, 93%, 94%, 95%, 96%, 97%, 98%, 99%, or greater than 99% mature differentiated RPE cells. In certain embodiments, the differentiated RPE cells are derived from human embryonic stem cells, human iPS cells, or other pluripotent stem cells.

In certain embodiments, the method comprising the steps of a) providing human embryonic stem cells;

b) culturing the human embryonic stem cells as embryoid bodies in nutrient rich, low protein medium, which medium optionally contains serum free B-27 supplement;

c) culturing the embryoid bodies as an adherent culture in nutrient rich, low protein medium, which medium optionally contains serum free B-27 supplement;

d) culturing the adherent culture of cells of (c) in nutrient rich, low protein medium, which medium does not contain serum free B-27 supplement;

e) culturing the cells of (d) in medium capable of supporting growth of high-density somatic cell culture, whereby RPE cells appear in the culture of cells:

f) contacting the culture of (e) with an enzyme;

g) selecting the RPE cells from the culture and transferring the RPE cells to a separate culture containing medium supplemented with a growth factor to produce an enriched culture of RPE cells; and h) propagating the enriched culture of RPE cells to produce a substantially purified culture of RPE cells.

In certain other aspects, the invention provides a method of producing a mature retinal pigment epithelial (RPE) cell, said method comprising the steps of a) providing human embryonic stem cells;

b) culturing the human embryonic stem cells as embryoid bodies in nutrient rich, low protein medium, which medium optionally contains serum free B-27 supplement;

c) culturing the embryoid bodies as an adherent culture in nutrient rich, low protein medium, which medium optionally contains serum free B-27 supplement;

d) culturing the adherent culture of cells of step (c) in nutrient rich, low protein medium, which medium does not contain serum free B-27 supplement;

e) culturing the cells of (d) in medium capable of supporting growth of high-density somatic cell culture, whereby RPE cells appear in the culture of cells f) contacting the culture of (e) with an enzyme;

g) selecting the RPE cells from the culture and transferring the RPE cells to a separate culture containing medium supplemented with a growth factor to produce an enriched culture of RPE cells;

h) propagating the enriched culture of RPE cells; and i) culturing the enriched culture of RPE cells to produce mature RPE cells.

In certain embodiments of any of the foregoing, the substantially purified culture of RPE cells may contain both differentiated RPE cells and mature differentiated RPE cells. Amongst the mature RPE cells, the level of pigment may vary. However, the mature RPE cells can be distinguished visually from the RPE cells based on the increased level of pigmentation and the more columnar shape.

In certain embodiments, the percentage of mature differentiated RPE cells in the culture can be reduced by decreasing the density of the culture. Thus, in certain embodiments, the method further comprises subculturing a population of mature RPE cells to produce a culture containing a smaller percentage of mature RPE cells.

In certain embodiments, the medium used when culturing the cells as embryoid bodies may be selected from any medium appropriate for culturing cells as embryoid bodies. For example, one of skill in the art can select amongst commercially available or proprietary media. Any medium that is capable of supporting high-density cultures may be used, such as medium for viral, bacterial, or eukaryotic cell culture. For example, the medium may be high nutrient, protein-free medium or high nutrient, low protein medium. For example, the human embryonic stem cells may be cultured in MDBK-GM, OptiPro SFM, VP-SFM, EGM-2, or MDBK-MM. In certain embodiments the medium may also contain B-27 supplement.

In certain embodiments, the medium described herein may also be supplemented with one or more growth factors. Growth factors that may be used include, for example, EGF, bFGF, VEGF, and recombinant insulin-like growth factor.

The medium may also contain supplements such as heparin, hydrocortisone, ascorbic acid, serum (such as, for example, fetal bovine serum), or a growth matrix (such as, for example, extracellular matrix from bovine corneal epithelium, matrigel (BD biosciences), or gelatin).

In certain embodiments, mechanical or enzymatic methods are used to select RPE cells from amongst clusters of non-RPE cells in a culture of embryoid body, or to facilitate sub-culture of adherent cells. Exemplary mechanical methods include, but are not limited to, tituration with a pipette or cutting with a pulled needle. Exemplary enzymatic methods include, but are not limited to, any enzymes appropriate for disassociating cells (e.g., trypsin, collagenase, dispase). In certain embodiments, a non-enzymatic solution is used to disassociate the cells, such as a high EDTA-containing solution such as, for example, Hanks-based cell disassociation buffer.

In certain embodiments, for any of the above articulated steps, the cells are cultured for between about 3 days and 45 days, such as 7 days, 7-10 days, 7-14 days, or 14-21 days. In certain embodiments the cells are cultured for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or about 46 days. In certain embodiments, the cells are cultured for less than or equal to about: 45, 40, 35, 30, 25, 21, 20, 18, 15, 14, 13, 12, 11, 10, 9, 8, 7, 6, 5, 4, 3, 2, or 1 days. Note that, for each of the above articulated method steps, the cells may be cultured for the same period of time at each step or for differing periods of time at one or more of the steps.

In certain embodiments, the RPE cells are further cultured to produce a culture of mature RPE cells. Both RPE cells and mature RPE cells are differentiated RPE cells. However, mature RPE cells are characterized by increased level of pigment in comparison to differentiated RPE cells. The level of maturity and pigmentation can be modulated by increasing or decreasing the density of the culture of differentiated RPE cells. Thus, a culture of RPE cells can be further cultured to produce mature RPE cells. Alternatively, the density of a culture containing mature RPE cells can be decreased to decrease the percentage of mature differentiated RPE cells and increase the percentage of differentiated RPE cells.

The medium used to culture the RPE cells is any medium appropriate for cell culture, and can be selected by the skilled person. For example, any medium that is capable of supporting high-density cultures may be used, such as medium for viral, bacterial, or animal cell culture. For example, the cells described herein may be cultured in VP-SFM, EGM-2, and MDBK-MM.

In certain embodiments of any of the foregoing, said substantially purified culture of RPE cells (with or without mature RPE cells) are frozen for storage. The cells may be stored by any appropriate method known in the art, e.g., cryogenically frozen and may be frozen at any temperature appropriate for storage of the cells. For example, the cells may be frozen at approximately −20° C., −80° C., −120° C., or at any other temperature appropriate for storage of cells. Cryogenically frozen cells are stored in appropriate containers and prepared for storage to reduce risk of cell damage and maximize the likelihood that the cells will survive thawing. In other embodiments, RPE cells are maintained at room temperature, or refrigerated at, for example, approximately 4° C.

In certain embodiments of any of the foregoing, the method is performed in accordance with Good Manufacturing Practices (GMP). In certain embodiments of any of the foregoing, the human embryonic stem cells from which the RPE cells are differentiated were derived in accordance with Good Manufacturing Practices (GMP). In certain embodiments of any of the foregoing, the human embryonic stem cells from which the RPE cells are differentiated were derived from one or more blastomeres removed from an early stage embryo without destroying the remaining embryo.

In certain embodiments of any of the foregoing, the method is used to produce a preparation comprising at least $1\times10^5$ RPE cells, at least $5\times10^5$ RPE cells, at least $1\times10^6$ RPE cells, at least $5\times10^6$ RPE cells, at least $1\times10^7$ RPE cells, at least $2\times10^7$ RPE cells, at least $3\times10^7$ RPE cells, at least $4\times10^7$ RPE cells, at least $5\times10^7$ RPE cells, at least $6\times10^7$ RPE cells, at least $7\times10^7$ RPE cells, at least $8\times10^7$ RPE cells, at least $9\times10^7$ RPE cells, at least $1\times10^8$ RPE cells, at least $2\times10^8$ RPE cells, at least $5\times10^8$ RPE cells, at least $7\times10^8$ RPE cells, or at least $1\times10^9$ RPE cells. In certain embodiments, the number of RPE cells in the preparation includes differentiated RPE cells, regardless of level of maturity and regardless of the relative percentages of differentiated RPE cells and mature RPE cells. In other embodiments, the number of RPE cells in the preparation refers to the number of either differentiated RPE cells or mature RPE cells.

In certain embodiments, the method further comprises formulating the differentiated RPE cells and/or differentiated mature RPE cells to produce a preparation of RPE cells suitable for transplantation.

In another aspect, the invention provides a method for treating or preventing a condition characterized by retinal degeneration, comprising administering to a subject in need thereof an effective amount of a preparation comprising RPE cells, which RPE cells are derived from human embryonic stem cells, iPS cells, or other pluripotent stem cells. Conditions characterized by retinal degeneration include, for example, Stargardt's macular dystrophy, age related macular degeneration (dry or wet), diabetic retinopathy, and retinitis pigmentosa. In certain embodiments, the RPE cells are derived from human pluripotent stem cells using one or more of the methods described herein.

In certain embodiments, the preparation was previously cryopreserved and was thawed before transplantation.

In certain embodiments, the method of treating further comprises administration of cyclosporin or one or more other immunosuppressants. When immunosuppressants are used, they may be administered systemically or locally, and they may be administered prior to, concomitantly with, or following administration of the RPE cells. In certain embodiments, immunosuppressive therapy continues for weeks, months, years, or indefinitely following administration of RPE cells.

In certain embodiments, the method of treatment comprises administration of a single dose of RPE cells. In other embodiments, the method of treatment comprises a course of therapy where RPE cells are administered multiple times over some period. Exemplary courses of treatment may comprise weekly, biweekly, monthly, quarterly, biannually, or yearly treatments. Alternatively, treatment may proceed in phases whereby multiple doses are required initially (e.g., daily doses for the first week), and subsequently fewer and less frequent doses are needed. Numerous treatment regimens are contemplated.

In certain embodiments, the administered RPE cells comprise a mixed population of differentiated RPE cells and mature RPE cells. In other embodiments, the administered RPE cells comprise a substantially purified population of either differentiated RPE cells or mature RPE cells. For example, the administered RPE cells may contain less than 25%, 20%, 15%, 10%, 9%, 8%, 7%, 6%, 5%, 4%, 3%, 2%, or less than 1% of the other RPE cell-type.

In certain embodiments, the RPE cells are formulated in a pharmaceutically acceptable carrier or excipient.

In certain embodiments, the preparation comprising RPE cells is transplanted in a suspension, matrix or substrate. In certain embodiments, the preparation is administered by injection into the subretinal space of the eye. In certain embodiments, about $10^4$ to about $10^6$ cells are administered to the subject. In certain embodiments, the method further comprises the step of monitoring the efficacy of treatment or prevention by measuring electroretinogram responses, optomotor acuity threshold, or luminance threshold in the subject. The method may also comprise monitoring the efficacy of treatment or prevention by monitoring immunogenicity of the cells or migration of the cells in the eye.

In certain aspects, the invention provides a pharmaceutical preparation for treating or preventing a condition characterized by retinal degeneration, comprising an effective amount of RPE cells, which RPE cells are derived from human embryonic stem cells or other pluripotent stem cells. The pharmaceutical preparation may be formulated in a pharmaceutically acceptable carrier according to the route of administration. For example, the preparation may be formulated for administration to the subretinal space of the eye. The composition may comprise at least $10^4$, $10^5$, $5\times10^5$, $6\times10^5$, $7\times10^5$, $8\times10^5$, $9\times10^5$, $10^6$, $2\times10^6$, $3\times10^6$, $4\times10^6$, $5\times10^6$, $6\times10^6$, $7\times10^6$, $8\times10^6$, $9\times10^6$, or $10^7$ RPE cells. In certain embodiments, the composition may comprise at least $2\times10^7$, $5\times10^7$, $6\times10^7$, $7\times10^7$, $8\times10^7$, $9\times10^7$, $1\times10^8$ RPE cells. In certain embodiments, the RPE cells may include mature RPE cells, and thus the cell number includes the total of both differentiated RPE cells and mature differentiated RPE cells.

In another aspect, the invention provides a method for screening to identify agents that modulate the survival of RPE cells. For example, RPE cells differentiated from human embryonic stem cells can be used to screen for agents that promote RPE survival. Identified agents can be used, alone or in combination with RPE cells, as part of a treatment regimen. Alternatively, identified agents can be used as part of a culture method to improve the survival of RPE cells differentiated in vitro.

In another aspect, the invention provides a method for screening to identify agents that modulate RPE cell maturity. For example, RPE cells differentiated from human ES cells can be used to screen for agents that promote RPE maturation.

In certain embodiments of any of the foregoing, the method is performed in accordance with Good Manufacturing Practices (GMP). In certain embodiments of any of the foregoing, the human embryonic stem cells or other pluripotent stem cells from which the RPE cells are differentiated were derived in accordance with Good Manufacturing Practices (GMP). In certain embodiments of any of the foregoing, the human embryonic stem cells from which the RPE cells are differentiated were derived from one or more blastomere removed from an early stage embryo without destroying the remaining embryo.

In another aspect, the invention contemplates that, instead of human embryonic stem cells, the starting material for producing RPE cells, or preparations thereof, can be other types of human pluripotent stem cells. By way of example, the invention contemplates that induced pluripotent stem (iPS) cells are used as a starting material for differentiating RPE cells using the methods described herein. Such iPS cells can be obtained from a cell bank, or otherwise previously derived. Alternatively, iPS cells can be newly generated prior to commencing differentiation to RPE cells.

In one embodiment, RPE cells or preparations differentiated from pluripotent stem cells, including iPS cells, are used in a therapeutic method.

The present invention also provides functional human retinal pigmented epithelial cells (hRPEs) that are terminally differentiated from human embryonic stem cells (hESCs) or other human pluripotent stem cells. In non-human, primate transplantation experiments, these hRPEs can be identified apart from other cells by means of their unique physical characteristics, such as by their unique mRNA and protein expression. Moreover, when implanted into a validated animal model of retinal degeneration, hRPEs may treat retinal degeneration in the diseased animal. Accordingly, the hRPEs of the invention are useful for treating patients afflicted by various retinal degenerative disorders. The present invention therefore provides a renewable source of hRPEs that can be produced and manufactured under GLP-like and GMP-compliant conditions for the treatment of visual degenerative diseases and disorders.

In certain embodiments, the present invention provides a human retinal pigmented epithelial cell derived from a human embryonic stem cell, which cell is pigmented and expresses at least one gene that is not expressed in a cell that is not a human retinal pigmented epithelial cell. In certain embodiments, the human retinal pigmented epithelial cell is isolated from at least one protein, molecule, or other impurity that is found in its natural environment.

In another embodiment, the invention provides a cell culture comprising human RPE cells derived from human embryonic stem cells or other pluripotent stem cells, which are pigmented and express at least one gene that is not expressed in a cell that is not a human RPE. When used in this manner, pigmented refers to any level of pigmentation, for example, the pigmentation that initial occurs when RPE cells differentiate from ES cells. Pigmentation may vary with cell density and the maturity of the differentiated RPE cells. However, when cells are referred to as pigmented—the term is understood to refer to any and all levels of pigmentation.

In some embodiments, the cell culture comprises a substantially purified population of human RPE cells. A substantially purified population of hRPE cells is one in which the hRPE cells comprise at least about 75% of the cells in the population. In other embodiments, a substantially purified population of hRPE cells is one in which the hRPE cells comprise at least about 80%, 85%, 90%, 91%, 92%, 93%, 94%, 95%, 96%, 97%, 97.5%, 98%, 99%, or even greater than 99% of the cells in the population. In some embodiments, the pigmentation of the hRPE cells in the cell culture is homogeneous. In other embodiments, the pigmentation of the hRPE cells in the cell culture is heterogeneous, and the culture of RPE cells comprises both differentiated RPE cells and mature RPE cells. A cell culture of the invention may comprise at least about $10^1$, $10^2$, $5\times10^2$, $10^3$, $5\times10^3$, $10^4$, $10^5$, $10^6$, $10^7$, $10^8$, or at least about $10^9$ hRPE cells.

The present invention provides human retinal pigmented epithelial cells with varying degrees of pigmentation. In certain embodiments, the pigmentation of a human retinal pigmented epithelial cell is the same as an average human pigmented epithelial cell after terminal differentiation of the hRPE cell. In certain embodiments, the pigmentation of a human retinal pigmented epithelial cell is more pigmented than the average human retinal pigmented epithelial cell after terminal differentiation of the hRPE cell. In certain other embodiments, the pigmentation of a human retinal pigmented epithelial cell is less pigmented than the average human retinal pigmented epithelial cell after terminal differentiation.

In certain embodiments, the present invention provides human RPE cells differentiated from ES cells or other pluripotent stem cells and that express (at the mRNA and/or protein level) one or more (1, 2, 3, 4, 5, or 6) of the following: RPE-65, Bestrophin, PEDF, CRALBP, Otx2, and Mit-F. In certain embodiments, gene expression is measured by mRNA expression. In other embodiments, gene expression is measured by protein expression. In certain embodiments, the RPE cells do not substantially express ES-specific genes, such as Oct-4, alkaline phosphatase, nanog, and/or Rex-1. In other embodiments, the RPE cells express one or more (1, 2, or 3) of pax-2, pax-6, and/or tyrosinase. In certain embodiments, expression of pax-2, pax-6, and/or tyrosinase distinguishes differentiated RPE cells from mature differentiated RPE cells. In other embodiments, the RPE cells express one or more of the markers presented in Table 2, and the expression of the one or more markers is upregulated in RPE cells relative to expression (if any) in human ES cells. In other embodiments, the RPE cells express one or more of the markers presented in Table 3, and the expression of the one or more markers is downregulated in RPE cells relative to expression (if any) in human ES cells.

In certain embodiments, the invention provides a pharmaceutical preparation comprising human RPE cells derived from human embryonic stem cells or other pluripotent stem cells. Pharmaceutical preparations may comprise at least about $10^1$, $10^2$, $5\times10^2$, $10^3$, $5\times10^3$, $10^4$, $10^5$, $10^6$, $10^7$, $10^8$ or about $10^9$ hRPE cells.

In other embodiments, the invention provides a cryopreserved preparation of the RPE cells described herein. The cryopreserved preparation may be frozen for storage for days or years. The cells may be stored by any appropriate method known in the art, e.g., cryogenically frozen and may be frozen at any temperature appropriate for storage of the cells. For example, the cells may be frozen at approximately −20° C., −80° C., −120° C., or at any other temperature appropriate for storage of cells. Cryogenically frozen cells are stored in appropriate containers and prepared for storage to reduce risk of cell damage and maximize the likelihood that the cells will survive thawing. In other embodiments, RPE cells can be maintained at room temperature, or refrigerated at, for example, approximately 4° C. Cryopreserved preparations of the compositions described herein may comprise at least about $10^1$, $10^2$, $5\times10^2$, $10^3$, $5\times10^3$, $10^4$ $10^5$, $10^6$, $10^7$, $10^8$ or about $10^9$ hRPE cells. In certain embodiments, the hRPE cells of the invention are recovered from storage following cryopreservation. In certain embodiments, greater than 65%, 70%, 75,%, or greater than 80% of the RPE cells retain viability following cryopreservation. In other embodiments, greater than 85%, 90%, 91%, 92%, 93%, 94%, 95%, 96%, 97%, 98%, or greater than 99% of the RPE cells retain viability following cryopreservation.

In another aspect, the invention provides substantially purified preparations of human RPE cells have any combination of the structural, molecular, and functional characteristics described herein. Such preparations may be formulated as pharmaceutical preparations for administration and/or may be formulated for cryopreservation.

In another aspect, the invention provides use of the human RPE cells described herein in the manufacture of a medicament to treat a condition in a patient in need thereof. In another embodiment, the invention provides use of a cell culture comprising the human RPE cells described herein in the manufacture of a medicament to treat a condition in a patient in need thereof. In another embodiment, the invention provides the use of a pharmaceutical preparation comprising the human RPE cells described herein in the manufacture of a medicament to treat a condition in a patient in need thereof. Conditions that may be treated include, without limitation, degenerative diseases of the retina, such as Stargardt's macular dystrophy, retinitis pigmentosa, macular degeneration, glaucoma, and diabetic retinopathy. In certain embodiments, the invention provides methods for treating or preventing a condition characterized by retinal degeneration, comprising administering to a subject in need thereof an effective amount of a preparation comprising RPE cells, which RPE cells are derived from mammalian embryonic stem cells. Conditions characterized by retinal degeneration include, for example, Stargardt's macular dystrophy, age related macular degeneration, diabetic retinopathy, and retinitis pigmentosa.

In other embodiments, the invention provides a solution of human RPE cells derived from a human embryonic stem cell, or other pluripotent stem cell, which RPE cells have any combinations of the features described herein. Such a solutions may comprise at least about $10^1$, $10^2$, $5 \times 10^2$, $10^3$, $5 \times 10^3$, $10^4$ $10^5$, $10^6$, $10^7$, $10^8$ or about $10^9$ hRPE cells as described herein. Such solutions are suitable for injection to a subject. Such solutions are suitable for cryopreservation as described herein. This invention also provides a use of these solutions for the manufacture of a medicament to treat a disease that could be treated by the administration of RPE cells, such as, for example, retinal degenerative diseases of the eye.

In another aspect, the RPE cells of the invention are derived from human embryonic stem cells, or other pluripotent stem cells, previously derived under GMP conditions. In one embodiment, the human ES cells are derived from one or more blastomeres of an early cleavage stage embryo, optionally without destroying the embryo. In another embodiment, the human ES cells are from a library of human embryonic stem cells. In certain embodiments said library of human embryonic stem cells comprises stem cells, each of which is hemizygous, homozygous, or nullizygous for at least one MHC allele present in a human population, wherein each member of said library of stem cells is hemizygous, homozygous, or nullizygous for a different set of MHC alleles relative to the remaining members of the library. In further embodiments, the library of human embryonic stem cells comprises stem cells that are hemizygous, homozygous, or nullizygous for all MHC alleles present in a human population. In certain other embodiments, the invention provides a library of RPE cells, each of which is hemizygous, homozygous, or nullizygous for at least one MHC allele present in a human population, wherein each member of said library of RPE cells is hemizygous, homozygous, or nullizygous for a different set of MHC alleles relative to the remaining members of the library. In further embodiments, invention provides a library of human RPE cells that are hemizygous, homozygous, or nullizygous for all MHC alleles present in a human population.

In certain embodiments of any of the foregoing, said substantially purified culture of RPE cells (with or without mature RPE cells) are frozen for storage. The cells may be stored by any appropriate method known in the art, e.g., cryogenically frozen and may be frozen at any temperature appropriate for storage of the cells. For example, the cells may be frozen at approximately −20° C., −80° C., −120° C., or at any other temperature appropriate for storage of cells. Cryogenically frozen cells are stored in appropriate containers and prepared for storage to reduce risk of cell damage and maximize the likelihood that the cells will survive thawing. In other embodiments, RPE cells can be maintained at room temperature, or refrigerated at, for example, approximately 4° C.

In certain embodiments of any of the foregoing, human RPE cells are produced in accordance with Good Manufacturing Practices (GMP). In certain embodiments of any of the foregoing, the human embryonic stem cells from which the RPE cells are differentiated were derived in accordance with Good Manufacturing Practices (GMP). In certain embodiments of any of the foregoing, the human embryonic stem cells from which the RPE cells are differentiated were derived from one or more blastomeres removed from an early stage embryo without destroying the remaining embryo. As such, the invention provides GMP compliant preparations of RPE cells, including substantially purified preparations of RPE cells. Such preparations are substantially free of viral, bacterial, and/or fungal contamination or infection.

In certain embodiments of any of the foregoing, compositions or preparations of RPE cells comprise at least $1 \times 10^5$ RPE cells, at least $5 \times 10^5$ RPE cells, at least $1 \times 10^6$ RPE cells, at least $5 \times 10^6$ RPE cells, at least $1 \times 10^7$ RPE cells, at least $2 \times 10^7$ RPE cells, at least $3 \times 10^7$ RPE cells, at least $4 \times 10^7$ RPE cells, at least $5 \times 10^7$ RPE cells, at least $6 \times 10^7$ RPE cells, at least $7 \times 10^7$ RPE cells, at least $8 \times 10^7$ RPE cells, at least $9 \times 10^7$ RPE cells, at least $1 \times 10^8$ RPE cells, at least $2 \times 10^8$ RPE cells, at least $5 \times 10^8$ RPE cells, at least $7 \times 10^8$ RPE cells, or at least $1 \times 10^9$ RPE cells. In certain embodiments, the number of RPE cells in the preparation includes differentiated RPE cells, regardless of level of maturity and regardless of the relative percentages of differentiated RPE cells and mature differentiated RPE cells. In other embodiments, the number of RPE cells in the preparation refers to the number of either differentiated RPE cells or mature RPE cells.

In certain embodiments, the method further comprises formulating the differentiated RPE cells and/or differentiated mature RPE cells to produce a preparation of RPE cells suitable for transplantation.

In another aspect, the invention provides a method for treating or preventing a condition characterized by retinal degeneration, comprising administering to a subject in need thereof an effective amount of a preparation comprising RPE cells, which RPE cells are derived from human pluripotent stem cells. In certain embodiments, the RPE cells are derived using any of the methods described herein. Conditions characterized by retinal degeneration include, for example, Stargardt's macular dystrophy, age related macular degeneration (dry or wet), diabetic retinopathy, and retinitis pigmentosa.

In certain embodiments, the preparation was previously cryopreserved and was thawed before transplantation.

In certain embodiments, the method of treating further comprises administration of cyclosporin or one or more other immunosuppressants. When immunosuppressants are used, they may be administered systemically or locally, and they may be administered prior to, concomitantly with, or following administration of the RPE cells. In certain embodiments, immunosuppressive therapy continues for weeks, months, years, or indefinitely following administration of RPE cells.

In certain embodiments, the method of treatment comprises administration of a single dose of RPE cells. In other embodiments, the method of treatment comprises a course of therapy where RPE cells are administered multiple times over some period. Exemplary courses of treatment may comprise weekly, biweekly, monthly, quarterly, biannually, or yearly treatments. Alternatively, treatment may proceed in phases whereby multiple doses are required initially (e.g., daily doses for the first week), and subsequently fewer and less frequent doses are needed. Numerous treatment regimens are contemplated.

In certain embodiments, the administered RPE cells comprise a mixed population of differentiated RPE cells and mature RPE cells. In other embodiments, the administered RPE cells comprise a substantially purified population of either differentiated RPE cells or mature RPE cells. For example, the administered RPE cells may contain less than 25%, 20%, 15%, 10%, 9%, 8%, 7%, 6%, 5%, 4%, 3%, 2%, or less than 1% of the other RPE cell-type.

In certain embodiments, the RPE cells are formulated in a pharmaceutically acceptable carrier or excipient.

In certain embodiments, the preparation comprising RPE cells is transplanted in a suspension, matrix or substrate. In certain embodiments, the preparation is administered by injection into the subretinal space of the eye. In certain embodiments, the preparation is administered transcorneally. In certain embodiments, about $10^4$ to about $10^6$ cells are administered to the subject. In certain embodiments, the method further comprises the step of monitoring the efficacy of treatment or prevention by measuring electroretinogram responses, optomotor acuity threshold, or luminance threshold in the subject. The method may also comprise monitoring the efficacy of treatment or prevention by monitoring immunogenicity of the cells or migration of the cells in the eye.

In certain aspects, the invention provides a pharmaceutical preparation for treating or preventing a condition characterized by retinal degeneration, comprising an effective amount of RPE cells, which RPE cells are derived from human embryonic stem cells. The pharmaceutical preparation may be formulated in a pharmaceutically acceptable carrier according to the route of administration. For example, the preparation may be formulated for administration to the subretinal space or cornea of the eye. The composition may comprise at least $10^4$, $10^5$, $5\times10^5$, $6\times10^5$, $7\times10^5$, $8\times10^5$, $9\times10^5$, $10^6$, $2\times10^6$, $3\times10^6$, $4\times10^6$, $5\times10^6$, $6\times10^6$, $7\times10^6$, $8\times10^6$, $9\times10^6$, or $10^7$ RPE cells. In certain embodiments, the composition may comprise at least $2\times10^7$, $5\times10^7$, $6\times10^7$, $7\times10^7$, $8\times10^7$, $9\times10^7$, $1\times10^8$ RPE cells. In certain embodiments, the RPE cells may include mature RPE cells, and thus the cell number includes the total of both differentiated RPE cells and mature differentiated RPE cells.

In another aspect, the invention provides a method for screening to identify agents that modulate the survival of RPE cells. For example, RPE cells differentiated from human embryonic stem cells can be used to screen for agents that promote RPE survival. Identified agents can be used, alone or in combination with RPE cells, as part of a treatment regimen. Alternatively, identified agents can be used as part of a culture method to improve the survival of RPE cells differentiated in vitro.

In another aspect, the invention provides a method for screening to identify agents that modulate RPE cell maturity. For example, RPE cells differentiated from human ES cells can be used to screen for agents that promote RPE maturation.

In certain embodiments of any of the foregoing, the method is performed in accordance with Good Manufacturing Practices (GMP). In certain embodiments of any of the foregoing, the human embryonic stem cells from which the RPE cells are differentiated were derived in accordance with Good Manufacturing Practices (GMP). In certain embodiments of any of the foregoing, the human embryonic stem cells from which the RPE cells are differentiated were derived from one or more blastomere removed from an early stage embryo without destroying the remaining embryo.

In another aspect, the invention contemplates that, instead of human embryonic stem cells, the starting material for producing RPE cells, or preparations thereof, can be other types of human pluripotent stem cells. By way of example, the invention contemplates that induced pluripotent stem (iPS) cells, which have the characteristic of hES, can similarly be used as a starting material for differentiating RPE cells using the methods described herein. Such iPS cells can be obtained from a cell bank, or otherwise previously derived. Alternatively, iPS cells can be newly generated prior to commencing differentiation to RPE cells.

In one embodiment, RPE cells or preparations differentiated from pluripotent stem cells, including iPS cells, are used in a therapeutic method.

The invention contemplates any combination of the aspects and embodiments described above or below. For example, preparations of RPE cells comprising any combination of differentiated RPE cells and mature RPE cells can be used in the treatment of any of the diseases and conditions described herein. Similarly, methods described herein for producing RPE cells using human embryonic stem cells as a starting material may be similarly performed using any human pluripotent stem cells as a starting material.

DETAILED DESCRIPTION OF THE INVENTION

Figure 1:
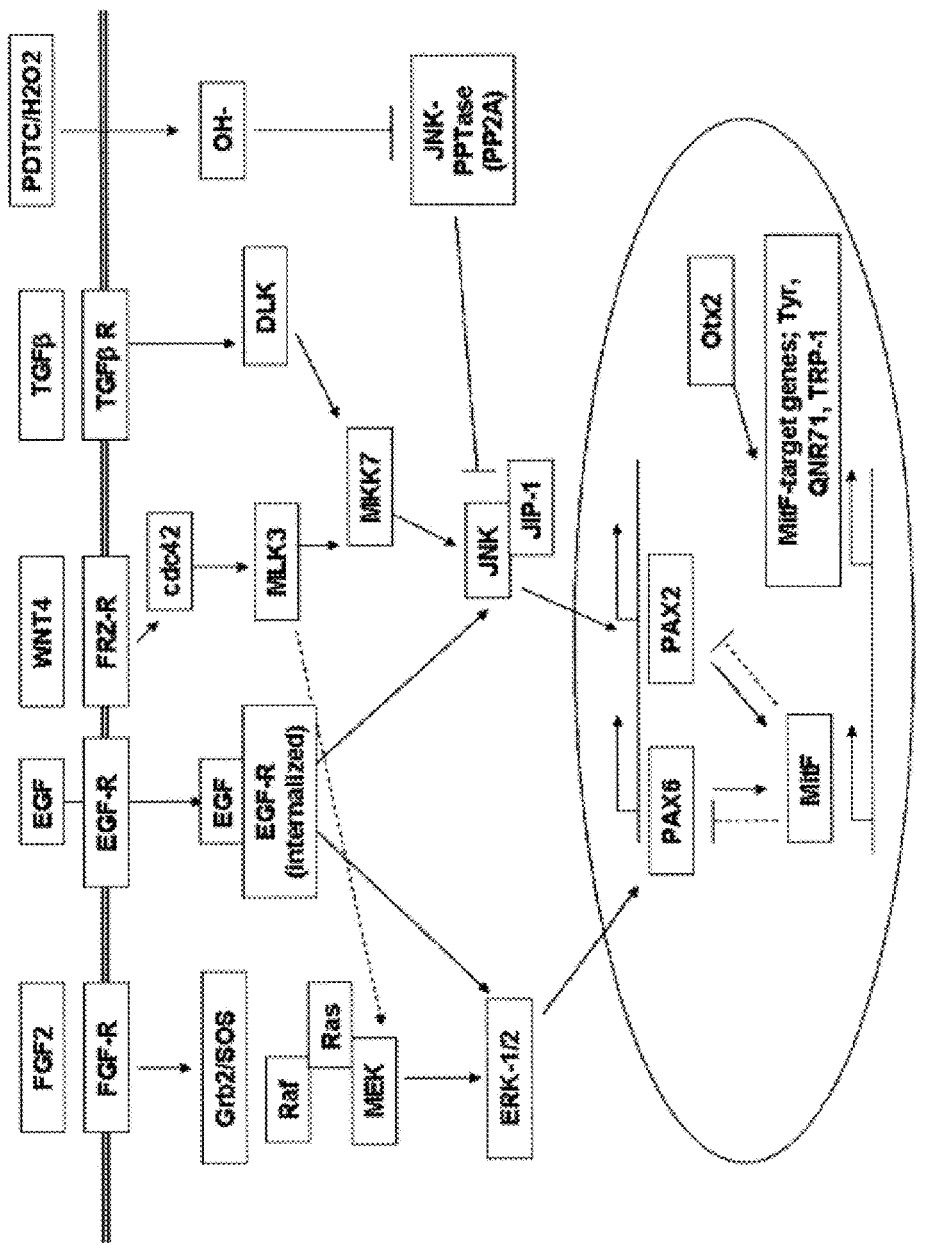
FIG. 1 is a schematic model showing the developmental ontogeny of human RPE cells derived from human embryonic stem cells.
Figure 2:
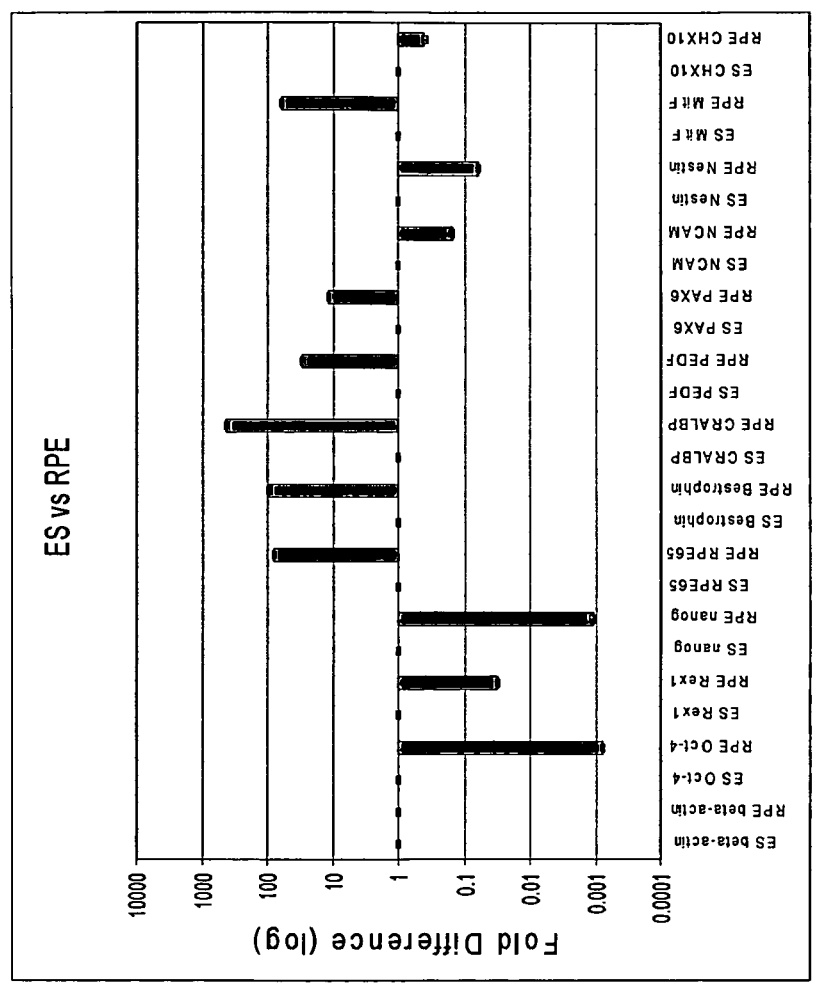
FIG. 2 is a graph showing gene expression comparison of hES cells and human embryonic stem cell-derived RPE cells by quantitative, Real-Time, Reverse Transcription PCR (qPCR).

In order that the invention herein described may be fully understood, the following detailed description is set forth.

Various embodiments of the invention are described in detail and may be further illustrated by the provided examples.

Unless defined otherwise, all technical and scientific terms used herein have the same meaning as those commonly understood by one of ordinary skill in the art to which this invention belongs. Although methods and materials similar or equivalent to those described herein can be used in the invention or testing of the present invention, suitable methods and materials are described below. The materials, methods and examples are illustrative only, and are not intended to be limiting.

All publications, patents, patent publications and applications and other documents mentioned herein are incorporated by reference in their entirety.

In order to further define the invention, the following terms and definitions are provided herein.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Throughout this specification, the word "comprise" or variations such as "comprises" or "comprising" will be understood to imply the inclusion of a stated integer or groups of integers but not the exclusion of any other integer or group of integers.

By "embryo" or "embryonic" is meant a developing cell mass that has not implanted into the uterine membrane of a maternal host. An "embryonic cell" is a cell isolated from or contained in an embryo. This also includes blastomeres, obtained as early as the two-cell stage, and aggregated blastomeres.

The term "embryonic stem cells" refers to embryo-derived cells. More specifically it refers to cells isolated from the inner cell mass of blastocysts or morulae and that have been serially passaged as cell lines. The term also includes cells isolated from one or more blastomeres of an embryo, preferably without destroying the remainder of the embryo. The term also includes cells produced by somatic cell nuclear transfer, even when non-embryonic cells are used in the process.

The term "human embryonic stem cells" (hES cells) is used herein as it is used in the art. This term includes cells derived from the inner cell mass of human blastocysts or morulae that have been serially passaged as cell lines. The hES cells may be derived from fertilization of an egg cell with sperm or DNA, nuclear transfer, parthenogenesis, or by means to generate hES cells with homozygosity in the HLA region. Human ES cells are also cells derived from a zygote, blastomeres, or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce a cell. Human embryonic stem cells of the present invention may include, but are not limited to, MA01, MA09, ACT-4, No. 3, H1, H7, H9, H14 and ACT30 embryonic stem cells. In certain embodiments, human ES cells used to produce RPE cells are derived and maintained in accordance with GMP standards. Human embryonic stem cells, regardless of their source or the particular method use to produce them, can be identified based on (i) the ability to differentiate into cells of all three germ layers, (ii) expression of at least Oct-4 and alkaline phosphatase, and (iii) ability to produce teratomas when transplanted into immunocompromised animals.

The term "human embryo-derived cells" (hEDC) refers to morula-derived cells, blastocyst-derived cells including those of the inner cell mass, embryonic shield, or epiblast, or other totipotent or pluripotent stem cells of the early embryo, including primitive endoderm, ectoderm, and mesoderm and their derivatives, also including blastomeres and cell masses from aggregated single blastomeres or embryos from varying stages of development, but excluding human embryonic stem cells that have been passaged as cell lines.

As used herein, the term "pluripotent stem cells" includes embryonic stem cells, embryo-derived stem cells, and induced pluripotent stem cells, regardless of the method by which the pluripotent stem cells are derived. Pluripotent stem cells are defined functionally as stem cells that: (a) are capable of inducing teratomas when transplanted in immunodeficient (SCID) mice; (b) are capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase, SSEA-3 surface antigen, SSEA-4 surface antigen, nanog, TRA-1-60, TRA-1-81, SOX2, REX1, etc). Exemplary pluripotent stem cells can be generated using, for example, methods known in the art. Exemplary pluripotent stem cells include embryonic stem cells derived from the ICM of blastocyst stage embryos, as well as embryonic stem cells derived from one or more blastomeres of a cleavage stage or morula stage embryo (optionally without destroying the remainder of the embryo). Such embryonic stem cells can be generated from embryonic material produced by fertilization or by asexual means, including somatic cell nuclear transfer (SCNT), parthenogenesis, and androgenesis. Further exemplary pluripotent stem cells include induced pluripotent stem cells (iPS cells) generated by reprogramming a somatic cell by expressing or inducing expression of a combination of factors (herein referred to as reprogramming factors). iPS cells can be generated using fetal, postnatal, newborn, juvenile, or adult somatic cells. In certain embodiments, factors that can be used to reprogram somatic cells to pluripotent stem cells include, for example, a combination of Oct4 (sometimes referred to as Oct 3/4), Sox2, c-Myc, and Klf4. In other embodiments, factors that can be used to reprogram somatic cells to pluripotent stem cells include, for example, a combination of Oct 4, Sox2, Nanog, and Lin28. In other embodiments, somatic cells are reprogrammed by expressing at least 2 reprogramming factors, at least three reprogramming factors, or four reprogramming factors. In other embodiments, additional reprogramming factors are identified and used alone or in combination with one or more known reprogramming factors to reprogram a somatic cell to a pluripotent stem cell.

The terms "RPE cell" and "differentiated RPE cell" and "ES-derived RPE cell" and "human RPE cell" are used interchangeably throughout to refer to an RPE cell differentiated from a human embryonic stem cell using a method of the invention. The term is used generically to refer to differentiated RPE cells, regardless of the level of maturity of the cells, and thus may encompass RPE cells of various levels of maturity. Differentiated RPE cells can be visually recognized by their cobblestone morphology and the initial appearance of pigment. Differentiated RPE cells can also be identified molecularly based on substantial lack of expression of embryonic stem cell markers such as Oct-4 and nanog, as well as based on the expression of RPE markers such as RPE-65, PEDF, CRALBP, and bestrophin. Note that when other RPE-like cells are referred to, they are generally referred to specifically as adult, fetal or APRE19 cells. Thus, unless otherwise specified, RPE cells, as used herein, refers to RPE cells differentiated from human embryonic stem cells.

The terms "mature RPE cell" and "mature differentiated RPE cell" are used interchangeably throughout to refer to changes that occur following initial differentiating of RPE cells. Specifically, although RPE cells can be recognized, in part, based on initial appearance of pigment, after differentiation mature RPE cells can be recognized based on enhanced pigmentation. Pigmentation post-differentiation is not indicative of a change in the RPE state of the cells (e.g., the cells are still differentiated RPE cells). Rather, the changes in pigment post-differentiation correspond to the density at which the RPE cells are cultured and maintained. Thus, mature RPE cells have increased pigmentation that accumulates after initial differentiation. Mature RPE cells are more pigmented than RPE cells—although RPE cells do have some level of pigmentation. Mature RPE cells can be subcultured at a lower density, such that the pigmentation decreases. In this context, mature RPE cells can be cultured to produce RPE cells. Such RPE cells are still differentiated RPE cells that express markers of RPE differentiation. Thus, in contrast to the initial appearance of pigmentation that occurs when RPE cells begin to differentiate, pigmentation changes post-differentiation are phenomenological and do not reflect dedifferentiation of the cells away from an RPE fate. Note that changes in pigmentation post-differentiation also correlate with changes in pax-2 expression. Note that when other RPE-like cells are referred to, they are generally referred to specifically as adult, fetal or APRE19 cells. Thus, unless otherwise specified, RPE cells, as used herein, refers to RPE cells differentiated from human embryonic stem cells.

"APRE-19" refers to cells of a previously derived, human RPE cell line. APRE-19 cells arose spontaneously and are not derived from human embryos or embryonic stem cells.

Overview

This invention provides preparations and compositions comprising human retinal pigmented epithelium (RPE) cells derived from human embryonic stem cells or other human pluripotent stem cells. The RPE cells are pigmented, to at least some extent. The RPE cells do not express (at any appreciable level) the embryonic stem cell markers Oct-4, nanog, or Rex-1. Specifically, expression of these ES genes is approximately 100-1000 fold lower in RPE cells than in ES cells, when assessed by quantitative RT-PCR. The RPE cells do express, both at the mRNA and protein level, one or more of the following: RPE65, CRALBP, PEDF, Bestrophin, MitF and/or Otx2. In certain other embodiments, the RPE cells express, both at the mRNA and protein level, one or more of Pax-2, Pax-6, MitF, and tyrosinase. In certain embodiments of any of the foregoing, the RPE cells are mature RPE cells with increased pigmentation in comparison to differentiated RPE cells.

The invention provides for human RPE cells, cell cultures comprising a substantially purified population of human RPE cells, pharmaceutical preparations comprising human retinal pigmented epithelial cells and cryopreserved preparations of the human RPE cells. In certain embodiments, the invention provides for the use of the human RPE cells in the manufacture of a medicament to treat a condition in a patient in need thereof. Alternatively, the invention provides the use of the cell cultures in the manufacture of a medicament to treat a condition in a patient in need thereof. The invention also provides the use of the pharmaceutical preparations in the manufacture of a medicament to treat a condition in a patient in need thereof. In any of the foregoing, preparations comprising RPE cells may include differentiated RPE cells of varying levels of maturity, or may be substantially pure with respect to differentiated RPE cells of a particular level of maturity. In certain embodiments of any of the foregoing, the preparations comprising RPE cells are prepared in accordance with Good Manufacturing Practices (GMP) (e.g., the preparations are GMP-compliant). In certain embodiments, the preparations comprising RPE cells are substantially free of bacterial, viral, or fungal contamination or infection.

The human RPE cells (embryo-derived or derived from other pluripotent stem cells) can be identified and characterized based on their structural properties. Specifically, and in certain embodiments, these cells are unique in that they can be identified or characterized based on the expression or lack of expression (as assessed at the level of the gene or the level of the protein) of one or more markers. For example, in certain embodiments, differentiated ES-derived RPE cells can be identified or characterized based on expression of one or more (e.g., the cells can be characterized based on expression of at least one, at least two, at least three, at least four, at least five, or at least six) of the following markers: RPE-65, Bestrophin, PEDF, CRALBP, Otx2, and Mit-F. Additionally or alternatively, ES-derived RPE cells can be identified or characterized based on expression of PAX2, tyrosinase, and/or PAX6. Additionally or alternatively, hRPE cells can be identified or characterized based on expression or lack of expression (as assessed at the level of the gene or the level of the protein) of one or more (1, 2, 3, 4, 5, 6, 7, 8, 9, 10, or more than 10) markers analyzed in any of Tables 1-3.

Additionally or alternatively, ES-derived RPE cells can also be identified and characterized based on the degree of pigmentation of the cell. Differentiated hRPE cells that are rapidly dividing are lightly pigmented. However, when cell density reaches maximal capacity, or when hRPE cells are specifically matured, hRPE take on their characteristic phenotypic hexagonal shape and increase pigmentation level by accumulating melanin and lipofuscin. As such, initial accumulation of pigmentation serves as an indicator of RPE differentiation and increased pigmentation associated with cell density serves as an indicator of RPE maturity.

Preparations comprising RPE cells include preparations that are substantially pure, with respect to non-RPE cell types, but which contain a mixture of differentiated RPE cells and mature differentiated RPE cells. Preparations comprising RPE cells also include preparations that are substantially pure both respect to non-RPE cell types and with respect to RPE cells of other levels of maturity.

For any of the foregoing embodiments, the invention contemplates that the RPE cells (characterized as described above) may be derived from human pluripotent stem cells, for example iPS cells and embryonic stem cells. In certain embodiments, the RPE cells are derived from human pluripotent stem cells using any of the methods described herein.

RPE Cell Differentiation

Embryonic stem cells (ES) can be indefinitely maintained in vitro in an undifferentiated state and yet are capable of differentiating into virtually any cell type, providing a limitless supply of rejuvenated and histocompatible cells for transplantation therapy. The problem of immune rejection can be overcome with nuclear transfer and parthenogenetic technology. Thus, human embryonic stem (hES) cells are useful for studies on the differentiation of human cells and can be considered as a potential source for transplantation therapies. To date, the differentiation of human and mouse ES cells into numerous cell types have been reported (reviewed by Smith, 2001) including cardiomyocytes [Kehat et al. 2001, Mummery et al., 2003 Carpenter et al., 2002], neurons and neural precursors (Reubinoff et al. 2000, Carpenter et al. 2001, Schuldiner et al., 2001), adipocytes (Bost et al., 2002, Aubert et al., 1999), hepatocyte-like cells (Rambhatla et al., 2003), hematopoetic cells (Chadwick et al., 2003). oocytes (Hubner et all., 2003), thymocyte-like cells (Lin R Y et al., 2003), pancreatic islet cells (Kahan, 2003), and osteoblasts (Zur Nieden et al., 2003).

The present invention provides for the differentiation of human ES cells into a specialized cell in the neuronal lineage, the retinal pigment epithelium (RPE). RPE is a densely pigmented epithelial monolayer between the choroid and neural retina. It serves as a part of a barrier between the bloodstream and retina. Its functions include phagocytosis of shed rod and cone outer segments, absorption of stray light, vitamin A metabolism, regeneration of retinoids, and tissue repair (Grierson et al., 1994, Fisher and Reh, 2001, Marmorstein et al., 1998). The RPE can be recognized by its cobblestone cellular morphology of black pigmented cells. In addition, there are several known markers of the RPE, including cellular retinaldehyde-binding protein (CRALBP), a cytoplasmic protein that is also found in apical microvilli (Bunt-Milam and Saari, 1983); RPE65, a cytoplasmic protein involved in retinoid metabolism (Ma et al., 2001, Redmond et al., 1998); bestrophin, the product of the Best vitelliform macular dystrophy gene (VMD2, Marmorstein et al., 2000), and pigment epithelium derived factor (PEDF), a 48 kD secreted protein with angiostatic properties (Karakousis et al., 2001, Jablonski et al., 2000).

RPE plays an important role in photoreceptor maintenance, and various RPE malfunctions in vivo are associated with a number of vision-altering ailments, such as RPE detachment, displasia, atrophy, retinopathy, retinitis pigmentosa, macular dystrophy or degeneration, including age-related macular degeneration, which can result in photoreceptor damage and blindness. Because of its wound healing abilities, RPE has been extensively studied in application to transplantation therapy. It has been shown in several animal models and in humans (Gouras et al., 2002, Stanga et al., 2002, Binder et al., 2002, Schraermeyer et al., 2001, reviewed by Lund et al., 2001) that RPE transplantation has a good potential of vision restoration. Recently another prospective niche for RPE transplantation was proposed and even reached the phase of clinical trials: since these cells secrete dopamine, they could be used for treatment of Parkinson disease (Subramanian, 2001). However, even in an immune-privileged eye, there is a problem of graft rejection, hindering the progress of this approach if allogenic transplant is used. The other problem is the reliance on fetal tissue, as adult RPE has a very low proliferative potential. The present invention decreases the likelihood that graft rejection will occur and removes the reliance on the use of fetal tissue.

As a source of immune compatible tissues, hES cells hold a promise for transplantation therapy, as the problem of immune rejection can be overcome with nuclear transfer technology. The use of the new differentiation derivatives of human ES cells, including retinal pigment epithelium-like cells and neuronal precursor cells, and the use of the differentiation system for producing the same offers an attractive potential supply of RPE and neuronal precursor cells for transplantation.

Accordingly, one aspect of the present invention is to provide an improved method of generating RPE cells derived from human embryonic stem cells, which may be purified and/or isolated. Such cells are useful for therapy for retinal degeneration diseases such as, for example, retinitis pigmentosa, macular degeneration and other eye disorders. The cell types that can be produced using this invention include, but are not limited to, RPE cells and RPE progenitor cells. Cells that may also be produced include iris pigmented epithelial (IPE) cells and other vision associated neural cells, such as internuncial neurons (e.g. "relay" neurons of the inner nuclear layer (INL)) and amacrine cells. Additionally, retinal cells, rods, cones, and corneal cells can be produced. In another embodiment of the present invention, cells providing the vasculature of the eye can also be produced.

The human embryonic stem cells are the starting material of this method. The embryonic stem cells may be cultured in any way known in the art, such as in the presence or absence of feeder cells. Additionally, human ES cells produced using any method can be used as the starting material to produce RPE cells. For example, the human ES cells may be derived from blastocyst stage embryos that were the product of in vitro fertilization of egg and sperm. Alternatively, the human ES cells may be derived from one or more blastomeres removed from an early cleavage stage embryo, optionally, without destroying the remainder of the embryo. In still other embodiments, the human ES cells may be produced using nuclear transfer. As a starting material, previously cryopreserved human ES cells can be used.

In the first step of this method for producing RPE cells, human embryonic stem cells are cultured as embryoid bodies. Embryonic stem cells may be pelleted, resuspended in culture medium, and plated on culture dishes (e.g., low attachment culture dishes). Cells may be cultured in any medium that is sufficient for growth of cells at high-density, such as, commercially available medium for viral, bacterial, insect, or animal cell culture. In certain embodiments, nutrient rich, low protein medium is used (e.g., MDBK-GM medium, containing about 150 mg/mL (0.015%) animal-derived protein). When low protein medium is used, the medium contains, for example, less than or equal to about 5%, 4%, 3%, 2.5%, 2%, 1.5%, 1%, 0.75%, 0.5%, 0.25%, 0.2%, 0.1%, 0.05%, 0.02%, 0.016%, 0.015%, or even less than or equal to 0.010% animal-derived protein. Note that reference to the percentage of protein present in low protein medium refers to the medium alone and does not account for protein present in, for example, B-27 supplement. Thus, it is understood that when cells are cultured in low protein medium and B-27 supplement, the percentage of protein present in the medium may be higher.

In certain embodiments, nutrient rich, protein-free medium is used (e.g., MDBK-MM medium). Other examples of culture media include, for example, OptiPro SFM, VP-SFM, and EGM-2. Such media may include nutrient components such as insulin, transferrin, sodium selenite, glutamine, albumin, ethanolamine, fetuin, peptone, purified lipoprotein material, vitamin A, vitamin C, and vitamin E.

In certain embodiments, cell cultures in either low protein or protein free medium are supplemented with serum free B-27 supplement (Brewer et al., Journal of Neuroscience Research 35:567-576 (1993)). Nutrient components of B27 supplement may include biotin, L-carnitine, corticosterone, ethanolamine, D+-galactose, reduced glutathione, lineleic acid, linolenic acid, progesterone, putrescine, retinyl acetate, selenium, triodo-1-thyronine (T3), DL-alpha-tocopherol (vitamin E), DL-alpha-tocopherol acedate, bovine serum albumin, catalase, insulin, superoxide dismutase, and transferrin.

When cells are cultured in protein free medium supplemented with B-27, protein free refers to the medium prior to addition of B-27.

The medium may also contain supplements such as heparin, hydrocortisone, ascorbic acid, serum (such as, for example, fetal bovine serum), or a growth matrix (such as, for example, extracellular matrix from bovine corneal epithelium, matrigel (BD biosciences), or gelatin).

In this method of the present invention, RPE cells differentiate from the embryoid bodies. Isolating RPE cells from the EBs allows for the expansion of the RPE cells in an enriched culture in vitro. For human cells, RPE cells may be obtained form EBs grown for less than 90 days. In certain embodiments of the present invention, RPE cells arise in human EBs grown for 7-14 days. In other embodiments, RPE cells arise in human EBs grown for 14-28 days. In another embodiment, RPE cells are identified and may be isolated from human EBs grown for 28-45 days. In another embodiment, RPE cells arise in human EBs grown for 45-90 days. The medium used to culture embryonic stem cells, embryoid bodies, and RPE cells may be removed and/or replaced with the same or different media at any interval. For example, the medium may be removed and/or replaced after 0-7 days, 7-10 days, 10-14 days, 14-28 days, or 28-90 days. In certain embodiments, the medium is replaced at least daily, every other day, or at least every three days.

In certain embodiments, the RPE cells that differentiate from the EBs are washed and dissociated (e.g., by Trypsin/EDTA, collegenase B, collegenase IV, or dispase). In certain embodiments, a non-enzymatic solution is used to disassociate the cells, such as a high EDTA-containing solution such as, for example, Hanks-based cell disassociation buffer.

RPE cells are selected from the dissociated cells and cultured separately to produce a substantially purified culture of RPE cells. RPE cells are selected based on characteristics associated with RPE cells. For example, RPE cells can be recognized by cobblestone cellular morphology and pigmentation. In addition, there are several known markers of the RPE, including cellular retinaldehyde-binding protein (CRALBP), a cytoplasmic protein that is also found in apical microvilli (Bunt-Milam and Saari, 1983); RPE65, a cytoplasmic protein involved in retinoid metabolism (Ma et al., 2001, Redmond et al., 1998); bestrophin, the product of the Best vitelliform macular dystrophy gene (VMD2, Marmorstein et al., 2000), and pigment epithelium derived factor (PEDF), a 48 kD secreted protein with angiostatic properties (Karakousis et al., 2001, Jablonski et al., 2000). Alternatively, RPE cells can be selected based on cell function, such as by phagocytosis of shed rod and cone outer segments, absorption of stray light, vitamin A metabolism, regeneration of retinoids, and tissue repair (Grierson et al., 1994, Fisher and Reh, 2001, Marmorstein et al., 1998). Evaluation may also be performed using behavioral tests, fluorescent angiography, histology, tight junctions conductivity, or evaluation using electron microscopy. Another embodiment of the present invention is a method of identifying RPE cells by comparing the messenger RNA transcripts of such cells with cells derived in-vivo. In certain embodiments, an aliquot of cells is taken at various intervals during the differentiation of embryonic stem cells to RPE cells and assayed for the expression of any of the markers described above. These characteristic distinguish differentiated RPE cells.

RPE cell culture media may be supplemented with one or more growth factors or agents. Growth factors that may be used include, for example, EGF, FGF, VEGF, and recombinant insulin-like growth factor. Other growth factors that may be used in the present invention include 6Ckine (recombinant), activin A, AlphaA-interferon, alpha-interferon, amphiregulin, angiogenin, B-endothelial cell growth factor, beta cellulin, B-interferon, brain derived neurotrophic factor, C10 (recombinant), cardiotrophin-1, ciliary neurotrophic factor, cytokine-induced neutrophil chemoattractant-1, endothelial cell growth supplement, eotaxin, epidermal growth factor, epithelial neutrophil activating peptide-78, erythropoiten, estrogen receptor-alpha, estrogen receptor-B, fibroblast growth factor (acidic/basic, heparin stabilized, recombinant), FLT-3/FLK-2 ligand (FLT-3 ligand), gamma-interferon, glial cell line-derived neurotrophic factor, Gly-His-Lys, granulocyte colony-stimulating factor, granulocyte macrophage colony-stimulating factor, GRO-alpha/MGSA, GRO-B, GRO-gamma, HCC-1, heparin-binding epidermal growth factor like growth factor, hepatocyte growth factor, heregulin-alpha (EGF domain), insulin growth factor binding protein-1, insulin-like growth factor binding protein-1/IGF-1 complex, insulin-like growth factor, insulin-like growth factor II, 2.5S nerve growth factor (NGF), 7S-NGF, macrophage inflammatory protein-1B, macrophage inflammatory protein-2, macrophage inflammatory protein-3 alpha, macrophage inflammatory protein-3B, monocyte chemotactic protein-1, monocyte chemotactic protein-2, monocyte chemotactic protein-3, neurotrophin-3, neurotrophin-4, NGF-B (human or rat recombinant), oncostatin M (human or mouse recombinant), pituitary extract, placenta growth factor, platelet-derived endothelial cell growth factor, platelet-derived growth factor, pleiotrophin, rantes, stem cell factor, stromal cell-derived factor 1B/pre-B cell growth stimulating factor, thrombopoetin, transforming growth factor alpha, transforming growth factor-B1, transforming growth factor-B2, transforming growth factor-B3, transforming growth-factor-B5, tumor necrosis factor (alpha and B), and vascular endothelial growth factor. Agents that can be used according to the present invention include cytokines such as interferon-alpha A, interferon-alpha A/D, interferon-.beta., interferon-gamma, interferon-gamma-inducible protein-10, interleukin-1, interleukin-2, interleukin-3, interleukin-4, interleukin-5, interleukin-6, interleukin-7, interleukin-8, interleukin-9, interleukin-10, interleukin-1, interleukin-12, interleukin-13, interleukin-15, interleukin-17, keratinocyte growth factor, leptin, leukemia inhibitory factor, macrophage colony-stimulating factor, and macrophage inflammatory protein-1 alpha.

Agents according to the invention also include hormones and hormone antagonists, such as 17B-estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagon, gonadotropin, hydrocortisone, insulin, insulin-like growth factor binding protein, L-3,3',5'-triiodothyronine, L-3,3',5-triiodothyronine, leptin, leutinizing hormone, L-thyroxine, melatonin, MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxine-binding globulin, and vasopressin.

In addition, agents according to the invention include extracellular matrix components such as fibronectin, proteolytic fragments of fibronectin, laminin, thrombospondin, aggrecan, and syndezan.

Agents according to the invention also include antibodies to various factors, such as anti-low density lipoprotein receptor antibody, anti-progesterone receptor, internal antibody, anti-alpha interferon receptor chain 2 antibody, antic-c chemokine receptor 1 antibody, anti-CD 118 antibody, anti-CD 119 antibody, anti-colony stimulating factor-1 antibody, anti-CSF-1 receptor/c-fms antibody, anti-epidermal growth factor (AB-3) antibody, anti-epidermal growth factor receptor antibody, anti-epidermal growth factor receptor, phospho-specific antibody, anti-epidermal growth factor (AB-1) antibody, anti-erythropoietin receptor antibody, anti-estrogen receptor antibody, anti-estrogen receptor, C-terminal antibody, anti-estrogen receptor-B antibody, anti-fibroblast growth factor receptor antibody, anti-fibroblast growth factor, basic antibody, anti-gamma-interferon receptor chain antibody, anti-gamma-interferon human recombinant antibody, anti-GFR alpha-1 C-terminal antibody, anti-GFR alpha-2 C-terminal antibody, anti-granulocyte colony-stimulating factor (AB-1) antibody, anti-granulocyte colony-stimulating factor receptor antibody, anti-insulin receptor antibody, anti-insulin-like growth factor-1 receptor antibody, anti-interleukin-6 human recombinant antibody, anti-interleukin-1 human recombinant antibody, anti-interleukin-2 human recombinant antibody, anti-leptin mouse recombinant antibody, anti-nerve growth factor receptor antibody, anti-p60, chicken antibody, anti-parathyroid hormone-like protein antibody, anti-platelet-derived growth factor receptor antibody, anti-platelet-derived growth factor receptor-B antibody, anti-platelet-derived growth factor-alpha antibody, anti-progesterone receptor antibody, anti-retinoic acid receptor-alpha antibody, anti-thyroid hormone nuclear receptor antibody, anti-thyroid hormone nuclear receptor-alpha 1/Bi antibody, anti-transferrin receptor/CD71 antibody, anti-transforming growth factor-alpha antibody, anti-transforming growth factor-B3 antibody, anti-tumor necrosis factor-alpha antibody, and anti-vascular endothelial growth factor antibody.

Growth factors, agents, and other supplements described herein may be used alone or in combination with other factors, agents, or supplements. Factors, agents, and supplements may be added to the media immediately or any time after cell culture.

In certain embodiments, the RPE cells are further cultured to produce a culture of mature RPE cells. The medium used to culture the RPE cells can be any medium appropriate for high-density cell culture growth, such as described herein. For example, the cells described herein may be cultured in VP-SFM, EGM-2, and MDBK-MM.

A more detailed description of certain operative combinations of the above described features of the invention is provided below.

In certain embodiments, a previously derived culture of human embryonic stem cells is provided. The hES cells can be, for example, previously derived from a blastocyst (produced by fertilization or nuclear transfer) or from one or more blastomeres from an early cleavage stage embryo (optionally without destroying the remainder of the embryo). The human ES cells are cultured as a suspension culture to produce embryoid bodies (EBs). The embryoid bodies are cultured in suspension for approximately 7-14 days. However, in certain embodiments, the EBs can be cultured in suspension for fewer than 7 days (less than 7, 6, 5, 4, 3, 2, or less than 1 day) or greater than 14 days. The EBs can be cultured in medium optionally supplemented with B-27 supplement.

After culturing the EBs in suspension culture, the EBs can transferred to produce an adherent culture. For example, the EBs can be plated in medium onto gelatin coated plates. When cultured as an adherent culture, the EBs can be cultured in the same type of media as when grown in suspension. In certain embodiments, the media is not supplemented with B-27 supplement when the cells are cultured as an adherent culture. In other embodiments, the medium is supplemented with B-27 initially (e.g., for less than or equal to about 7 days), but then subsequently cultured in the absence of B-27 for the remainder of the period as an adherent culture. The EBs can be cultured as an adherent culture for approximately 14-28. However, in certain embodiments, the EBs can be cultured for fewer than 14 days (less than 14, 13, 12, 11, 10, 9, 8, 7, 6, 5, 4, 3, 2, or less than 1 day) or greater than 28 days.

RPE cells begin to differentiate from amongst cells in the adherent culture of EBs. RPE cells can be visually recognized based on their cobblestone morphology and the initial appearance of pigmentation. As RPE cells continue to differentiate, clusters of RPE cells can be observed.

To enrich for RPE cells and to establish substantially purified cultures of RPE cells, RPE cells are dissociated from each other and from non-RPE cells using mechanical and/or chemical methods. A suspension of RPE cells can then be transferred to fresh medium and a fresh culture vessel to provide an enriched population of RPE cells.

Enriched cultures of RPE cells can be cultured in appropriate medium, for example, EGM-2 medium. This, or a functionally equivalent or similar medium, may be supplemented with one or more growth factors or agents (e.g., bFGF, heparin, hydrocortisone, vascular endothelial growth factor, recombinant insulin-like growth factor, ascorbic acid, human epidermal growth factor).

For embodiments in which the RPE cells are matured, the RPE cells can be further cultured in, for example MDBK-MM medium until the desired level of maturation is obtained. This can be determined by monitoring the increase in pigmentation level during maturation. As an alternative to MDBK-MM medium, a functionally equivalent or similar medium, may be used. Regardless of the particular medium used to mature the RPE cells, the medium may optionally be supplemented with one or more growth factors or agents.

The culture of RPE cells, and thus the preparations of RPE cells prepared from these cultures, can be substantially pure RPE cells containing less than 25%, 20%, 15%, 10%, 9%, 8%, 7%, 6%, 5%, 4%, 3%, 2%, or less than 1% non-RPE cells. In certain embodiments, the substantially purified (with respect to non-RPE cells) cultures contain RPE cells of varying levels of maturity. In other embodiments, the cultures are substantially pure both with respect to non-RPE cells and with respect to RPE cells of differing level of maturity.

For any of the foregoing embodiments, the invention contemplates that the RPE cells (characterized as described above) may be derived from human pluripotent stem cells, for example iPS cells and embryonic stem cells. In certain embodiments, the RPE cells are derived from human pluripotent stem cells using any of the methods described herein.

Preparations of Differentiated Pluripotent Stem Cell—Derived RPE Cells

The present invention provides preparations of human pluripotent stem cell-derived RPE cells. In certain embodiments, the preparation is a preparation of human embryonic stem cell-derived RPE cells. In certain embodiments, the preparation is a preparation of human iPS cell-derived RPE cells. In certain embodiments, the preparations are substantially purified (with respect to non-RPE cells) preparations comprising differentiated ES-derived RPE cells. By substantially purified, with respect to non-RPE cells, is meant that the preparation comprises at least 75%, 80%, 85%, 90%, 91%, 92%, 93%, 94%, 95%, 96%, 97%, 98%, 99%, or even greater than 99% RPE cells. In other words, the substantially purified preparation of RPE cells contains less than 25%, 20%, 15%, 10%, 9%, 8%, 7%, 6%, 5%, 4%, 3%, 2%, or less than 1% non-RPE cell type. In certain embodiments, the RPE cells in such a substantially purified preparation contain RPE cells of varying levels of maturity/pigmentation. In other embodiments, the RPE cells are substantially pure, both with respect to non-RPE cells and with respect to RPE cells of other levels of maturity. In certain embodiments, the preparations are substantially purified, with respect to non-RPE cells, and enriched for mature RPE cells. By enriched for mature RPE cells, it is meant that at least 30%, 40%, 45%, 50%, 55%, 60%, 65%, 70%, 75%, 80%, 85%, 90%, 91%, 92%, 93%, 94%, 95%, 96%, 97%, 98%, 99%, or even greater than 99% of the RPE cells are mature RPE cells. In other embodiments, the preparations are substantially purified, with respect to non-RPE cells, and enriched for differentiated RPE cells rather than mature RPE cells. By enriched for, it is meant that at least 30%, 40%, 45%, 50%, 55%, 60%, 65%, 70%, 75%, 80%, 85%, 90%, 91%, 92%, 93%, 94%, 95%, 96%, 97%, 98%, 99%, or even greater than 99% of the RPE cells are differentiated RPE cells rather than mature RPE cells. In certain embodiments, mature RPE cells are distinguished from RPE cells by one or more of: the level of pigmentation, level of expression of Pax-2, Pax-6, and/or tyrosinase. In certain embodiments, the preparations include at least $1\times10^3$ RPE cells, $5\times10^3$ RPE cells, $1\times10^4$ RPE cells, $5\times10^4$ RPE cells, $1\times10^5$ RPE cells, $2\times10^5$ RPE cells, $3\times10^5$ RPE cells, $4\times10^5$ RPE cells, $5\times10^5$ RPE cells, $6\times10^5$ RPE cells, $7\times10^5$ RPE cells, $8\times10^5$ RPE cells, $9\times10^5$ RPE cells, $1\times10^6$ RPE cells, $5\times10^6$ RPE cells, $6\times10^6$ RPE cells, $7\times10^6$ RPE cells, $8\times10^6$ RPE cells, $9\times10^6$ RPE cells, $1\times10^7$ RPE cells, $5\times10^7$ RPE cells, $1\times10^8$ RPE cells, $1\times10^9$ RPE cells, or even more than $1\times10^9$ RPE cells.

In certain embodiments, the ES-derived RPE cells do not express ES cell markers. For example, expression of the ES cell genes Oct-4, nanog, and/or Rex-1 is approximately 100-1000 fold lower in RPE cells than in ES cells, as assessed by quantitative RT-PCR. Thus, in comparison to ES cells, RPE cells are substantially negative for Oct-4, nanog, and/or Rex-1 gene expression.

In certain embodiments, the ES-derived RPE cells express, at the mRNA and protein level, one or more of the following: RPE65, bestrophin, PEDF, CRALBP, Otx2, and MitF. In certain embodiments, RPE cells express two or more, three or more, four or more, five or more, or six of these markers. In certain embodiments, the RPE cells additionally or alternatively express, at the mRNA and protein level, one or more (1, 2, or 3) of the following: pax-2, pax6, and tyrosinase. In other embodiments, the level of maturity of the RPE cells is assessed by expression of one or more (1, 2, or 3) of pax-2, pax6, and tyrosinase.

In certain embodiments, the ES-derived RPE cells express, at the mRNA and/or protein level, one or more (1, 2, 3, 4, 5, 6, 7, 8, or 9) of the RPE-specific genes listed in Table 1 (pax-6, pax-2, RPE65, PEDF, CRALBP, bestrophin, mitF, Otx-2, and tyrosinase, as well as one or more (1, 2, 3, or 4) of the neuroretina genes listed in Table 1 (CHX10, NCAM, nestin, beta-tubulin). However, the RPE cells do not substantially express the ES cell specific genes Oct-4, nanog, and/or Rex-1 (e.g., expression of the ES cell specific genes is 100-1000 fold less in RPE cells, as determined by quantitative RT-PCR).

In certain embodiments, the ES-derived RPE cells express, at the mRNA and/or protein level, one or more (1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more than 48) of the genes listed in Table 2, and the expression of the one or more genes is increased in RPE cells relative to the level of expression (if any) in human ES cells. Alternatively or additionally, the ES-derived RPE cells express, at the mRNA and/or protein level one or more (1, 2, 3, 4, 5, 6, 7, 8, 9, 10, 11, 12, 13, 14, 15, 16, 17, 18, 19, 20, 21, 22, 23, 24, or more than 25) of the genes listed in Table 3, but the expression of the one or more genes is decreased (including decreased to nearly undetectable levels) in RPE cells relative to the level of expression in human ES cells.

In certain embodiments, the substantially purified preparation of RPE cells comprises RPE cells of differing levels of maturity (e.g., differentiated RPE cells and mature differentiated RPE cells). In such instances, there may be variability across the preparation with respect to expression of markers indicative of pigmentation. For example, although such RPE cells may have substantially the same expression of RPE65, PEDF, CRALBP, and bestrophin. The RPE cells may vary, depending on level of maturity, with respect to expression of one or more of pax-2, pax-6, mitF, and/or tyrosinase.

In certain embodiments, the ES-derived RPE cells are stable, terminally differentiated RPE cells that do not de-differentiate to a non-RPE cell type. In certain embodiments, the ES-derived RPE cells are functional RPE cells.

In certain embodiments, the ES-derived RPE cells are characterized by the ability to integrate into the retina upon corneal, sub-retinal, or other transplantation or administration into an animal.

The preparations are produced in compliance with GMP standards. As such, in certain embodiments, the preparations are GMP compliant preparations. In other embodiments, the preparations are substantially free of viral, bacterial, and/or fungal infection and contamination.

In certain embodiments, the preparations are cryopreserved for storage and future use. Thus, the invention provides cryopreserved preparations comprising substantially purified RPE cells. Cryopreserved preparations are formulated in excipients suitable to maintain cell viability during and following cryopreservation. In certain embodiments, the cryopreserved preparation comprises at least $1\times10^3$ RPE cells, $5\times10^3$ RPE cells, $1\times10^4$ RPE cells, $5\times10^4$ RPE cells, $1\times10^5$ RPE cells, $2\times10^5$ RPE cells, $3\times10^5$ RPE cells, $4\times10^5$ RPE cells, $5\times10^5$ RPE cells, $6\times10^5$ RPE cells, $7\times10^5$ RPE cells, $8\times10^5$ RPE cells, $9\times10^5$ RPE cells, $1\times10^6$ RPE cells, $5\times10^6$ RPE cells, $6\times10^6$ RPE cells, $7\times10^6$ RPE cells, $8\times10^6$ RPE cells, $9\times10^6$ RPE cells, $1\times10^7$ RPE cells, $5\times10^7$ RPE cells, $1\times10^8$ RPE cells, $1\times10^9$ RPE cells, or even more than $1\times10^9$ RPE cells. Cryopreserved preparations may have the same levels of purity with respect to non-RPE cells and/or with respect to RPE cells of varying levels of maturity as detailed above. In certain embodiments, at least 65% of the RPE cells in a cryopreserved preparation of RPE cells retain viability following thawing. In other embodiments, at least 70%, 75%, 80%, 85%, 90%, 81%, 92%, 93%, 94%, 95%, 96%, 97%, 98%, 99% or greater than 99% of the RPE cells in a cryopreserved preparation of RPE cells retain viability following thawing.

The RPE cells provided herein are human cells. Note, however, that the human cells may be used in human patients, as well as in animal models or animal patients. For example, the human cells may be tested in rat, dog, or non-human primate models of retinal degeneration. Additionally, the human cells may be used therapeutically to treat animals in need thereof, such as in a veterinary medical setting.

Preparations may be formulated as pharmaceutical preparations prepared in a pharmaceutically acceptable carrier or excipient. Preferred preparations are specifically formulated for administration to the eye (e.g., sub-retinal, corneal, ocular, etc.)

In certain embodiments of any of the foregoing, the RPE cells are derived from human pluripotent stem cells, such as human embryonic stem cells or human iPS cells. The invention contemplates that any of the preparations described herein may be derived from an appropriate human pluripotent stem cell.

Preparations including one or more of any of the foregoing features are contemplated.

The invention contemplates that any of the foregoing preparations of RPE cells, including substantially purified preparations and preparations have a particular minimal number of RPE cells, may be used in the treatment of any of the indications described herein. Further, RPE cells differentiated using any of the methods described herein may be used in the treatment of any of the indications described herein.

RPE Cell-Based Therapies

RPE cells and pharmaceutically preparations comprising RPE cells produced by the methods described herein and/or having the characteristics of RPE cell preparations described herein may be used for cell-based treatments in which RPE cells are needed or would improve treatment. The following section describes methods of using RPE cells provided by the present invention for treating various conditions that may benefit from RPE cell-based therapies. The particular treatment regimen, route of administration, and any adjuvant therapy will be tailored based on the particular condition, the severity of the condition, and the patient's overall health. Additionally, in certain embodiments, administration of RPE cells may be effective to fully restore any vision loss or other symptoms. In other embodiments, administration of RPE cells may be effective to reduce the severity of the symptoms and/or to prevent further degeneration in the patient's condition. The invention contemplates that administration of a preparation comprising RPE cells can be used to treat (including reducing the severity of the symptoms, in whole or in part) any of the foregoing or following conditions. Additionally, RPE cell administration may be used to help treat the symptoms of any injury to the endogenous RPE layer.

The invention contemplates that RPE cells, including preparations comprising RPE cells, derived using any of the methods described herein can be used in the treatment of any of the indications described herein. Further, the invention contemplates that any of the preparations comprising RPE cells described herein can be used in the treatment of any of the indications described herein.

Retinitis pigmentosa is a hereditary condition in which the vision receptors are gradually destroyed through abnormal genetic programming. Some forms cause total blindness at relatively young ages, where other forms demonstrate characteristic "bone spicule" retinal changes with little vision destruction. This disease affects some 1.5 million people worldwide. Two gene defects that cause autosomal recessive retinitis pigmentosa have been found in genes expressed exclusively in RPE. One is due to an RPE protein involved in vitamin A metabolism (cis retinaldehyde binding protein). The second involves another protein unique to RPE, RPE65. This invention provides methods and compositions for treating both of these forms of retinitis pigmentosa by administration of RPE cells.

In another embodiment, the present invention provides methods and compositions for treating disorders associated with retinal degeneration, including macular degeneration.

A further aspect of the present invention is the use of RPE cells for the therapy of eye diseases, including hereditary and acquired eye diseases. Examples of acquired or hereditary eye diseases are age-related macular degeneration, glaucoma and diabetic retinopathy.

Age-related macular degeneration (AMD) is the most common reason for legal blindness in western countries. Atrophy of the submacular retinal pigment epithelium and the development of choroidal neovascularizations (CNV) results secondarily in loss of central visual acuity. For the majority of patients with subfoveal CNV and geographic atrophy there is at present no treatment available to prevent loss of central visual acuity. Early signs of AMD are deposits (drusen) between retinal pigment epithelium and Bruch's membrane. During the disease there is sprouting of choroid vessels into the subretinal space of the macula. This leads to loss of central vision and reading ability.

Glaucoma is the name given to a group of diseases in which the pressure in the eye increases abnormally. This leads to restrictions of the visual field and to the general diminution in the ability to see. The most common form is primary glaucoma; two forms of this are distinguished: chronic obtuse-angle glaucoma and acute angle closure. Secondary glaucoma may be caused by infections, tumors or injuries. A third type, hereditary glaucoma, is usually derived from developmental disturbances during pregnancy. The aqueous humor in the eyeball is under a certain pressure which is necessary for the optical properties of the eye. This intraocular pressure is normally 15 to 20 millimeters of mercury and is controlled by the equilibrium between aqueous production and aqueous outflow. In glaucoma, the outflow of the aqueous humor in the angle of the anterior chamber is blocked so that the pressure inside the eye rises. Glaucoma usually develops in middle or advanced age, but hereditary forms and diseases are not uncommon in children and adolescents. Although the intraocular pressure is only slightly raised and there are moreover no evident symptoms, gradual damage occurs, especially restriction of the visual field. Acute angle closure by contrast causes pain, redness, dilation of the pupils and severe disturbances of vision. The cornea becomes cloudy, and the intraocular pressure is greatly increased. As the disease progresses, the visual field becomes increasingly narrower, which can easily be detected using a perimeter, an ophthalmologic instrument. Chronic glaucoma generally responds well to locally administered medicaments which enhance aqueous outflow. Systemic active substances are sometimes given to reduce aqueous production. However, medicinal treatment is not always successful. If medicinal therapy fails, laser therapy or conventional operations are used in order to create a new outflow for the aqueous humor. Acute glaucoma is a medical emergency. If the intraocular pressure is not reduced within 24 hours, permanent damage occurs.

Diabetic retinopathy arises in cases of diabetes mellitus. It can lead to thickening of the basal membrane of the vascular endothelial cells as a result of glycosilation of proteins. It is the cause of early vascular sclerosis and the formation of capillary aneurysms. These vascular changes lead over the course of years to diabetic retinopathy. The vascular changes cause hypoperfusion of capillary regions. This leads to lipid deposits (hard exudates) and to vasoproliferation. The clinical course is variable in patients with diabetes mellitus. In age-related diabetes (type II diabetes), capillary aneurysms appear first. Thereafter, because of the impaired capillary perfusion, hard and soft exudates and dot-like hemorrhages in the retinal parenchyma appear. In later stages of diabetic retinopathy, the fatty deposits are arranged like a corona around the macula (retinitis circinata). These changes are frequently accompanied by edema at the posterior pole of the eye. If the edema involves the macula there is an acute serious deterioration in vision. The main problem in type I diabetes is the vascular proliferation in the region of the fundus of the eye. The standard therapy is laser coagulation of the affected regions of the fundus of the eye. The laser coagulation is initially performed focally in the affected areas of the retina. If the exudates persist, the area of laser coagulation is extended. The center of the retina with the site of sharpest vision, that is to say the macula and the papillomacular bundle, cannot be coagulated because the procedure would result in destruction of the parts of the retina which are most important for vision. If proliferation has already occurred, it is often necessary for the foci to be very densely pressed on the basis of the proliferation. This entails destruction of areas of the retina. The result is a corresponding loss of visual field. In type I diabetes, laser coagulation in good time is often the only chance of saving patients from blindness.

In certain embodiments, the RPE cells of the invention may be used to treat disorders of the central nervous system. RPE cells may be transplanted into the CNS. To date, a number of different cell types have been employed in animal experiments or in patients with Parkinson's disease in clinical studies. Examples are fetal cells obtained from brains of human fetuses. Fetal cells from the ventral midbrain or dopaminergic neurons have already been transplanted in clinical studies on more than 300 patients with Parkinson's disease (for review, see Alexi T, Borlongan C V, Faull R L, Williams C E, Clark R G, Gluckman P D, Hughes P E (2000) (Neuroprotective strategies for basal ganglia degeneration: Parkinson's and Huntington's diseases. Prog Neurobiol 60: 409 470). A number of different cell types, including non-neuronal cells, e.g. cells from the adrenal cortex, Sertoli cells on the gonads or glomus cells from the carotid bodies, fibroblasts or astrocytes, have been used in patients with Parkinson's disease or in animal models with the aim of replacing dopamine spontaneously or after gene transfer (Alexi et al. 2000, supra). The survival rate of transplanted fetal dopaminergic neurons is 5 8%, which was enough to cause a slight improvement in the signs and symptoms (Alexi et al. 2000, supra).

In recent years, neuronal stem cells from brains of adult vertebrates have been isolated, expanded in vitro and reimplanted into the CNS, after which they differentiated into pure neurons. Their function in the CNS remains uncertain, however. Neuronal precursor cells have also been used for gene transfer (Raymon H K, Thode S, Zhou J, Friedman G C, Pardinas J R, Barrere C, Johnson R M, Sah D W (1999) Immortalized human dorsal root ganglion cells differentiate into neurons with nociceptive properties. J Neurosci 19: 5420 5428). Schwann cells which overexpressed NGF and GDNF had neuroprotective effects in models of Parkinsonism (Wilby M J, Sinclair S R, Muir E M, Zietlow R, Adcock K H, Horellou P, Rogers J H, Dunnett S B, Fawcett J W (1999) A glial cell line-derived neurotrophic factor-secreting clone of the Schwann cell line SCTM41 enhances survival and fiber outgrowth from embryonic nigral neurons grafted to the striatum and to the lesioned substantia nigra. J Neurosci 19: 2301 2312).

Another aspect of the present invention is therefore the use of pigment epithelial cells for the therapy of nerve diseases, in particular a disease of the nervous system, preferably of the CNS, especially of Parkinson's disease.

An example of a common disease of the CNS is Parkinson's disease which is a chronic degenerative disease of the brain. The disease is caused by degeneration of specialized neuronal cells in the region of the basal ganglia. The death of dopaminergic neurons results in reduced synthesis of dopamine, an important neurotransmitter, in patients with Parkinson's disease. The standard therapy is medical therapy with L-dopa. L-Dopa is metabolized in the basal ganglia to dopamine and there takes over the function of the missing endogenous neurotransmitter. However, L-dopa therapy loses its activity after some years.

Animal models of retinitis pigmentosa that may be treated or used to test the efficacy of the RPE cells produced using the methods described herein include rodents (rd mouse, RPE-65 knockout mouse, tubby-like mouse, RCS rat), cats (Abyssinian cat), and dogs (cone degeneration "cd" dog, progressive rod-cone degeneration "prcd" dog, early retinal degeneration "erd" dog, rod-cone dysplasia 1, 2 & 3 "rcd1, rcd2 & rcd3" dogs, photoreceptor dysplasia "pd" dog, and Briard "RPE-65" (dog)).

Another embodiment of the present invention is a method for the derivation of RPE lines or precursors to RPE cells that have an increased ability to prevent neovascularization. Such cells can be produced by aging a somatic cell from a patient such that telomerase is shortened where at least 10% of the normal replicative lifespan of the cell has been passed, then the use of said somatic cell as a nuclear transfer donor cell to create cells that overexpress angiogenesis inhibitors such as Pigment Epithelium Derived Factor (PEDF/EPC-1). Alternatively such cells may be genetically modified with exogenous genes that inhibit neovascularization.

The invention contemplates that preparations of RPE cells differentiated from human pluripotent stem cells (e.g., human embryonic stem cells, iPS cells, or other pluripotent stem cells) can be used to treat any of the foregoing diseases or conditions, as well as injuries of the endogenous RPE layer. These diseases can be treated with preparations of RPE cells comprising a mixture of differentiated RPE cells of varying levels of maturity, as well as with preparations of differentiated RPE cells that are enriched for mature differentiated RPE cells or differentiated RPE cells.

Modes of Administration

RPE cells of the invention may be administered topically, systemically, or locally, such as by injection (e.g., intravitreal injection), or as part of a device or implant (e.g., a sustained release implant). For example, the cells of the present invention may be transplanted into the subretinal space by using vitrectomy surgery.

Depending on the method of administration, RPE cells can be added to buffered and electrolyte balanced aqueous solutions, buffered and electrolyte balanced aqueous solutions with a lubricating polymer, mineral oil or petrolatum-based ointment, other oils, liposomes, cylcodextrins, sustained release polymers or gels. These preparations can be administered topically to the eye 1 to 6 times per day for a period up to the lifetime of the patient.

In certain embodiments, methods of treating a patient suffering from a condition associated with retinal degeneration comprise administering a composition of the invention locally (e.g., by intraocular injection or insertion of a sustained release device that releases a composition of the invention), by topical means or by systemic administration (e.g., by routes of administration that allow in vivo systemic absorption or accumulation of drugs in the blood stream followed by distribution throughout the entire body, including, without limitation, by intravenous, subcutaneous, intraperitoneal, inhalation, oral, intrapulmonary and intramuscular routes). Intraocular administration of compositions of the invention includes, for example, delivery into the vitreous body, transcorneally, sub-conjunctival, juxtascleral, posterior scleral, and sub-tenon portions of the eye. See, for example, U.S. Pat. Nos. 6,943,145; 6,943,153; and 6,945,971, the contents of which are hereby incorporated by reference.

RPE cells of the invention may be delivered in a pharmaceutically acceptable ophthalmic formulation by intraocular injection. When administering the formulation by intravitreal injection, for example, the solution should be concentrated so that minimized volumes may be delivered. Concentrations for injections may be at any amount that is effective and non-toxic, depending upon the factors described herein. In some embodiments, RPE cells for treatment of a patient are formulated at doses of about $10^4$ cells/mL. In other embodiments, RPE cells for treatment of a patient are formulated at doses of about $10^5$, $10^6$, $10^7$, $10^8$, $10^9$, or $10^{10}$ cells/mL.

RPE cells may be formulated for delivery in a pharmaceutically acceptable ophthalmic vehicle, such that the composition is maintained in contact with the ocular surface for a sufficient time period to allow the cells to penetrate the affected regions of the eye, as for example, the anterior chamber, posterior chamber, vitreous body, aqueous humor, vitreous humor, cornea, iris/ciliary, lens, choroid, retina, sclera, suprachoridal space, conjunctiva, subconjunctival space, episcleral space, intracorneal space, epicorneal space, pars plana, surgically-induced avascular regions, or the macula. Products and systems, such as delivery vehicles, comprising the agents of the invention, especially those formulated as pharmaceutical compositions—as well as kits comprising such delivery vehicles and/or systems—are also envisioned as being part of the present invention.

In certain embodiments, a therapeutic method of the invention includes the step of administering RPE cells of the invention as an implant or device. In certain embodiments, the device is bioerodible implant for treating a medical condition of the eye comprising an active agent dispersed within a biodegradable polymer matrix, wherein at least about 75% of the particles of the active agent have a diameter of less than about 10 µm. The bioerodible implant is sized for implantation in an ocular region. The ocular region can be any one or more of the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina. The biodegradable polymer can be, for example, a poly(lactic-co-glycolic)acid (PLGA) copolymer. In certain embodiments, the ratio of lactic to glycolic acid monomers in the polymer is about 25/75, 40/60, 50/50, 60/40, 75/25 weight percentage, more preferably about 50/50. Additionally, the PLGA copolymer can be about 20, 30, 40, 50, 60, 70, 80 to about 90 percent by weight of the bioerodible implant. In certain preferred embodiments, the PLGA copolymer can be from about 30 to about 50 percent by weight, preferably about 40 percent by weight of the bioerodible implant.

The volume of composition administered according to the methods described herein is also dependent on factors such as the mode of administration, number of RPE cells, age and weight of the patient, and type and severity of the disease being treated. For example, if administered orally as a liquid, the liquid volume comprising a composition of the invention may be from about 0.5 milliliters to about 2.0 milliliters, from about 2.0 milliliters to about 5.0 milliliters, from about 5.0 milliliters to about 10.0 milliliters, or from about 10.0 milliliters to about 50.0 milliliters. If administered by injection, the liquid volume comprising a composition of the invention may be from about 5.0 microliters to about 50 microliters, from about 50 microliters to about 250 microliters, from about 250 microliters to about 1 milliliter, from about 1 milliliter to about 5 milliliters, from about 5 milliliters to about 25 milliliters, from about 25 milliliters to about 100 milliliters, or from about 100 milliliters to about 1 liter.

If administered by intraocular injection, RPE cells can be delivered one or more times periodically throughout the life of a patient. For example RPE cells can be delivered once per year, once every 6-12 months, once every 3-6 months, once every 1-3 months, or once every 1-4 weeks. Alternatively, more frequent administration may be desirable for certain conditions or disorders. If administered by an implant or device, RPE cells can be administered one time, or one or more times periodically throughout the lifetime of the patient, as necessary for the particular patient and disorder or condition being treated. Similarly contemplated is a therapeutic regimen that changes over time. For example, more frequent treatment may be needed at the outset (e.g., daily or weekly treatment). Over time, as the patient's condition improves, less frequent treatment or even no further treatment may be needed.

In certain embodiments, patients are also administered immunosuppressive therapy, either before, concurrently with, or after administration of the RPE cells. Immunosuppressive therapy may be necessary throughout the life of the patient, or for a shorter period of time.

In certain embodiments, RPE cells of the present invention are formulated with a pharmaceutically acceptable carrier. For example, RPE cells may be administered alone or as a component of a pharmaceutical formulation. The subject compounds may be formulated for administration in any convenient way for use in human medicine. In certain embodiments, pharmaceutical compositions suitable for parenteral administration may comprise the RPE cells, in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like in the compositions. In addition, prolonged absorption of the injectable pharmaceutical form may be brought about by the inclusion of one or more agents that delay absorption, such as, e.g., aluminum monostearate and gelatin.

When administered, the therapeutic composition for use in this invention is, of course, in a pyrogen-free, physiologically acceptable form. Further, the composition may desirably be encapsulated or injected in a viscous form into the vitreous humor for delivery to the site of retinal or choroidal damage.

Engineering MHC Genes in Human Embryonic Stem Cells to Obtain Reduced-Complexity RPE Cells The human embryonic stem cells used as the starting point for the method of producing RPE cells of this invention may also be derived from a library of human embryonic stem cells, each of which is hemizygous or homozygous for at least one MHC allele present in a human population. In certain embodiments, each member of said library of stem cells is hemizygous or homozygous for a different set of MHC alleles relative to the remaining members of the library. In certain embodiments, the library of stem cells is hemizygous or homozygous for all MHC alleles that are present in a human population. In the context of this invention, stem cells that are homozygous for one or more histocompatibility antigen genes include cells that are nullizygous for one or more (and in some embodiments, all) such genes. Nullizygous for a genetic locus means that the gene is null at that locus, i.e., both alleles of that gene are deleted or inactivated. Stem cells that are nullizygous for all MHC genes may be produced by standard methods known in the art, such as, for example, gene targeting and/or loss of heterozygosity (LOH). See, for example, United States patent publications US 20040091936, US 20030217374 and US 20030232430, and U.S. provisional application No. 60/729,173, the disclosures of all of which are hereby incorporated by reference herein.

Accordingly, the present invention relates to methods of obtaining RPE cells, including a library of RPE cells, with reduced MHC complexity. RPE cells with reduced MHC complexity will increase the supply of available cells for therapeutic applications as it will eliminate the difficulties associated with patient matching. Such cells may be derived from stem cells that are engineered to be hemizygous or homozygous for genes of the MHC complex.

A human ES cell may comprise modifications to one of the alleles of sister chromosomes in the cell's MHC complex. A variety of methods for generating gene modifications, such as gene targeting, may be used to modify the genes in the MHC complex. Further, the modified alleles of the MHC complex in the cells may be subsequently engineered to be homozygous so that identical alleles are present on sister chromosomes. Methods such as loss of heterozygosity (LOH) may be utilized to engineer cells to have homozygous alleles in the MHC complex. For example, one or more genes in a set of MHC genes from a parental allele can be targeted to generate hemizygous cells. The other set of MHC genes can be removed by gene targeting or LOH to make a null line. This null line can be used further as the embryonic cell line in which to drop arrays of the HLA genes, or individual genes, to make a hemizygous or homozygous bank with an otherwise uniform genetic background.

In one aspect, a library of ES cell lines, wherein each member of the library is homozygous for at least one HLA gene, is used to derive RPE cells according to the methods of the present invention. In another aspect, the invention provides a library of RPE cells (and/or RPE lineage cells), wherein several lines of ES cells are selected and differentiated into RPE cells. These RPE cells and/or RPE lineage cells may be used for a patient in need of a cell-based therapy.

Accordingly, certain embodiments of this invention pertain to a method of administering human RPE cells that have been derived from reduced-complexity embryonic stem cells to a patient in need thereof. In certain embodiments, this method comprises the steps of: (a) identifying a patient that needs treatment involving administering human RPE cells to him or her; (b) identifying MHC proteins expressed on the surface of the patient's cells; (c) providing a library of human RPE cells of reduced MHC complexity made by the method for producing RPE cells of the present invention; (d) selecting the RPE cells from the library that match this patient's MHC proteins on his or her cells; (e) administering any of the cells from step (d) to said patient. This method may be performed in a regional center, such as, for example, a hospital, a clinic, a physician's office, and other health care facilities. Further, the RPE cells selected as a match for the patient, if stored in small cell numbers, may be expanded prior to patient treatment.

Other Commercial Applications and Methods

Certain aspects of the present invention pertain to the production of RPE cells to reach commercial quantities. In particular embodiments, RPE cells are produced on a large scale, stored if necessary, and supplied to hospitals, clinicians or other healthcare facilities. Once a patient presents with an indication such as, for example, Stargardt's macular dystrophy, age related macular degeneration, or retinitis pigmentosa, RPE cells can be ordered and provided in a timely manner. Accordingly, the present invention relates to methods of producing RPE cells to attain cells on a commercial scale, cell preparations comprising RPE cells derived from said methods, as well as methods of providing (i.e., producing, optionally storing, and selling) RPE cells to hospitals and clinicians.

Accordingly certain aspects of the present invention relate to methods of production, storage, and distribution of RPE cells produced by the methods disclosed herein. Following RPE production, RPE cells may be harvested, purified and optionally stored prior to a patient's treatment. RPE cells may optionally be patient specific or specifically selected based on HLA or other immunologic profile.

Thus in particular embodiments, the present invention provides methods of supplying RPE cells to hospitals, healthcare centers, and clinicians, whereby RPE cells produced by the methods disclosed herein are stored, ordered on demand by a hospital, healthcare center, or clinician, and administered to a patient in need of RPE cell therapy. In alternative embodiments, a hospital, healthcare center, or clinician orders RPE cells based on patient specific data, RPE cells are produced according to the patient's specifications and subsequently supplied to the hospital or clinician placing the order.

In certain embodiments, the method of differentiating RPE cells from human embryonic stem cells is conducted in accordance with Good Manufacturing Practices (GMP). In certain embodiments, the initial derivation or production of human embryonic stem cells is also conducted in accordance with Good Manufacturing Practices (GMP). The cells may be tested at one or more points throughout the differentiation protocol to ensure, for example, that there is no viral, bacterial, or fungal infection or contamination in the cells or culture medium. Similarly, the human embryonic stem cells used as starting material may be tested to ensure that there is no viral, bacterial, or fungal infection or contamination.

In certain embodiments, the production of differentiated RPE cells or mature differentiated RPE cells is scaled up for commercial use. For example, the method can be used to produce at least $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, or $1\times10^{10}$ RPE cells.

Further aspects of the invention relate to a library of RPE cells that can provide matched cells to potential patient recipients. Accordingly, in one embodiment, the invention provides a method of conducting a pharmaceutical business, comprising the step of providing RPE cell preparations that are homozygous for at least one histocompatibility antigen, wherein cells are chosen from a bank of such cells comprising a library of RPE cells that can be expanded by the methods disclosed herein, wherein each RPE cell preparation is hemizygous or homozygous for at least one MHC allele present in the human population, and wherein said bank of RPE cells comprises cells that are each hemizygous or homozygous for a different set of MHC alleles relative to the other members in the bank of cells. As mentioned above, gene targeting or loss of heterozygosity may be used to generate the hemizygous or homozygous MHC allele stem cells used to derive the RPE cells. In one embodiment, after a particular RPE cell preparation is chosen to be suitable for a patient, it is thereafter expanded to reach appropriate quantities for patient treatment. Methods of conducting a pharmaceutical business may also comprise establishing a distribution system for distributing the preparation for sale or may include establishing a sales group for marketing the pharmaceutical preparation.

Other aspects of the invention relate to the use of the RPE cells of the present invention as a research tool in settings such as a pharmaceutical, chemical, or biotechnology company, a hospital, or an academic or research institution. Such uses include the use of RPE cells differentiated from embryonic stem cells in screening assays to identify, for example, agents that can be used to promote RPE survival in vitro or in vivo, or that can be used to promote RPE maturation. Identified agents can be studied in vitro or in animal models to evaluate, for example, their potential use alone or in combination with RPE cells.

The present invention also includes methods of obtaining human ES cells from a patient and then generating and expanding RPE cells derived from the ES cells. These RPE cells may be stored. In addition, these RPE cells may be used to treat the patient from which the ES were obtained or a relative of that patient.

As the methods and applications described above relate to treatments, pharmaceutical preparations, and the storing of RPE cells, the present invention also relates to solutions of RPE cells that are suitable for such applications. The present invention accordingly relates to solutions of RPE cells that are suitable for injection into a patient. Such solutions may comprise cells formulated in a physiologically acceptable liquid (e.g., normal saline, buffered saline, or a balanced salt solution). The number of cells in the solution may be at least about $10^2$ and less than about $10^9$ cells. In other embodiments, the number of cells in the solution may range from about $10^1$, $10^2$, $5\times10^2$, $10^3$, $5\times10^3$, $10^4$, $10^5$, $10^6$, $10^7$, or $10^8$ to about $5\times10^2$, $10^3$, $5\times10^3$, $10^4$, $10^5$, $10^6$, $10^7$, $10^8$, or $10^9$, where the upper and lower limits are selected independently, except that the lower limit is always less than the upper limit. Further, the cells may be administered in a single or in multiple administrations.

Cells provided by the methods described herein may be used immediately or may be frozen and cryopreserved for days or years. Thus, in one embodiment, the present invention provides a cryopreserved preparation of RPE cells, wherein said cryopreserved preparation comprises at least about $10^1$, $10^2$, $5\times10^2$, $10^3$, $5\times10^3$, $10^4$, $5\times10^4$, $10^5$, $5\times10^5$, or $10^6$ Cryopreserved preparations may further comprise at least about $5\times10^6$, $10^7$, $5\times10^7$, $10^8$, $15\times0^8$, $10^9$, $5\times10^9$, or $10^{10}$ cells. Similarly provided are methods of cryopreserving RPE cells. RPE cells may be cryopreserved immediately following differentiation, following in vitro maturation, or after some period of time in culture. The RPE cells in the preparations may comprise a mixture of differentiated RPE cells and mature RPE cells.

Other Pluripotent Cells

The foregoing discussion focuses on the use of human embryonic stem cells as the starting material for making unique RPE cells, as well as preparations and methods of using RPE cells differentiated from human embryonic stem cells. However, the methods and uses detailed above can similarly be used to generate RPE cells (and suitable preparations) using other types of human pluripotent stem cells as starting material. Accordingly, the invention contemplates that any of the foregoing or following aspects and embodiments of the invention can be similarly applied to methods and uses of RPE cells differentiated from other types of human pluripotent stem cells. Of particular note, given that induced pluripotent stem (iPS) cells have the characteristics of embryonic stem cells, such cells can be used to produce RPE cells that are identical or substantially identical to RPE cells differentiated from embryonic stem cells.

As used herein, the term "pluripotent stem cells" includes embryonic stem cells, embryo-derived stem cells, and induced pluripotent stem cells, regardless of the method by which the pluripotent stem cells are derived. Pluripotent stem cells are defined functionally as stem cells that: (a) are capable of inducing teratomas when transplanted in immunodeficient (SCID) mice; (b) are capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase, SSEA-3 surface antigen, SSEA-4 surface antigen, nanog, TRA-1-60, TRA-1-81, SOX2, REX1, etc). Exemplary pluripotent stem cells can be generated using, for example, methods known in the art. Exemplary pluripotent stem cells include embryonic stem cells derived from the ICM of blastocyst stage embryos, as well as embryonic stem cells derived from one or more blastomeres of a cleavage stage or morula stage embryo (optionally without destroying the remainder of the embryo). Such embryonic stem cells can be generated from embryonic material produced by fertilization or by asexual means, including somatic cell nuclear transfer (SCNT), parthenogenesis, cellular reprogramming, and androgenesis. Further exemplary pluripotent stem cells include induced pluripotent stem cells (iPS cells) generated by reprogramming a somatic cell by expressing or inducing the expression of a combination of factors (herein referred to as reprogramming factors). iPS cells can be generated using fetal, postnatal, newborn, juvenile, or adult somatic cells. In certain embodiments, factors that can be used to reprogram somatic cells to pluripotent stem cells include, for example, a combination of Oct4 (sometimes referred to as Oct 3/4), Sox2, c-Myc, and Klf4. In other embodiments, factors that can be used to reprogram somatic cells to pluripotent stem cells include, for example, a combination of Oct 4, Sox2, Nanog, and Lin28. In other embodiments, somatic cells are reprogrammed by expressing at least 2 reprogramming factors, at least three reprogramming factors, or four reprogramming factors. In other embodiments, additional reprogramming factors are identified and used alone or in combination with one or more known reprogramming factors to reprogram a somatic cell to a pluripotent stem cell.

Embryonic stem cells are one example of pluripotent stem cells. Another example are induced pluripotent stem (iPS) cells.

In certain embodiments, the pluripotent stem cell is an embryonic stem cell or embryo-derived cell. In other embodiments, the pluripotent stem cell is an induced pluripotent stem cell. In certain embodiments, the pluripotent stem cell is an induced pluripotent stem cell produced by expressing or inducing the expression of one or more reprogramming factors in a somatic cell. In certain embodiments, the somatic cell is a fibroblast, such as a dermal fibroblast, synovial fibroblast, or lung fibroblast. In other embodiments, the somatic cell is not a fibroblast, but rather is a non-fibroblastic somatic cell. In certain embodiments, the somatic cell is reprogrammed by expressing at least two reprogramming factors, at least three reprogramming factors, or four reprogramming factors. In other embodiments, the somatic cell is reprogrammed by expressing at least four, at least five, or at least six reprogramming factors. In certain embodiments, the reprogramming factors are selected from Oct 3/4, Sox2, Nanog, Lin28, c-Myc, and Klf4. In other embodiments, the set of reprogramming factors expressed includes at least one, at least two, at least three, or at least four of the foregoing list of reprogramming factors, and optionally includes one or more other reprogramming factors. In certain embodiments, expression of at least one, at least two, at least three, or at least four of the foregoing or other reprogramming factors is induced by contacting the somatic cells with one or more agents, such as a small organic molecule agents, that induce expression of one or more reprogramming factors. In certain embodiments, the somatic cell is reprogramming using a combinatorial approach wherein one or more reprogramming factor is expressed (e.g., using a viral vector, plasmid, and the like) and the expression of one or more reprogramming factor is induced (e.g., using a small organic molecule.).

In certain embodiments, reprogramming factors are expressed in the somatic cell by infection using a viral vector, such as a retroviral vector or a lentiviral vector. In other embodiments, reprogramming factors are expressed in the somatic cell using a non-integrative vector, such as an episomal plasmid. When reprogramming factors are expressed using non-integrative vectors, the factors can be expressed in the cells using electroporation, transfection, or transformation of the somatic cells with the vectors.

In certain embodiments, the pluripotent stem cells are generated from somatic cells, and the somatic cells are selected from embryonic, fetal, neonatal, juvenile, or adult cells.

Methods for making iPS cells by expressing or inducing the expression of reprogramming factors are known in the art. Briefly, somatic cells are infected, transfected, or otherwise transduced with expression vectors expressing reprogramming factors. In the case of mouse, expression of four factors (Oct3/4, Sox2, c-myc, and Klf4) using integrative viral vectors was sufficient to reprogram a somatic cell. In the case of humans, expression of four factors (Oct3/4, Sox2, Nanog, and Lin28) using integrative viral vectors was sufficient to reprogram a somatic cell. However, expression (or induction of expression) of fewer factors or other reprogramming factors may also be sufficient. Additionally, the use of integrative vectors is only one mechanism for expressing reprogramming factors in the cells. Other methods including, for example, the use of non-integrative vectors can be used.

In certain embodiments, expression of at least one, at least two, at least three, or at least four of the foregoing or other reprogramming factors is induced by contacting the somatic cells with one or more agents, such as a small organic molecule agents, that induce expression of one or more reprogramming factors. In certain embodiments, the somatic cell is reprogramming using a combinatorial approach wherein one or more reprogramming factor is expressed (e.g., using a viral vector, plasmid, and the like) and the expression of one or more reprogramming factor is induced (e.g., using a small organic molecule.).

Once the reprogramming factors are expressed in the cells, the cells are cultured. Over time, cells with ES characteristics appear in the culture dish. The cells can be picked and subcultured based on, for example, ES morphology, or based on expression of a selectable or detectable marker. The cells are cultured to produce a culture of cells that look like ES cells. These cells are putative iPS cells.

To confirm the pluripotency of the iPS cells, the cells can be tested in one or more assays of pluripotency. For examples, the cells can be tested for expression of ES cell markers; the cells can be evaluated for ability to produce teratomas when transplanted into SCID mice; the cells can be evaluated for ability to differentiate to produce cell types of all three germ layers.

Once pluripotent iPS cells are obtained (either freshly derived or from a bank or stock of previously derived cells), such cells can be used to make RPE cells.

In certain embodiments, the making of iPS cells is an initial step in the production of RPE cells. In other embodiments, previously derived iPS cells are used. In certain embodiments, iPS cells are specifically generated using material from a particular patient or matched donor with the goal of generating tissue-matched RPE cells. In certain embodiments, the iPS cells are universal donor cells that are not substantially immunogenic.

The present invention will now be more fully described with reference to the following examples, which are illustrative only and should not be considered as limiting the invention described above.

EXAMPLES

The invention now being generally described, it will be more readily understood by reference to the following examples, which are included merely for purposes of illustration of certain aspects and embodiments of the present invention, and are not intended to limit the invention.

The pluripotency of embryonic stem cells is maintained in-part by the delicate reciprocal balance of the two transcription factors Oct4 (Pou5f1) and Nanog. During ES cell differentiation, the expression of these genes is downregulated, and recent evidence has suggested hypermethylation of the genes encoding these proteins to be responsible. Loss of the expression of either or both of these genes results in transcriptional activation of genes associated with cellular differentiation.

The retinal pigmented epithelium (RPE) develops from the neuroectoderm and is located adjacent to the neural retina and choroid, providing a barrier between the vascular system and the retina. The data provided herein indicates that RPE cells are genetically and functionally distinguished from surrounding photoreceptors after terminal differentiation, although the cells may share a common progenitor.

This model indicates that elements unique to our culture method claims act through FGF, EGF, WNT4, TGF-beta, and/or oxidative stress to signal MAP-Kinase and potential C-Jun terminal Kinase pathways to induce the expression of the Paired-box 6 (PAX6) transcription factor. PAX6 acts synergistically with PAX2 to terminally differentiate mature RPE via the coordination of Mit-F and Otx2 to transcribe RPE-specific genes such as Tyrosinase (Tyr), and downstream targets such as RPE-65, Bestrophin, CRALBP, and PEDF.

Figure 3:
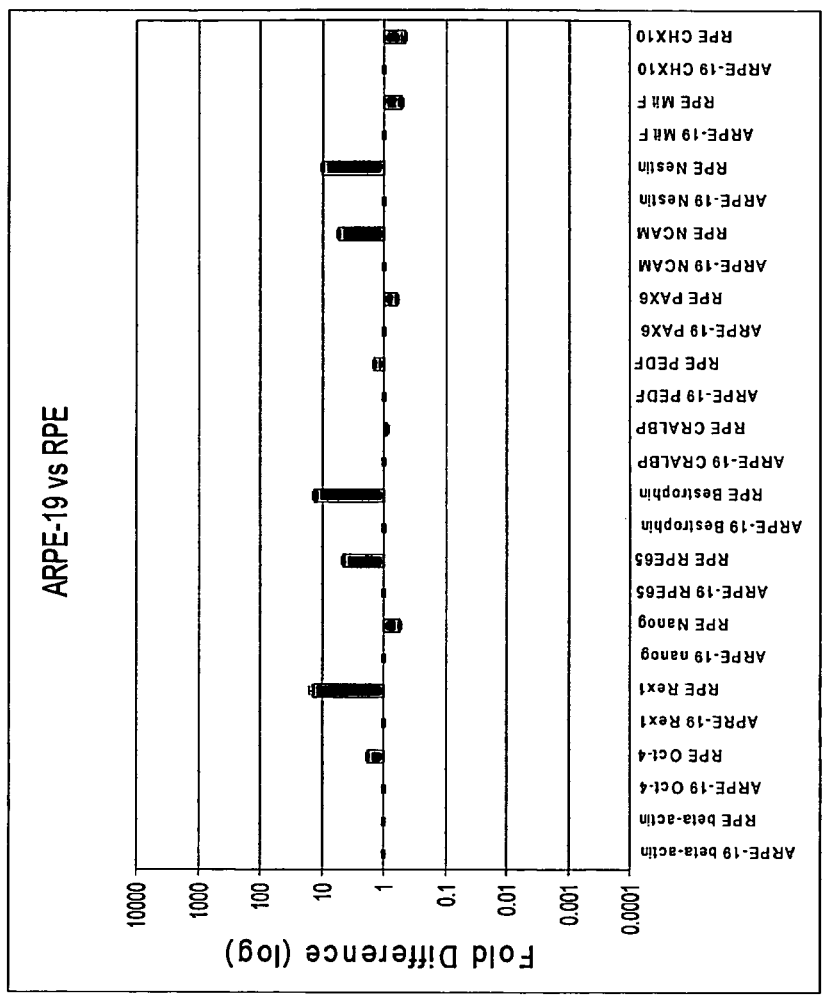
FIG. 3 is a graph showing gene expression comparison of ARPE-19 cells (a previously derived RPE cell line) and human embryonic stem cell-derived RPE cells by quantitative, Real-Time, Reverse Transcription PCR (qPCR).
Figure 4:
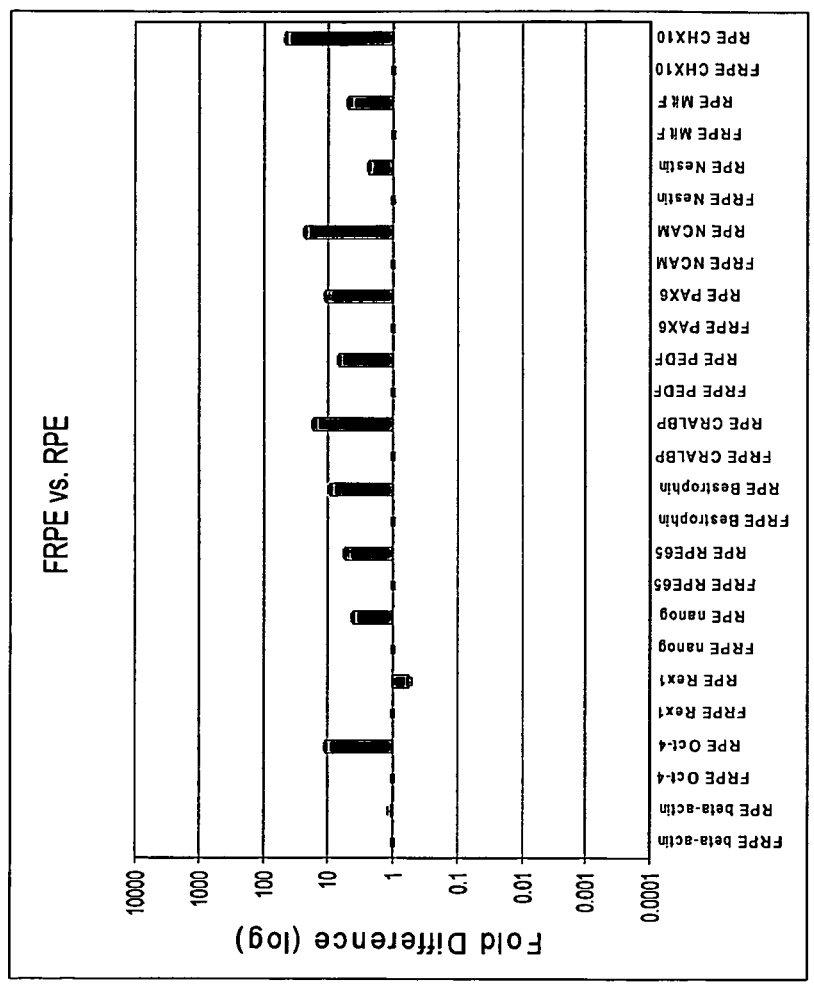
FIG. 4 is a graph showing gene expression comparison of fetal RPE cells and human embryonic stem cell-derived RPE cells by quantitative, Real-Time, Reverse Transcription PCR (qPCR).
Figure 5:
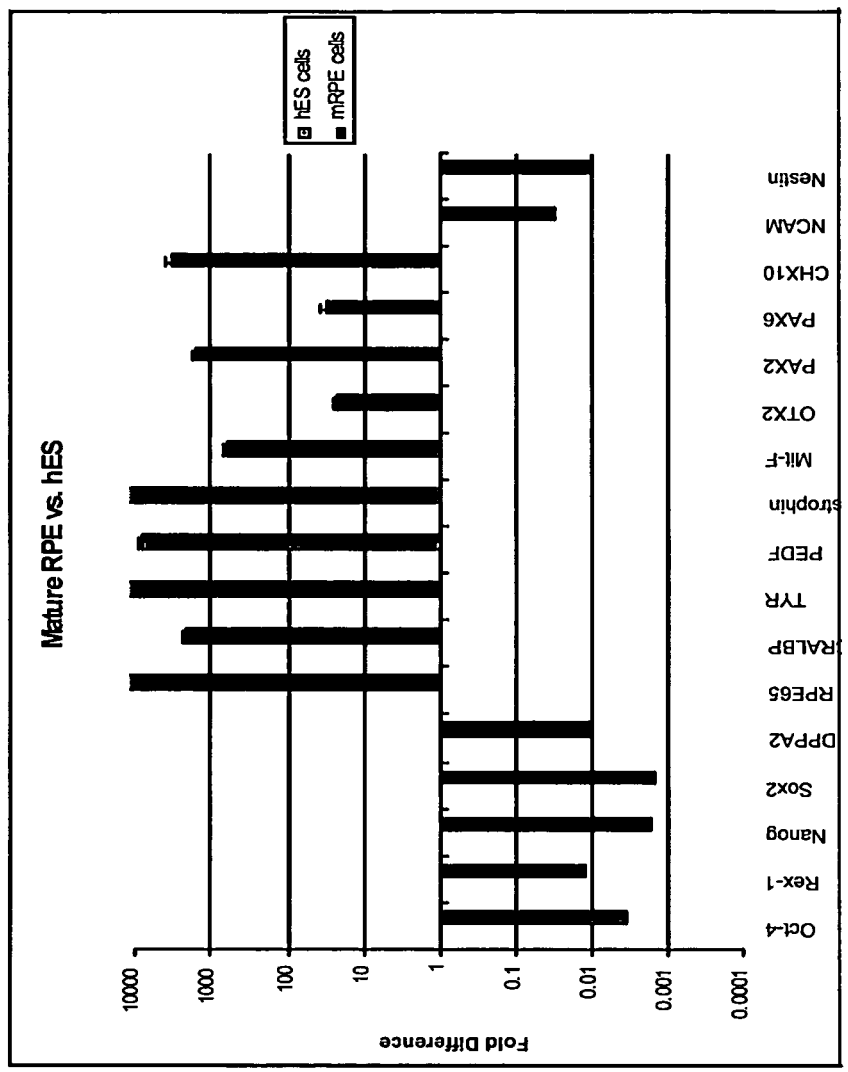
FIG. 5 is a graph showing gene expression comparison of mature RPE cells and hES cells by quantitative, Real-Time, Reverse Transcription PCR (qPCR).
Figure 6:
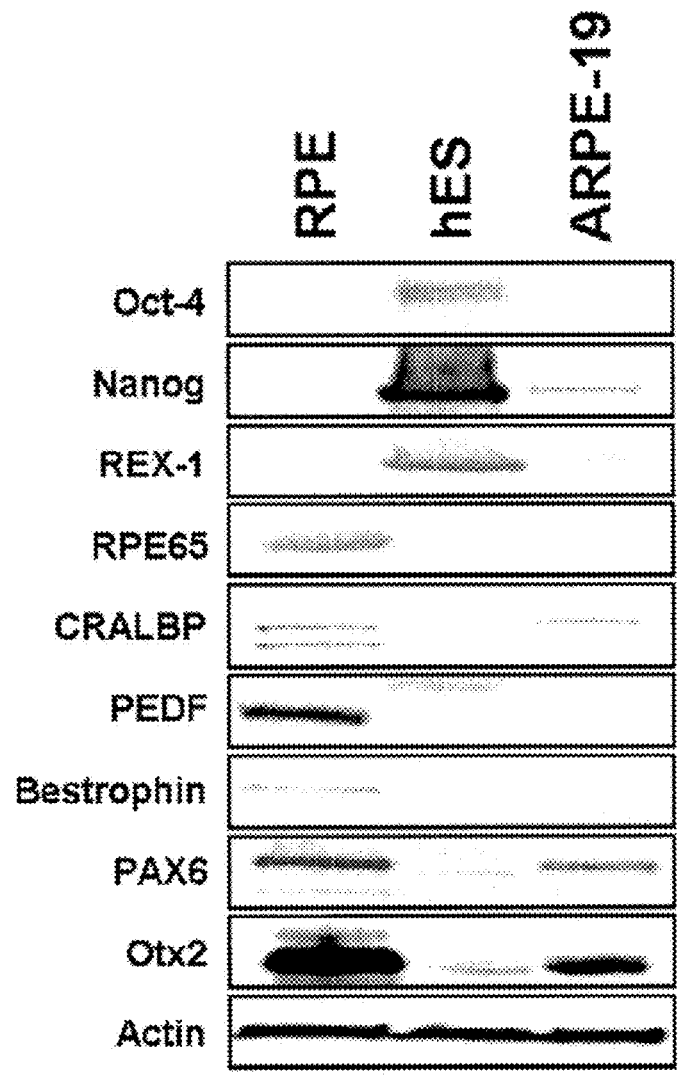
FIG. 6 is a photomicrograph showing Western Blot analysis of hES-specific and RPE-specific markers. Embryonic stem cell-derived RPE cells (lane 1) derived from hES cells (lane 2) did not express the hES-specific proteins Oct-4, Nanog, and Rex-1. However, embryonic stem cell-derived RPE cells express RPE-specific proteins included RPE65, CRALBP, PEDF, Bestrophin, PAX6, and Otx2. Actin was used as protein loading control.

In order to characterize developmental stages during the human embryonic stem cell (hESc) differentiation process into retinal pigmented epithelium (RPE), several assays were used to identify the expression levels of genes key to each representative stage of development. It was discovered that several genes were uniquely expressed as mRNA and protein in RPE cells. For instance, it was discovered that PAX6 acts with PAX2 to terminally differentiate mature RPE cells via coordination of Mit-F and Otx2 to transcribe RPE-specific genes such as Tyrosinase (Tyr), and downstream targets such as RPE-65, Bestrophin, CRALBP, and PEDF. Importantly, the RPE-specific signature of mRNA and protein expression was not only unique from hES cells, but also from fetal RPE and ARPE-19 cells. The RPE cells described herein expressed multiple genes that were not expressed in hES cells, fetal RPE cells, or ARPE-19 cells (FIGS. 3, 4, and 6). The unique expression of mRNA and proteins in the RPE cells of the invention constitutes a set of markers that make these RPE cells distinct from cells in the art, such as hES cells, ARPE-19 cells, and fetal RPE cells.

Example 1: RPE Differentiation and Culture

Cryopreserved hES cells were thawed and placed into suspension culture on Lo-bind Nunclon Petri dishes in MDBK-Growth Medium (Sigma—SAFC Biosciences) or OptimPro SFM (Invitrogen) supplemented with L-Glutamine, Penicillin/Streptomycin, and B-27 supplement. The hES cells had been previously derived from single blastomeres biopsied from early cleavage stage human embryos. The remainder of the human embryo was not destroyed. Two hES cell line derived from single blastomeres were used—MA01 and MA09. The cells were cultured for 7-14 days as embryoid bodies (EBs).

After 7-14 days, the EBs were plated onto tissue culture plates coated with gelatin from porcine skin. The EBs were grown as adherent cultures for an additional 14-28 days in MDBK-Growth Medium or OptimPro SFM supplemented with L-Glutamine, and Penicillin/Streptomycin, without B-27 supplement.

From amongst the cells in the adherent culture of EBs, RPE cells become visible and are recognized by their cobblestone cellular morphology and emergence of pigmentation.

Example 2: RPE Isolation and Propagation

As differentiated RPE cells continue to appear in the adherent cultures, clusters of differentiated RPEs become visibly noticeable based on cell shape. Frozen collagenase IV (20 mg/ml) was thawed and diluted to 7 mg/ml. The collagenase IV was applied to the adherent culture containing RPE clusters (1.0 ml to each well in a 6-well plate). Over approximately 1-3 hours, the collagenase IV dissociated the cell clusters. By dissociating the RPE clusters from other cells in the culture, an enriched suspension of RPE cells was obtained. The enriched RPE cell suspension was removed from the culture plate and transferred to a 100 mm tissue culture dish with 10 ml of MEF medium. Pigmented clumps are transferred with a stem cell cutting tool (Swemed-Vitrolife) to a well of a 6-well plate containing 3 ml of MEF media. After all clumps have been picked up, the suspension of pigmented cells is transferred to a 15 ml conical tube containing 7 ml of MEF medium and centrifuged at 1000 rpm for five minutes. The supernatant is removed. 5 ml of a 1:1 mixture of 0.25% trypsin and cell dissociation buffer is added to the cells. The cells are incubated for 10 minutes at 37° C. The cells are dispersed by pipetting in a 5 ml pipette until few clumps are remaining. 5 ml of MEF medium is added to the cells and the cells centrifuged at 1000 rpm for 5 minutes. The supernatant is removed and the cells are plated on gelatin coated plates with a split of 1:3 of the original culture in EGM-2 culture medium (Cambrex).

The culture of RPE cells was expanded by continued culture in EGM-2 medium. The cells were passaged, as necessary, at a 1:3 to 1:6 ratio using a 1:1 mixture of 0.25% trypsin EDTA and Cell Dissociation Buffer.

To enrich for mature differentiated RPE cells, the cells were grown to near confluence in EGM-2. The medium was then changed to MDBK-MM (SAFC Biosciences) to help further promote maturation of the RPE cells.

Example 3: RPE-Specific mRNA Expression Measured by Quantitative, Real-Time, Reverse Transcription PCR (qPCR)

In order to characterize developmental stages during the human embryonic stem cell (hES) differentiation process into retinal pigmented epithelium (RPE) several assays have been employed to identify the expression levels of genes key to each representative stage of development. qPCR was developed to provide a quantitative and relative measurement of the abundance of cell type-specific mRNA transcripts of interest in the RPE differentiation process. qPCR was used to determine genes that are uniquely expressed in human embryonic stem cells, in neuroretinal cells during eye development, and in RPE cells differentiated from human embryonic stem cells. The genes for each cell type are listed below in Table 1.

TABLE 1

Genes specific to hES, neuroretina/eye, and hRPE cells

| hESc-Specific | Neuroectoderm/Neuroretina | RPE-Specific Genes |
|---|---|---|
| Oct-4 (POU5F1) | CHX10 | PAX-6 |
| Nanog | NCAM | PAX-2 |
| Rex-1 | Nestin | RPE-65 |
| TDGF-1 | Beta-Tubulin | PEDF |
| SOX-2 | | CRALBP |
| DPPA-2 | | Bestrophin |
| | | MitF |
| | | Otx-2 |
| | | Tyr |

It was determined that hES-specific genes included Oct-4 (POU5F1), Nanog, Rex-1, TDGF-1, SOX-2, and DPPA-2. Genes specific to neural ectoderm/neural retina include CHX10, NCAM, Nestin, and Beta-Tubulin. By contrast, RPE cells differentiated from human embryonic stem cells were found to uniquely express PAX-6, PAX-2, RPE-65, PEDF, CRALBP, Bestrophin, MitF, Otx-2, and Tyr by qPCR measurement.

As evident from the qPCR data, hES-specific genes are grossly downregulated (near 1000-fold) in RPE cells derived from hES, whereas genes specific for RPE and neuroectoderm are vastly upregulated (approximately 100-fold) in RPE cells derived from hES.

In addition, qPCR analysis of fully mature RPE demonstrated a high level expression of the RPE-specific markers RPE65, Tyrosinase, PEDF, Bestrophin, MitF, and Pax6. This finding further elaborates on the ontogeny depicted above and agrees with current literature regarding the Pax2-induced regulation of MitF and downstream activation of genes associated with terminally differentiated RPE.

Example 4: RPE-Specific Protein Expression Identified by Western Blot Analysis

In order to validate the qPCR results above, and to identify proteins uniquely expressed in RPE cells, a subset of hES-specific and RPE-specific markers were chosen as candidates to assay by western blot, thereby demonstrating translation of the message detected by PCR. Western analysis provides an absolute measure of the robustness of other assays with semi-quantitative (via densitometry) and qualitative data. Results are pictured in FIG. 6. Actin was used as protein loading control.

RPE cells derived from hES cells did not express the hES-specific proteins Oct-4, Nanog, and Rex-1, whereas they expressed RPE65, CRALBP, PEDF, Bestrophin, PAX6, and Otx2. These proteins are therefore prominent markers of RPE cells differentiated from hES cells. By contrast, APRE-19 cells showed an inconclusive pattern of proteomic marker expression.

Example 5: Microarray Gene Expression Profiling of RPE Cells

Manually-purified, hES cell-differentiated hRPE in vitro undergo significant morphological events in culture during the expansion phase. Single-cell suspensions plated in thin cultures depigment and cells increase in surface area. hRPE cells maintain this morphology during expansion when the cells are rapidly dividing. However, when cell density reaches maximal capacity, RPE take on their characteristic phenotypic hexagonal shape and increase pigmentation level by accumulating melanin and lipofuscin.

The level of pigmentation played a major role in our pharmacology study in the RCS rat model. Therefore, we performed global gene expression analysis via microarray on hRPE cells derived from both of the single blastomere-derived hES cell lines MA01 and MA09. Additionally, fetal RPE, ARPE-19, and retinoblastoma cell lines were analyzed as controls.

Our data indicates that this phenotypic change is driven by a change in the global gene expression pattern of these cells, specifically with regard to the expression of PAX6, PAX2, Otx2, MitF, and Tyr.

Figure 7:
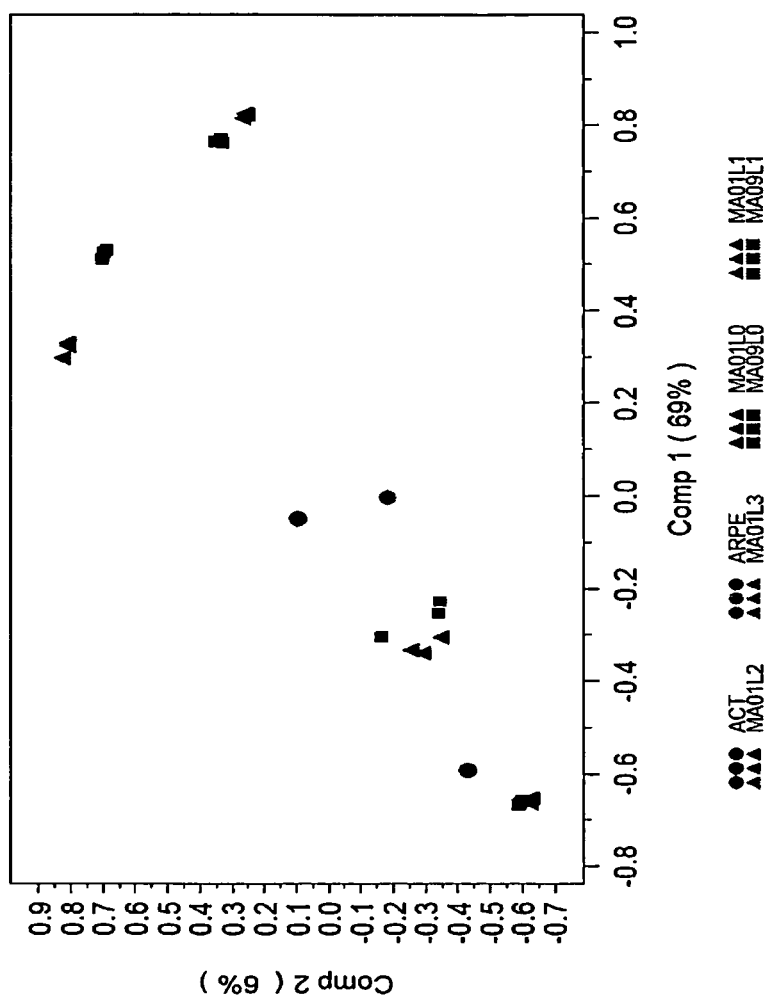
FIG. 7 is a graph showing the principal components analysis plot of microarray gene expressions. Component 1, representing 69% of the variability represents the cell type, whereas Component 2, represents the cell line (i.e., genetic variability). A near-linear scatter of gene expression profiles characterizes the developmental ontogeny of hRPE derived from hES cells.

FIG. 7 depicts a principle components analysis plot scattering of each sample based upon the minimal number of genes accounting for variability amongst each sample. Component 1, representing 69% of the variability represents the cell type, whereas Component 2, represents the cell line (i.e., genetic variability). As can clearly be seen, a near-linear scatter of gene expression profiles characterizes the developmental ontogeny of hRPE derived from hES cells.

Based on ANOVA analysis comparing the respective hES cell line to its RPE counterpart, we selected the 100 highest and lowest expressed genes, and performed computational analysis to select genes related to pleuripotency and eye development. Upregulated genes are shown in Table 2. Down regulated genes are shown in Table 3.

TABLE 2

| | | | |
|---|---|---|---|
| | Upregulated genes of interest reported on microarrays |
| Gene Symbol | Gene Name | Associated with | Description |
| BEST1/VMD2 | bestrophin (vitelliform macular dystrophy 2) | RPE development | Predominantly expressed in the basolateral membrane of the retinal pigment epithelium. Forms calcium-sensitive chloride channels. May conduct other physiologically significant anions such as bicarbonate. Defects in BEST1 are the cause of vitelliform macular dystrophy type 2 (VMD2); also known as Best macular dystrophy (BMD). VMD2 is an autosomal dominant form of macular degeneration that usually begins in childhood or adolescence. VMD2 is characterized by typical "egg-yolk" macular lesions due to abnormal accumulation of lipofuscin within and beneath the retinal pigmented epithelium cells. Progression of the disease leads to destruction of the retinal pigmented epithelium and vision loss. Defects in BEST1 are a cause of adult-onset vitelliform macular dystrophy (AVMD). AVMD is a rare autosomal dominant disorder with incomplete penetrance and highly variable expression. Patients usually become symptomatic in the fourth or fifth decade of life with a protracted disease of decreased visual acuity. |
| CLUL1 (retinal) | clusterin-like 1 (retinal) | retinal development | Associated strongly with cone photoreceptors and appears in different tissues throughout retinal development. |
| CRX | cone-rod homeobox | retinal development | Phosphoreceptor (cone, rod) specific paired-like homeo domain protein, expressed in developing and mature phosphoreceptor cells, binding and transactivating rhodopsin, homolog to *Drosophila* orthodenticle (Otx). Essential for the maintenance of mammalian photoreceptors. |

TABLE 2-continued

Upregulated genes of interest reported on microarrays

| Gene Symbol | Gene Name | Associated with | Description |
|---|---|---|---|
| CRYAA | crystallin, alpha A | eye development | Crystallins are the dominant structural components of the vertebrate eye lens. May contribute to the transparency and refractive index of the lens. Defects in CRYAA are the cause of zonular central nuclear cataract one of a considerable number of phenotypically and genotypically distinct forms of autosomal dominant cataract. This congenital cataract is a common major abnormality of the eye that frequently causes blindness in infants. Crystallins do not turn over as the lens ages, providing ample opportunity for post-translational modifications or oxidations. These modifications may change crystallin solubility properties and favor senile cataract. |
| CRYBA1 | crystallin, beta A1 | eye development | Crystallins are the dominant structural components of the vertebrate eye lens. Crystallins do not turn over as the lens ages, providing ample opportunity for post-translational modifications or oxidations. These modifications may change crystallin solubility properties and favor senile cataract. |
| CRYBA2 | crystallin, beta A2 | eye development | Crystallins are the dominant structural components of the vertebrate eye lens. Crystallins do not turn over as the lens ages, providing ample opportunity for post-translational modifications or oxidations. These modifications may change crystallin solubility properties and favor senile cataract. |
| CRYBA4 | crystallin, beta A4 | eye development | Crystallins are the dominant structural components of the vertebrate eye lens. Defects in CRYBA4 are the cause of lamellar cataract 2. Cataracts are a leading cause of blindness worldwide, affecting all societies. A significant proportion of cases are genetically determined. More than 15 genes for cataracts have been identified, of which the crystallin genes are the most commonly mutated. Lamellar cataract 2 is an autosomal dominant congenital cataract. Defects in CRYBA4 are a cause of isolated microphthalmia with cataract 4 (MCOPCT4). Microphtalmia consists of a development defect causing moderate or severe reduction in size of the eye. Opacities of the cornea and lens, scaring of the retina and choroid, and other abnormalities like cataract may also be present Crystallins do not turn over as the lens ages, providing ample opportunity for post-translational modifications or oxidations. These modifications may change crystallin solubility properties and favor senile cataract. |
| CRYBB1 | crystallin, beta B1 | eye development | Crystallins are the dominant structural components of the vertebrate eye lens. |
| CRYBB2 | crystallin, beta B2 | eye development | Crystallins are the dominant structural components of the vertebrate eye lens. Defects in CRYBB2 are the cause of congenital cerulean cataract 2 (CCA2); also known as congenital cataract blue dot type 2. CCA2 is a form of autosomal dominant congenital cataract (ADCC). Cerulean cataracts have peripheral bluish and white opacifications in concentric layers with occasional central lesions arranged radially. Although the opacities may be observed during fetal development and childhood, usually visual acuity is only mildly reduced until adulthood, when lens extraction is generally necessary. Defects in CRYBB2 are the cause of sutural cataract with punctate and cerulean opacities (CSPC). The phenotype associated with this form of autosomal dominant congenital cataract differed from all other forms of cataract reported. Defects in CRYBB2 are a cause of Coppock-like cataract (CCL). Crystallins do not turn over as the lens ages, providing ample opportunity for post-translational modifications or oxidations. |

TABLE 2-continued

Upregulated genes of interest reported on microarrays

| Gene Symbol | Gene Name | Associated with | Description |
|---|---|---|---|
| CRYBB3 | crystallin, beta B3 | eye development | Crystallins are the dominant structural components of the vertebrate eye lens. Defects in CRYBB3 are the cause of autosomal recessive congenital nuclear cataract 2(CATCN2); a form of nonsyndromic congenital cataract. Non-syndromic congenital cataracts vary markedly in severity and morphology, affecting the nuclear, cortical, polar, or subcapsular parts of the lens or, in severe cases, the entire lens, with a variety of types of opacity. They are one of the major causes of vision loss in children worldwide and are responsible for approximately one third of blindness in infants. Congenital cataracts can lead to permanent blindness by interfering with the sharp focus of light on the retina during critical developmental intervals. Crystallins do not turn over as the lens ages, providing ample opportunity for post-translational modifications or oxidations. These modifications may change crystallin solubility properties and favor senile cataract. |
| DCT/TYRP2 | dopachrome tautomerase (dopachrome delta-isomerase, tyrosine-related protein 2) | pigmented cells | Tyrosine metabolism and Melanin biosynthesis. |
| LHX2 | LIM homeobox 2 | development/ differentiation | Transcriptional regulatory protein involved in the control of cell differentiation in developing lymphoid and neural cell types. |
| LIM2 | lens intrinsic membrane protein 2, 19 kDa | eye development | Present in the thicker 16-17 nm junctions of mammalian lens fiber cells, where it may contribute to cell junctional organization. Acts as a receptor for calmodulin. May play an important role in both lens development and cataractogenesis. |
| MITF | microphthalmia-associated transcription factor | RPE development | Transcription factor for tyrosinase and tyrosinase- related protein 1. Binds to a symmetrical DNA sequence (E-boxes) (5'-CACGTG-3') found in the tyrosinase promoter. Plays a critical role in the differentiation of various cell types as neural crest- derived melanocytes, mast cells, osteoclasts and optic cup-derived retinal pigmented epithelium. Highly expressed in retinal pigmented epithelium. |
| OCA2 | oculocutaneous albinism 11 (pink-eye dilution homolog, mouse) | pigmented cells | Could be involved in the transport of tyrosine, the precursor to melanin synthesis, within the melanocyte. Regulates the pH of melanosome and the melanosome maturation. One of the components of the mammalian pigmentary system. Seems to regulate the postranslational processing of tyrosinase, which catalyzes the limiting reaction in melanin synthesis. May serve as a key control point at which ethnic skin color variation is determined. Major determinant of brown and/or blue eye color. Defects in OCA2 are the cause of oculocutaneous albinism type II (OCA2). OCA2 is an autosomal recessive form of albinism, a disorder of pigmentation in the skin, hair, and eyes. The phenotype of patients with OCA2 is typically somewhat less severe than in those with tyrosinase- deficient OCA1. There are several forms of OCA2, from typical OCA to relatively mild 'autosomal recessive ocular albinism' (AROA). OCA2 is the most prevalent type of albinism throughout the world. The gene OCA is localized to chromosome 15 at 15q11.2-q12 |
| OPN3 | opsin 3 | eye development | May play a role in encephalic photoreception. Strongly expressed in brain. Highly expressed in the preoptic area and paraventricular nucleus of the hypothalamus. Shows highly patterned expression in other regions of the brain, being enriched in selected regions of the cerebral cortex, cerebellar Purkinje cells, a subset of striatal neurons, selected thalamic nuclei, and a subset of interneurons in the ventral horn of the spinal cord. |
| OPN5 | opsin 5 | eye development | Associated with visual perception and phototransduction. |

TABLE 2-continued

Upregulated genes of interest reported on microarrays

| Gene Symbol | Gene Name | Associated with | Description |
|---|---|---|---|
| OTX2 | orthodenticle homolog 2 (Drosophila) | retinal development | Probably plays a role in the development of the brain and the sense organs. Defects in OTX2 are the cause of syndromic microphthalmia 5 (MCOPS5). Microphthalmia is a clinically heterogeneous disorder of eye formation, ranging from small size of a single eye to complete bilateral absence of ocular tissues. Up to 80% of cases of microphthalia occur in association with syndromes that include non-ocular abnormalities such as cardiac defects, facial clefts, microcephaly and hydrocephaly. MCOPS5 patients manifest unilateral or bilateral microphthalmia/clinical anophthalmia and variable additional features including coloboma, microcomea, cataract, retinal dystrophy, hypoplasia or agenesis of the optic nerve, agenesis of the corpus callosum, developmental delay, joint laxity, hypotonia, and seizures. |
| PAX6 | paired box gene 6 (aniridia, keratitis) | RPE development | Transcription factor with important functions in the development of the eye, nose, central nervous system and pancreas. Required for the differentiation of pancreatic islet alpha cells (By similarity). Competes with PAX4 in binding to a common element in the glucagon, insulin and somatostatin promoters (By similarity). Isoform 5a appears to function as a molecular switch that specifies target genes. Defects in Pax6 results in a number of eye defects and malformations. |
| PHC2 | polyhomeotic-like 2 (Drosophila) | development/ differentiation | Component of the Polycomb group (PcG) multiprotein PRC1 complex, a complex required to maintain the transcriptionally repressive state of many genes, including Hox genes, throughout development. PcG PRC1 complex acts via chromatin remodeling and modification of histones; it mediates monoubiquitination of histone H2A 'Lys-119', rendering chromatin heritably changed in its expressibility. |
| PKNOX2 | PBX/knotted 1 homeobox 2 | development/ differentiation | Known to be involved in development and may, along with MEIS, control Pax6. |
| PRKCA | protein kinase C, alpha | cellular signalling | Very important for cellular signaling pathways such as the MAPK, Wnt, PI3, VEGF and Calcium pathways. |
| PROX1 | prospero-related homeobox 1 | eye development | May play a fundamental role in early development of CNS. May regulate gene expression and development of postmitotic undifferentiated young neurons. Highly expressed in lens, retina, and pancreas. |
| PRRX1 | paired related homeobox 1 | development/ differentiation | Necessary for development. Transcription coactivator, enhancing the DNA-binding activity of serum response factor. |
| RAI1 | retinoic acid induced 1 | development/ differentiation | May function as a transcriptional regulator. Regulates transcription through chromatin remodeling by interacting with other proteins in chromatin as well as proteins in the basic transcriptional machinery. May be important for embryonic and postnatal development. May be involved in neuronal differentiation. |
| RARA | retinoic acid receptor, alpha | development/ differentiation | This is a receptor for retinoic acid. This metabolite has profound effects on vertebrate development. This receptor controls cell function by directly regulating gene expression. |
| RARB | retinoic acid receptor, beta | development/ differentiation | This is a receptor for retinoic acid. This metabolite has profound effects on vertebrate development. This receptor controls cell function by directly regulating gene expression. |
| RARRES1 | retinoic acid receptor responder (tazarotene induced) 1 | development/ differentiation | Associated with differentiation and control of cell proliferation. May be a growth regulator that mediates some of the growth suppressive effects of retinoids. |
| RAX | retina and anterior neural fold homeobox | eye development | Plays a critical role in eye formation by regulating the initial specification of retinal cells and/or their subsequent proliferation. Binds to the photoreceptor conserved element-I (PCE-1/Ret 1) in the photoreceptor cell-specific arrestin promoter. |
| RB1 | retinoblastoma 1 (including osteosarcoma) | development/ differentiation | An important regulator of other genes and cell growth. Defects in RB1 are the cause of childhood cancer retinoblastoma (RB). RB is a congenital malignant tumor that arises from the nuclear layers of the retina. |

TABLE 2-continued

Upregulated genes of interest reported on microarrays

| Gene Symbol | Gene Name | Associated with | Description |
|---|---|---|---|
| RDH5 | retinol dehydrogenase 5(11-cis/9-cis) | RPE development | retinol dehydrogenase 5,11-cis, expressed in retinal pigmented epithelium, formerly RDH1. Stereospecific 11-cis retinol dehydrogenase, which catalyzes the final step in the biosynthesis of 11-cis retinaldehyde, the universal chromophore of visual pigments. Abundant in the retinal pigmented epithelium. Defects in RDH5 are a cause of fundus albipunctatus (FA). FA is a rare form of stationary night blindness characterized by a delay in the regeneration of cone and rod photopigments. |
| RGR | retinal G protein coupled receptor | RPE development | Preferentially expressed at high levels in the retinal pigmented epithelium (RPE) and Mueller cells of the neural retina. Retinal opsin related, (rhodopsin homolog)expressed in the retinal pigmented epithelium, encoding a retinaldehyde, preferentially all-trans retinal, binding protein, G protein coupled receptor superfamily. |
| RLBP1/ CRALBP1 | retinaldehyde binding protein 1 | RPE development | Carries 11-cis-retinol and 11-cis-retinaldehyde as endogenous ligands and may be a functional component of the visual cycle. Defects in RLBP1 are a cause of autosomal recessive retinitis pigmentosa (arRP). Retinitis pigmentosa (RP) leads to degeneration of retinal photoreceptor cells. Defects in RLBP1 are the cause of Bothnia retinal dystrophy, also known as Vasterbotten dystrophy. It is another form of autosomal recessive retinitis pigmentosa. Defects in RLBP1 are the cause of Newfoundland rod-cone dystrophy (NFRCD). NFRCD is a retinal dystrophy reminiscent of retinitis punctata albescens but with a substantially lower age at onset and more-rapid and distinctive progression. |
| RPE65 | retinal pigment epithelium-specific protein 65 kDa | RPE development | Retinal pigmented epithelium specific. Retinal pigmented epithelium-specific 65, major microsomal protein, minor role in the isomerisation of all-trans to 11-cis retinal, associated with the endoplasmic reticulum, also expressed in renal tumor cells. Plays important roles in the production of 11-cis retinal and in visual pigment regeneration. |
| RRH | retinal pigment epithelium-derived rhodopsin homolog | RPE development | Found only in the eye, where it is localized to the retinal pigment epithelium (RPE). In the RPE, it is localized to the microvilli that surround the photoreceptor outer segments. May play a role in rpe physiology either by detecting light directly or by monitoring the concentration of retinoids or other photoreceptor-derived compounds. |
| RTN1 | reticulon 1 | development/ differentiation | Expressed in neural and neuroendocrine tissues and cell cultures derived therefrom. Expression of isoform RTN1-C is strongly correlated with neuronal differentiation. |
| RXRB | retinoid X receptor, beta | development/ differentiation | Nuclear hormone receptor. Involved in the retinoic acid response pathway. Binds 9-cis retinoic acid (9C-RA), obligate member of heterodimeric nuclear receptors, steroid/thyroid/retinoic receptor superfamily. |
| RXRG | retinoid X receptor, gamma | development/ differentiation | Nuclear hormone receptor. Involved in the retinoic acid response pathway. Binds 9-cis retinoic acid (9C-RA), obligate member of heterodimeric nuclear receptors, steroid/thyroid/retinoic receptor superfamily. |
| SERPINF1/ PEDF | serpin peptidase inhibitor, clade F (alpha-2 antiplasmin, pigment epithelium derived factor), member 1 | RPE development | Specific expression in retinal pigment epithelial cells and blood plasma. Neurotrophic protein; induces extensive neuronal differentiation in retinoblastoma cells. |
| SIX3 | sine oculis homeobox homolog 3 (Drosophila) | eye development | Expressed during eye development in midline forebrain and in anterior region of the neural plate especially inner retina and later in ganglion cells and in cells of the inner nuclear layer, involved in regulation of eye development. |
| SOX10 | SRY (sex determining region Y)-box 10 | development/ differentiation | Transcription factor that seems to function synergistically with other development associated proteins. Could confer cell specificity to the function of other transcription factors in developing and mature glia. |

TABLE 2-continued

Upregulated genes of interest reported on microarrays

| Gene Symbol | Gene Name | Associated with | Description |
|---|---|---|---|
| SOX5 | SRY (sex determining region Y)-box 5 | development/ differentiation | Expression is associated with craniofacial, skeletal and cartilage development and is highly expressed in brain, testis and various tissues. |
| SOX6 | SRY (sex determining region Y)-box 6 | development/ differentiation | Expression is associated with craniofacial, skeletal and cartilage development and is highly expressed in brain, testis and various tissues. |
| SOX8 | SRY (sex determining region Y)-box 8 | development/ differentiation | May play a role in central nervous system, limb and facial development. |
| SOX9 | SRY (sex determining region Y)-box 9 (campomelic dysplasia, autosomal sex-reversal) | development/ differentiation | Plays an important role in the normal development. May regulate the expression of other genes involved for skeletal and cartilage formation by acting as a transcription factor for these genes. |
| TIMP3 | TIMP metallopeptidase inhibitor 3 (Sorsby fundus dystrophy, pseudoinflammatory) | RPE development | Matrix metalloproteinase, tissue inhibitor 3, expressed in retinal pigment epithelium, placenta, localized in extracellular matrix. Complexes with metalloproteinases (such as collagenases) and irreversibly inactivates them. May form part of a tissue- specific acute response to remodeling stimuli. Defects in TIMP3 are the cause of Sorsby fundus dystrophy (SFD). SFD is a rare autosomal dominant macular disorder with an age of onset in the fourth decade. It is characterized by loss of central vision from subretinal neovascularization and atrophy of the ocular tissues. |
| TTR | transthyretin (prealbumin, amyloidosis type I) | | Thyroid hormone-binding protein. Probably transports thyroxine from the bloodstream to the brain. Defects in TTR are the cause of amyloidosis VII; also known as leptomeningeal amyloidosis or meningocerebrovascular amyloidosis. Leptomeningeal amyloidosis is distinct from other forms of transthyretin amyloidosis in that it exhibits primary involvement of the central nervous system. Neuropathologic examination shows amyloid in the walls of leptomeningeal vessels, in pia arachnoid, and subpial deposits. Some patients also develop vitreous amyloid deposition that leads to visual impairment (oculoleptomeningeal amyloidosis). |
| TYR | tyrosinase (oculocutaneous albinism IA) | pigmented cells | This is a copper-containing oxidase that functions in the formation of pigments such as melanins and other polyphenolic compounds. Defects in TYR are the cause of oculocutaneous albinism type IA (OCA-IA). OCA-I, also known as tyrosinase negative oculocutaneous albinism, is an autosomal recessive disorder characterized by absence of pigment in hair, skin and eyes. OCA-I is divided into 2 types: type IA, characterized by complete lack of tyrosinase activity due to production of an inactive enzyme, and type IB characterized by reduced activity of tyrosinase. OCA-IA patients presents with the life-long absence of melanin pigment after birth and manifest increased sensitivity to ultraviolet radiation and to predisposition to skin cancer defects in TYR are the cause of oculocutaneous albinism type IB (OCA-IB); also known as albinism yellow mutant type. OCA-IB patients have white hair at birth that rapidly turns yellow or blond. |
| TYRP1 | tyrosinase-related protein 1 | pigmented cells | Specific expression in Pigment cells. Oxidation of 5,6-dihydroxyindole-2-carboxylic acid (DHICA) into indole-5,6-quinone-2-carboxylic acid. May regulate or influence the type of melanin synthesized. Defects in TYRP1 are the cause of rufous oculocutaneous albinism (ROCA). ROCA occurs in blacks and is characterized by bright copper-red coloration of the skin and hair and dilution of the color of the iris. Defects in TYRP1 are the cause of oculocutaneous albinism type III (OCA-III); also known as OCA3. OCA-III is a form of albinism with only moderate reduction of pigment. Individuals with OCA-III are recognized by their reddish skin and hair color. |

TABLE 3

Down regulated genes of interest reported on microarrays

| Gene Symbol | Gene Name | Associated with | Description |
| --- | --- | --- | --- |
| ALPL | alkaline phosphatase | ES cells | Elevated expression of this enzyme is associated with undifferentiated pluripotent stem cell. |
| CECR2 | cat eye syndrome chromosome region, candidate 2 | | Part of the CERF (CECR2-containing-remodeling factor) complex, which facilitates the perturbation of chromatin structure in an ATP-dependent manner. May be involved through its interaction with LRPPRC in the integration of cytoskeletal network with vesicular trafficking, nucleocytosolic shuttling, transcription, chromosome remodeling and cytokinesis. Developmental disorders are associated with the duplication of the gene. |
| DCAMKL1 | doublecortin and CaM kinase-like 1 | Embryonic development | Probable kinase that may be involved in a calcium-signaling pathway controlling neuronal migration in the developing brain. |
| DPPA2 | developmental pluripotency associated 2 | ES cells | May play a role in maintaining cell pluripotentiality. |
| DPPA3 | developmental pluripotency associated 3 | ES cells | May play a role in maintaining cell pluripotentiality. |
| DPPA4 | developmental pluripotency associated 4 | ES cells | May indicate cell pluripotentiality. |
| DPPA5/Esg1 | developmental pluripotency associated 5/Embryonic stem cellspecific gene 1 | ES cells | Embryonic stem cell marker. |
| FOXD3 | forkhead box D3 | Pluripotence | Required for maintenance of pluripotent cells in the pre-implantation and peri-implantation stages of embryogenesis. |
| L1TD1ECAT11 | LINE-1 type transposase domain containing 1/ES cell associated transcript 11 | ES cells | Embryonic stem cell marker. |
| NANOG | Nanog homeobox | ES cells | Embryonic stem cell marker. Transcription regulator involved in inner cell mass and embryonic stem (ES) cells proliferation and self-renewal. Imposes pluripotency on ES cells and prevents their differentiation towards extraembryonic endoderm and trophectoderm lineages. |
| NCAM1 | neural cell adhesion molecule 1 | neuroprogenitors | This protein is a cell adhesion molecule involved in neuron-neuron adhesion, neurite fasciculation, outgrowth of neurites. etc. |
| NES/Nestin | nestin | ES cells | Neuralprogenitor cells. |
| NODAL | nodal | Embryonic development | Essential for mesoderm formation and axial patterning during embryonic development. |
| NR5A2/FTF | nuclear receptor subfamily 5, group A, member 2 | Embryonic development | May contribute to the development and regulation of liver and pancreas-specific genes and play important roles in embryonic development. |
| POU5F1/Oct-3/4 | POU domain, class 5, transcription factor 1 | ES cells | Embryonic stem cell marker. Indicator of "Stemness". Transcription factor that binds to the octamer motif (5'-ATTTGCAT-3"). Prime candidate for an early developmental control gene. |
| SOX17 | SRY (sex determining region Y)-box 17 | Inhibitor of differentiation | Negative regulator of the Wnt signalling pathway. |
| SOX2 | SRY (sex determining region Y)-box 2 | ES cells | Indicator of "Stemness". Expressed in inner cell mass, primitive ectoderm and developing CNS. |

TABLE 3-continued

Down regulated genes of interest reported on microarrays

| Gene Symbol | Gene Name | Associated with | Description |
|---|---|---|---|
| TBX3 | T-box 3 (ulnar mammary syndrome) | Embryonic development | Transcriptional repressor involved in developmental processes. Murine T-box gene Tbx3 (T, brachyury)homolog, putative transcription factor, pairing with TBX5, homolog to *Drosophila* optomotor-blind gene (omb), involved in optic lobe and wing development, involved in developmental regulation, expressed in anterior and posterior mouse limb buds, widely expressed in adults |
| TDGF1/ Cripto-1 | teratocarcinoma-derived growth factor 1 | ES cells | Indicator of "Stemness". Could play a role in the determination of the epiblastic cells that subsequently give rise to the mesoderm. |
| TEK/VMCM | TEK tyrosine kinase, endothelial (venous malformations, multiple cutaneous and mucosal) | Early Endothelial progenitors | This protein is a protein tyrosine-kinase transmembrane receptor for angiopoietin 1. It may constitute the earliest mammalian endothelial cell lineage marker. Probably regulates endothelial cell proliferation, differentiation and guides the proper patterning of endothelial cells during blood vessel formation |
| TUBB2A, TUBB2B | tubulin, beta 2A, tubulin, beta 2B | neuroprogenitors | Tubulin is the major constituent of microtubules. It binds two moles of GTP, one at an exchangeable site on the beta chain and one at a non-exchangeable site on the alpha-chain. Often associated with the formation of gap junctions in neural cells. |
| TUBB2A, TUBB2B, TUBB2C, TUBB3, TUBB4 | tubulin, beta 2A, tubulin, beta 2B, tubulin, beta 2C, tubulin, beta 3, tubulin, beta 4 | neuroprogenitors | Tubulin is the major constituent of microtubules. It binds two moles of GTP, one at an exchangeable site on the beta chain and one at a non-exchangeable site on the alpha-chain. Often associated with the formation of gap junctions in neural cells. |
| TUBB3 | tubulin, beta 3 | neuroprogenitors | Tubulin is the major constituent of microtubules. It binds two moles of GTP, one at an exchangeable site on the beta chain and one at a non-exchangeable site on the alpha-chain. Often associated with the formation of gap junctions in neural cells. |
| TWIST1 | twist homolog 1 | Inhibitor of differentiation | Probable transcription factor, which negatively regulates cellular determination and differentiation. |
| UTF1 | undifferentiated embryonic cell transcription factor 1 | ES cells | Embryonic stem cell marker. Acts as a transcriptional coactivator of ATF2. |
| VSNL1 | visinin-like 1 | Inhibitor of rhodopsin | Regulates the inhibition of rhodopsin phosphorylation. |
| ZFP42/Rex-1 | zinc finger protein 42 | ES cells | Embryonic Stem cell marker. |

The present disclosure demonstrates that human RPE cells can be reliably differentiated and expanded from human ES cells under well-defined and reproducible conditions—representing an inexhaustible source of cells for patients with retinal degenerative disorders. The concentration of these cells would not be limited by availability, but rather could be titrated to the precise clinical requirements of the individual. Repeated infusion or transplantation of the same cell population over the lifetime of the patient would also be possible if deemed necessary by the physician. Furthermore, the ability to create banks of matching or reduced-complexity HLA hES lines from which RPE cells could be produced could potentially reduce or eliminate the need for immunosuppressive drugs and/or immunomodulatory protocols altogether.

This disclosure also demonstrates that RPE cells differentiated by the methods described herein express multiple genes that are not expressed by hES cells, fetal RPE cells, or ARPE-19 cells. The unique molecular fingerprint of mRNA and protein expression in the ES-cell derived RPE cells of the invention constitutes a set of markers, such as RPE-65, Bestrophin, PEDF, CRABLP, Otx2, Mit-F, PAX6 and PAX2, that make these RPE cells distinct from cells in the art, such as hES cells, ARPE-19 cells, and fetal RPE cells.

Example 6: Rescue of Visual Function Using RPE Cells from Embryonic Stem Cells Certain retinal diseases are characterized by degeneration of the retinal pigment epithelium (RPE) which in turn results in photoreceptor loss. Examples include Stargardt's macular dystrophy in humans and the genetically-determined dystrophy in the Royal College of Surgeons (RCS) rat. Such a process may also play a role in macular degeneration, affecting more than 10 million people in the US alone.

We investigated conditions under which highly characterized human RPE cells derived from embryonic stem cell lines and manufactured under GMP-compliant conditions could optimally rescue visual function in the RCS rat. MAO1- and MAO9-derived RPE cells were injected into the subretinal space of 23 day-old (P23) RCS rats, maintained post-operatively on oral cyclosporine A immunosuppression. Functional efficacy was tested by threshold optomotor acuity and luminance thresholds recorded from the superior colliculus. All treated eyes were compared with sham-injected and untreated eyes. Histological examination was performed after these functional assessments.

Experimental results showed a clear dose-response in RCS rats. Administration of a preparation comprising $5\times10^4$ RPE cells gave only slightly better optomotor thresholds than shams, whereas a preparation comprising $2\times10^5$ RPE cells gave improved performance versus controls. Preparations comprising $5\times10^5$ RPE cells produced superior performance that was sustained over time. Animals performed at 0.48 c/d at P60, significantly (p<0.001) better than shams (0.26 c/d) with some treated eyes showing normal thresholds (0.6 c/d) and over 0.5 c/d in the best cases at P90 (sham and untreated animals gave a figure 0.16 c/d, a level that indicated substantial visual impairment).

Superior colliculus recordings at P94 also showed much lower luminance threshold responses in RPE cell-injected eyes with some individual recordings within the normal range. Histological studies showed donor cells disposed as a semi-continuous, pigmented cell layer immediately internal to endogenous, host RPE. The donor RPE cells were positive for RPE65 and bestrophin, indicating that the transplanted cells were RPE cells and that the cell maintain their cell fate following transplantation.

Additionally, transplanted animals maintained photoreceptor thickness in comparison to control animals. The photoreceptors in RPE treatment animals were 4-5 cells thick in the rescued area compared with only a single layer in sham and untreated controls.

The results indicate that well-characterized RPE cells derived from embryonic stem cells and manufactured under GMP-compliant conditions survive after transplantation to the subretinal space of RCS rats, do not migrate into the retina and continue to express molecules characteristic of RPE. Most importantly, they achieve significant rescue of visual function in a dose dependent fashion in an animal model of photoreceptor degeneration. The data further suggest that these cells may be effective in limiting and/or reversing the deterioration of vision that accompanies RPE-driven photoreceptor degeneration in human disease.

REFERENCES

Strauss, O., Stumpff, F., Mergler, S., Wienrich, M. & Wiederholt, M. The Royal College of Surgeons rat: an animal model for inherited retinal degeneration with a still unknown genetic defect. *Acta anatomica* 162, 101-111 (1998).

McLaren, M. J., An, W., Brown, M. E. & Inana, G. Analysis of basic fibroblast growth factor in rats with inherited retinal degeneration. *FEBS letters* 387, 63-70 (1996).

McHenry, C. L., et al. MERTK arginine-844-cysteine in a patient with severe rod-cone dystrophy: loss of mutant protein function in transfected cells. *Investigative ophthalmology & visual science* 45, 1456-1463 (2004).

Duncan, J. L., et al. An RCS-like retinal dystrophy phenotype in mer knockout mice. *Investigative ophthalmology & visual science* 44, 826-838 (2003).

Vollrath, D., et al. Correction of the retinal dystrophy phenotype of the RCS rat by viral gene transfer of Mertk. *Proceedings of the National Academy of Sciences of the United States of America* 98, 12584-12589 (2001).

Gal, A., et al. Mutations in MERTK, the human orthologue of the RCS rat retinal dystrophy gene, cause retinitis pigmentosa. *Nature genetics* 26, 270-271 (2000).

D'Cruz, P. M., et al. Mutation of the receptor tyrosine kinase gene Mertk in the retinal dystrophic RCS rat. *Human molecular genetics* 9, 645-651 (2000).

Piesse, C., et al. Expression of aminopeptidase B in the developing and adult rat retina. *Exp Eye Res* 79, 639-648 (2004).

Craitoiu, S. & Florescu, M. [The development of the pigment epithelium and its interrelation with uveal pigment cells]. *Oftalmologia* 41, 12-14 (1997).

Mitashov, V. I. [Cell sources, regulatory factors and gene expression in the regeneration of the crystalline lens and retina in vertebrate animals]. *Izvestiia Akademii nauk*, 298-318 (1996).

Grefenstette, J., Kim, S. & Kauffman, S. An analysis of the class of gene regulatory functions implied by a biochemical model. *Biosystems* 84, 81-90 (2006).

Melnick, M., Chen, H., Min Zhou, Y. & Jaskoll, T. The functional genomic response of developing embryonic submandibular glands to NF-kappa B inhibition. *BMC developmental biology* 1, 15 (2001).

Palumbo, M. C., Colosimo, A., Giuliani, A. & Farina, L. Essentiality is an emergent property of metabolic network wiring. *FEBS letters* 581, 2485-2489 (2007).

Papin, J. A., Price, N. D., Edwards, J. S. & Palsson, B. B. The genome-scale metabolic extreme pathway structure in *Haemophilus influenzae* shows significant network redundancy. *J Theor Biol* 215, 67-82 (2002).

Price, N. D., Papin, J. A. & Palsson, B. O. Determination of redundancy and systems properties of the metabolic network of *Helicobacter pylori* using genome-scale extreme pathway analysis. *Genome research* 12, 760-769 (2002).

Yun, A. J., Lee, P. Y. & Doux, J. D. Efficient inefficiency: biochemical "junk" may represent molecular bridesmaids awaiting emergent function as a buffer against environmental fluctuation. *Medical hypotheses* 67, 914-921 (2006).

Federici, D. & Downing, K. Evolution and development of a multicellular organism: scalability, resilience, and neutral complexification. *Artificial life* 12, 381-409 (2006).

Csermely, P., Soti, C. & Blatch, G. L. Chaperones as parts of cellular networks. *Advances in experimental medicine and biology* 594, 55-63 (2007).

Gillies, R. J. & Gatenby, R. A. Adaptive landscapes and emergent phenotypes: why do cancers have high glycolysis? *J Bioenerg Biomembr* (2007).

Henshall, D. C. & Murphy, B. M. Modulators of neuronal cell death in epilepsy. *Curr Opin Pharmacol* (2007).

Mekel-Bobrov, N., et al. The ongoing adaptive evolution of ASPM and Microcephalin is not explained by increased intelligence. *Human molecular genetics* 16, 600-608 (2007).

Moudy, R. M., Meola, M. A., Morin, L. L., Ebel, G. D. & Kramer, L. D. A newly emergent genotype of West Nile virus is transmitted earlier and more efficiently by Culex mosquitoes. *The American journal of tropical medicine and hygiene* 77, 365-370 (2007).

Sanchez, J. A., Aguilar, C., Dorado, D. & Manrique, N. Phenotypic plasticity and morphological integration in a marine modular invertebrate. *BMC Evol Biol* 7, 122 (2007).

Marc, R. E., Jones, B. W., Watt, C. B. & Strettoi, E. Neural remodeling in retinal degeneration. *Progress in retinal and eye research* 22, 607-655 (2003).

Yeo, S., et al. Characterization of DNA methylation change in stem cell marker genes during differentiation of human embryonic stem cells. *Biochemical and biophysical research communications* 359, 536-542 (2007).

Wang, Z. X., et al. Zfp206 is a transcription factor that controls pluripotency of embryonic stem cells. *Stem cells* (Dayton, Ohio) 25, 2173-2182 (2007).

Ulloa-Montoya, F., et al. Comparative transcriptome analysis of embryonic and adult stem cells with extended and limited differentiation capacity. *Genome Biol* 8, R163 (2007).

Sumi, T., Tsuneyoshi, N., Nakatsuji, N. & Suemori, H. Apoptosis and differentiation of human embryonic stem cells induced by sustained activation of c-Myc. *Oncogene* 26, 5564-5576 (2007).

Lavial, F., et al. The Oct4 homologue PouV and Nanog regulate pluripotency in chicken embryonic stem cells. *Development* (Cambridge, England) 134, 3549-3563 (2007).

Greco, S. J., Liu, K. & Rameshwar, P. Functional Similarities among Genes Regulated by OCT4 in Human Mesenchymal and Embryonic Stem Cells. *Stem cells* (Dayton, Ohio) (2007).

Babaie, Y., et al. Analysis of Oct4-dependent transcriptional networks regulating self-renewal and pluripotency in human embryonic stem cells. *Stem cells* (Dayton, Ohio) 25, 500-510 (2007).

Zhang, X., et al. Derivation of human embryonic stem cells from developing and arrested embryos. *Stem cells* (Dayton, Ohio) 24, 2669-2676 (2006).

Xiao, L., Yuan, X. & Sharkis, S. J. Activin A maintains self-renewal and regulates fibroblast growth factor, Wnt, and bone morphogenic protein pathways in human embryonic stem cells. *Stem cells* (Dayton, Ohio) 24, 1476-1486 (2006).

Player, A., et al. Comparisons between transcriptional regulation and RNA expression in human embryonic stem cell lines. *Stem cells and development* 15, 315-323 (2006).

Pereira, L., Yi, F. & Merrill, B. J. Repression of Nanog gene transcription by Tcf3 limits embryonic stem cell self-renewal. *Mol Cell Biol* 26, 7479-7491 (2006).

O'Neill, L. P., VerMilyea, M. D. & Turner, B. M. Epigenetic characterization of the early embryo with a chromatin immunoprecipitation protocol applicable to small cell populations. *Nature genetics* 38, 835-841 (2006).

Lagarkova, M. A., Volchkov, P. Y., Lyakisheva, A. V., Philonenko, E. S. & Kiselev, S. L. Diverse epigenetic profile of novel human embryonic stem cell lines. *Cell cycle* (Georgetown, Tex. 5, 416-420 (2006).

He, S., et al. Developmental expression of pluripotency determining factors in caprine embryos: novel pattern of NANOG protein localization in the nucleolus. *Molecular reproduction and development* 73, 1512-1522 (2006).

De Jong, J., Weeda, S., Gillis, A. J., Oosterhuis, J. W. & Looijenga, L. H. Differential methylation of the OCT3/4 upstream region in primary human testicular germ cell tumors. *Oncol Rep* 18, 127-132 (2007).

Hattori, N., et al. Epigenetic regulation of Nanog gene in embryonic stem and trophoblast stem cells. *Genes Cells* 12, 387-396 (2007).

Hellman, A. & Chess, A. Gene body-specific methylation on the active X chromosome. *Science* (New York, N.Y. 315, 1141-1143 (2007).

Ohm, J. E., et al. A stem cell-like chromatin pattern may predispose tumor suppressor genes to DNA hypermethylation and heritable silencing. *Nature genetics* 39, 237-242 (2007).

Mitalipov, S., Clepper, L., Sritanaudomchai, H., Fujimoto, A. & Wolf, D. Methylation status of imprinting centers for H19/IGF2 and SNURF/SNRPN in primate embryonic stem cells. *Stem cells* (Dayton, Ohio) 25, 581-588 (2007).

Mitalipov, S. M. Genomic imprinting in primate embryos and embryonic stem cells. *Reproduction, fertility, and development* 18, 817-821 (2006).

Greber, B., Lehrach, H. & Adjaye, J. Silencing of core transcription factors in human EC cells highlights the importance of autocrine FGF signaling for self-renewal. *BMC developmental biology* 7, 46 (2007).

McEwen, B. S. Mood disorders and allostatic load. *Biological psychiatry* 54, 200-207 (2003).

Koob, G. F. Alcoholism: allostasis and beyond. *Alcoholism, clinical and experimental research* 27, 232-243 (2003).

Goldstein, D. S. & McEwen, B. Allostasis, homeostats, and the nature of stress. *Stress* (Amsterdam, Netherlands) 5, 55-58 (2002).

Wei, Q., et al. Overexpressing the glucocorticoid receptor in forebrain causes an aging-like neuroendocrine phenotype and mild cognitive dysfunction. *J Neurosci* 27, 8836-8844 (2007).

McEwen, B. S. Physiology and neurobiology of stress and adaptation: central role of the brain. *Physiological reviews* 87, 873-904 (2007).

Kim, Y., Laposky, A. D., Bergmann, B. M. & Turek, F. W. Repeated sleep restriction in rats leads to homeostatic and allostatic responses during recovery sleep. *Proceedings of the National Academy of Sciences of the United States of America* 104, 10697-10702 (2007).

Pinilla, I., Lund, R. D. & Sauve, Y. Cone function studied with flicker electroretinogram during progressive retinal degeneration in RCS rats. *Exp Eye Res* 80, 51-59 (2005).

Crafoord, S., Geng, L., Seregard, S. & Algvere, P. V. Experimental transplantation of autologous iris pigment epithelial cells to the subretinal space. *Acta ophthalmologica Scandinavica* 79, 509-514 (2001).

Chuang, E. L. & Bird, A. C. Repair after tears of the retinal pigment epithelium. *Eye* (London, England) 2 (Pt 1), 106-113 (1988).

Ricci, F., et al. Modulation of Ku70/80, clusterin/ApoJ isoforms and Bax expression in indocyanine-green-mediated photo-oxidative cell damage. *Ophthalmic research* 39, 164-173 (2007).

Gregerson, D. S., Lew, K. L., McPherson, S. W., Heuss, N. D. & Ferrington, D. A. RPE cells resist bystander killing by CTLs, but are highly susceptible to antigen-dependent CTL killing. *Investigative ophthalmology & visual science* 47, 5385-5394 (2006).

Kim, S. J., et al. Differential expression of vitreous proteins in proliferative diabetic retinopathy. *Current eye research* 31, 231-240 (2006).

Linberg, K. A., Fariss, R. N., Heckenlively, J. R., Farber, D. B. & Fisher, S. K. Morphological characterization of the retinal degeneration in three strains of mice carrying the rd-3 mutation. *Visual neuroscience* 22, 721-734 (2005).

Qin, Y., et al. Long-range activation of Sox9 in Odd Sex (Ods) mice. *Human molecular genetics* 13, 1213-1218 (2004).

Nishiwaki, A., Ueda, T., Ugawa, S., Shimada, S. & Ogura, Y. Upregulation of P-selectin and intercellular adhesion molecule-1 after retinal ischemia-reperfusion injury. *Investigative ophthalmology & visual science* 44, 4931-4935 (2003).

Ida, H., Boylan, S. A., Weigel, A. L. & Hjelmeland, L. M. Age-related changes in the transcriptional profile of mouse RPE/choroid. *Physiological genomics* 15, 258-262 (2003).

Weigel, A. L., Ida, H., Boylan, S. A. & Hjelmeland, L. M. Acute hyperoxia-induced transcriptional response in the mouse RPE/choroid. *Free radical biology & medicine* 35, 465-474 (2003).

Sauka-Spengler, T., Baratte, B., Shi, L. & Mazan, S. Structure and expression of an Otx5-related gene in the dogfish Scyliorhinus canicula: evidence for a conserved role of Otx5 and Crxgenes in the specification of photoreceptors. *Development genes and evolution* 211, 533-544 (2001).

Lovicu, F. J., Kolle, G., Yamada, T., Little, M. H. & McAvoy, J. W. Expression of Crim1 during murine ocular development. *Mechanisms of development* 94, 261-265 (2000).

Otani, A., et al. Expressions of angiopoietins and Tie2 in human choroidal neovascular membranes. *Investigative ophthalmology & visual science* 40, 1912-1920 (1999).

Faure, V., Courtois, Y. & Goureau, O. Differential regulation of nitric oxide synthase-II mRNA by growth factors in rat, bovine, and human retinal pigmented epithelial cells. *Ocular immunology and inflammation* 7, 27-34 (1999).

Mousa, S. A., Lorelli, W. & Campochiaro, P. A. Role of hypoxia and extracellular matrix-integrin binding in the modulation of angiogenic growth factors secretion by retinal pigmented epithelial cells. *Journal of cellular biochemistry* 74, 135-143 (1999).

Collinge, J. E., Simirskii, V. N. & Duncan, M. K. Expression of tissue plasminogen activator during eye development. *Exp Eye Res* 81, 90-96 (2005).

Fisher, S. K., Lewis, G. P., Linberg, K. A. & Verardo, M. R. Cellular remodeling in mammalian retina: results from studies of experimental retinal detachment. *Progress in retinal and eye research* 24, 395-431 (2005).

Francis, M. K., et al. Loss of EPC-1/PEDF expression during skin aging in vivo. The *Journal of investigative dermatology* 122, 1096-1105 (2004).

Marc, R. E. & Jones, B. W. Retinal remodeling in inherited photoreceptor degenerations. *Molecular neurobiology* 28, 139-147 (2003).

Jones, B. W., et al. Retinal remodeling triggered by photoreceptor degenerations. *The Journal of comparative neurology* 464, 1-16 (2003).

MacLaren, R. E., et al. Autologous transplantation of the retinal pigment epithelium and choroid in the treatment of neovascular age-related macular degeneration. *Ophthalmology* 114, 561-570 (2007).

Rezai, K. A., Farrokh-Siar, L., Godowski, K., Patel, S. C. & Ernest, J. T. A model for xenogenic immune response. *Graefes Arch Clin Exp Ophthalmol* 238, 352-358 (2000).

Sauve, Y., Klassen, H., Whiteley, S. J. & Lund, R. D. Visual field loss in RCS rats and the effect of RPE cell transplantation. *Experimental neurology* 152, 243-250 (1998).

Oganesian, A., et al. Scanning and transmission electron microscopic findings during RPE wound healing in vivo. *International ophthalmology* 21, 165-175 (1997).

Kohen, L., Enzmann, V., Faude, F. & Wiedemann, P. Mechanisms of graft rejection in the transplantation of retinal pigment epithelial cells. *Ophthalmic research* 29, 298-304 (1997).

Tamai, M. [Retinal pigment epithelial cell transplantation: perspective]. *Nippon Ganka Gakkai zasshi* 100, 982-1006 (1996).

Gregerson, D. S., Heuss, N. D., Lew, K. L., McPherson, S. W. & Ferrington, D. A. Interaction of retinal pigmented epithelial cells and CD4 T cells leads to T-cell anergy. *Investigative ophthalmology & visual science* 48, 4654-4663 (2007).

Sarks, S., Cherepanoff, S., Killingsworth, M. & Sarks, J. Relationship of Basal laminar deposit and membranous debris to the clinical presentation of early age-related macular degeneration. *Investigative ophthalmology & visual science* 48, 968-977 (2007).

Aisenbrey, S., et al. Retinal pigment epithelial cells synthesize laminins, including laminin 5, and adhere to them through alpha3- and alpha6-containing integrins. *Investigative ophthalmology & visual science* 47, 5537-5544 (2006).

Espinosa-Heidmann, D. G., et al. Cigarette smoke-related oxidants and the development of sub-RPE deposits in an experimental animal model of dry AMD. *Investigative ophthalmology & visual science* 47, 729-737 (2006).

Uno, K., Bhutto, I. A., McLeod, D. S., Merges, C. & Lutty, G. A. Impaired expression of thrombospondin-1 in eyes with age related macular degeneration. *Br J Ophthalmol* 90, 48-54 (2006).

Wang, Z., Paik, D. C., Del Priore, L. V., Burch, R. L. & Gaillard, E. R. Nitrite-modified extracellular matrix proteins deleteriously affect retinal pigment epithelial cell function and viability: a comparison study with nonenzymatic glycation mechanisms. *Current eye research* 30, 691-702 (2005).

Gullapalli, V. K., Sugino, I. K., Van Patten, Y., Shah, S. & Zarbin, M. A. Retinal pigment epithelium resurfacing of aged submacular human Bruch's membrane. *Transactions of the American Ophthalmological Society* 102, 123-137; discussion 137-128 (2004).

Gullapalli, V. K., Sugino, I. K., Van Patten, Y., Shah, S. & Zarbin, M. A. Impaired RPE survival on aged submacular human Bruch's membrane. *Exp Eye Res* 80, 235-248 (2005).

Itaya, H., Gullapalli, V., Sugino, I. K., Tamai, M. & Zarbin, M. A. Iris pigment epithelium attachment to aged submacular human Bruch's membrane. *Investigative ophthalmology & visual science* 45, 4520-4528 (2004).

Tezel, T. H., Del Priore, L. V. & Kaplan, H. J. Reengineering of aged Bruch's membrane to enhance retinal pigment epithelium repopulation. *Investigative ophthalmology & visual science* 45, 3337-3348 (2004).

Roth, F., Bindewald, A. & Holz, F. G. Key pathophysiologic pathways in age-related macular disease. *Graefes Arch Clin Exp Ophthalmol* 242, 710-716 (2004).

Zarbin, M. A. Current concepts in the pathogenesis of age-related macular degeneration. *Archives of ophthalmology* 122, 598-614 (2004).

Tian, J., Ishibashi, K. & Handa, J. T. The expression of native and cultured RPE grown on different matrices. *Physiological genomics* 17, 170-182 (2004).

Koenekoop, R. K. Choroideremia is Caused by a Defective Phagocytosis by the RPE of Photoreceptor Disc Membranes, not by an Intrinsic Photoreceptor Defect. *Ophthalmic genetics* 28, 185-186 (2007).

Chang, Y. & Finnemann, S. C. Tetraspanin CD81 is required for the {alpha}vbeta5-integrin-dependent particle-binding step of RPE phagocytosis. *Journal of cell science* 120, 3053-3063 (2007).

Mukherjee, P. K., et al. Photoreceptor outer segment phagocytosis attenuates oxidative stress-induced apoptosis with concomitant neuroprotectin D1 synthesis. *Proceedings of the National Academy of Sciences of the United States of America* 104, 13158-13163 (2007).

Schutt, F., Volcker, H. E. & Dithmar, S. [N-acetylcysteine improves lysosomal function and enhances the degrada-

We claim:

1. A method of producing retinal pigment epithelial (RPE) cells, comprising
   (a) culturing human pluripotent stem cells for 7-14 days to form embryoid bodies or aggregates in suspension culture in a medium that comprises less than 5% animal-derived protein;
   (b) culturing the embryoid bodies or aggregates as an adherent culture in a medium that comprises less than 5% animal-derived protein, wherein RPE cells appear within 14-28 days of adherent culture;
   (c) selecting RPE cells from the culture of step (b);
   (d) culturing the RPE cells selected in step (c) thereby producing a culture comprising RPE cells.

2. The method of claim 1, wherein the RPE cells of step (d) are further cultured to produce a culture of mature RPE cells.

3. The method of claim 1, wherein the cells of step (a) are cultured for 7-10 days.

4. The method of claim 1, wherein the embryoid bodies or aggregates of step (b) are cultured for 28 days or more.

5. The method of claim 1, wherein the RPE cells of step (d) are cultured with a growth factor selected from the group consisting of: EGF, bFGF, VEGF, and recombinant insulin-like growth factor.

6. The method of claim 1, wherein the RPE cells of step (d) are cultured in the presence of one or more of: heparin, hydrocortisone, or ascorbic acid.

7. The method of claim 1, wherein the human pluripotent stem cells are induced pluripotent stem (iPS) cells.

8. The method of claim 1, wherein in step (a) the human pluripotent stem cells are cultured to form aggregates.

9. The method of claim 1, wherein the human pluripotent stem cells are human embryonic stem cells.

10. The method of claim 1, wherein step (c) comprises contacting the culture of step (b) with an enzyme that causes RPE cells to detach from the adherent culture and selecting detached pigmented cells or detached cell clusters containing pigmented cells.

11. The method of claim 10, wherein said enzyme is selected from the group consisting of collagenase IV and dispase.

12. The method of claim 11, wherein step (c) further comprises dissociating the selected cell clusters containing pigmented cells, thereby forming a single cell suspension comprising RPE cells.

13. The method of claim 1, wherein the medium in step (b) comprises activin A.

* * * * *